US012116408B2

(12) United States Patent
Henriksen et al.

(10) Patent No.: US 12,116,408 B2
(45) Date of Patent: *Oct. 15, 2024

(54) SITE DIRECTED MUTAGENESIS OF TREM-1 ANTIBODIES FOR DECREASING VISCOSITY

(71) Applicant: Novo Nordisk A/S, Bagsvaerd (DK)

(72) Inventors: Anette Henriksen, Alleroed (DK); Kristian Kjaergaard, Ballerup (DK); Vibeke Westphal Stennicke, Kokkedal (DK); Charlotte Wiberg, Bjärred (SE)

(73) Assignee: NOVO NORDISK A/S, Bagsvaerd (DK)

( * ) Notice: Subject to any disclaimer, the term of this patent is extended or adjusted under 35 U.S.C. 154(b) by 541 days.

This patent is subject to a terminal disclaimer.

(21) Appl. No.: 17/380,404

(22) Filed: Jul. 20, 2021

(65) Prior Publication Data
US 2022/0010012 A1 Jan. 13, 2022

Related U.S. Application Data

(60) Continuation of application No. 16/203,327, filed on Nov. 28, 2018, now Pat. No. 11,072,654, which is a division of application No. 15/325,865, filed as application No. PCT/EP2015/066501 on Jul. 17, 2015, now Pat. No. 10,179,814.

(30) Foreign Application Priority Data

Jul. 17, 2014 (EP) .................................... 14177547
Nov. 26, 2014 (EP) .................................... 14194893

(51) Int. Cl.
C07K 16/28 (2006.01)

(52) U.S. Cl.
CPC ...... C07K 16/2803 (2013.01); C07K 2299/00 (2013.01); C07K 2317/55 (2013.01); C07K 2317/565 (2013.01); C07K 2317/76 (2013.01); C07K 2317/90 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | |
|---|---|---|---|
| 4,444,887 A | 4/1984 | Hoffmann | |
| 4,522,811 A | 6/1985 | Eppstein et al. | |
| 4,676,980 A | 6/1987 | Segal et al. | |
| 4,683,195 A | 7/1987 | Mullis et al. | |
| 4,716,111 A | 12/1987 | Osband et al. | |
| 4,736,866 A | 4/1988 | Leder et al. | |
| 4,741,900 A | 5/1988 | Alvarez et al. | |
| 4,816,397 A | 3/1989 | Boss et al. | |
| 4,816,567 A | 3/1989 | Cabilly et al. | |
| 4,870,009 A | 9/1989 | Evans et al. | |
| 4,873,191 A | 10/1989 | Wagner et al. | |
| 4,873,316 A | 10/1989 | Meade et al. | |
| 4,946,778 A | 8/1990 | Ladner et al. | |
| 4,683,202 A | 11/1990 | Mullis | |
| 4,980,286 A | 12/1990 | Morgan et al. | |
| 4,987,071 A | 1/1991 | Cech et al. | |
| 5,116,742 A | 5/1992 | Cech et al. | |
| 5,223,409 A | 6/1993 | Ladner et al. | |
| 5,225,539 A | 7/1993 | Winter | |
| 5,258,498 A | 11/1993 | Huston et al. | |
| 5,272,057 A | 12/1993 | Smulson et al. | |
| 5,272,071 A | 12/1993 | Chappel | |
| 5,283,317 A | 2/1994 | Saifer et al. | |
| 5,328,470 A | 7/1994 | Nabel et al. | |
| 5,403,484 A | 4/1995 | Ladner et al. | |
| 5,413,923 A | 5/1995 | Kucherlapati et al. | |
| 5,420,526 A | 5/1995 | Fensch | |
| 5,424,288 A | 6/1995 | Order | |
| 5,427,908 A | 6/1995 | Dower et al. | |
| 5,436,146 A | 7/1995 | Shenk et al. | |
| 5,459,039 A | 10/1995 | Modrich et al. | |
| 5,474,981 A | 12/1995 | Leder et al. | |
| 5,498,531 A | 3/1996 | Jarrell | |
| 5,516,637 A | 5/1996 | Huang et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,571,698 A | 11/1996 | Ladner et al. | |

(Continued)

FOREIGN PATENT DOCUMENTS

EP 0264166 A1 4/1988
EP 0439095 A2 7/1991
(Continued)

OTHER PUBLICATIONS

ABCAM., Anti-PGRPS antibody [188C424] (ab13903), accessea at http://www.abcam.com/PGRPS-antibody-188C424-ab13903.html accessed on Jun. 12, 2014.
ABCAM., Atlas Antibodies; United States Biologicai, List of Anti-PGRP Abs, accessed at http://www.antibodyresource.com/search/Antibodies/ffb4623f-177 d-13a0-16e2-1105223fb311/PG RP accessed on Jan. 8, 2014.
ABCAM., Atlas Antibodies, United States Biological, 075594 Antibodies, List of Anti-PGRP Abs, accessed at http://www.antibodyresource. com/search/ Anti bod ies/125bfebf-0922 -1605-3416-8213e4 73b271/07 5594 accessed on Jan. 8, 2014.
(Continued)

Primary Examiner — Daniel C Gamett
(74) Attorney, Agent, or Firm — Morgan, Lewis & Bockius LLP

(57) ABSTRACT

Antibodies that are capable of specifically binding and preventing the activation of TREM-1, a protein expressed on monocytes, macrophages and neutrophils with both good affinity and low viscosity at clinically relevant concentrations are described. Such antibodies find utility in the treatment of individuals with an inflammatory disease, such as rheumatoid arthritis and inflammatory bowel disease.

11 Claims, 8 Drawing Sheets
Specification includes a Sequence Listing.

(56) References Cited

U.S. PATENT DOCUMENTS

| | | | |
|---|---|---|---|
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,420,526 B1 | 7/2002 | Ruben et al. |
| 6,504,010 B1 | 1/2003 | Wang et al. |
| 6,509,448 B2 | 1/2003 | Wang et al. |
| 6,638,768 B1 | 10/2003 | Le Mouellic et al. |
| 6,858,204 B2 | 2/2005 | Henderson et al. |
| 6,878,687 B1 | 4/2005 | Ruben et al. |
| 8,013,116 B2 | 9/2011 | Faure et al. |
| 8,231,878 B2 | 7/2012 | Colonna et al. |
| 8,981,061 B2 | 3/2015 | Colonna et al. |
| 9,000,127 B2 | 4/2015 | Stennicke et al. |
| 9,550,830 B2 | 1/2017 | Stennicke et al. |
| 9,856,320 B2 | 1/2018 | Cogswell et al. |
| 2002/0128444 A1 | 9/2002 | Gingras et al. |
| 2002/0161201 A1 | 10/2002 | Filpula et al. |
| 2002/0172952 A1 | 11/2002 | Henderson et al. |
| 2002/0197669 A1 | 12/2002 | Bangur et al. |
| 2003/0049618 A1 | 3/2003 | Ruben et al. |
| 2003/0054363 A1 | 3/2003 | Henderson et al. |
| 2003/0077282 A1 | 4/2003 | Bigler et al. |
| 2003/0134283 A1 | 7/2003 | Peterson et al. |
| 2003/0165875 A1 | 9/2003 | Colonna et al. |
| 2003/0166068 A1 | 9/2003 | Ashida et al. |
| 2003/0170255 A1 | 9/2003 | Watanabe et al. |
| 2003/0175858 A1 | 9/2003 | Ruben et al. |
| 2003/0211510 A1 | 11/2003 | Henderson et al. |
| 2004/0236092 A1 | 11/2004 | Dziarski et al. |
| 2005/0238646 A1 | 10/2005 | Ledbetter et al. |
| 2005/0255114 A1 | 11/2005 | Labat et al. |
| 2006/0183125 A1 | 8/2006 | Mariani et al. |
| 2009/0092582 A1 | 4/2009 | Bogin et al. |
| 2010/0310560 A1 | 12/2010 | Colonna et al. |
| 2016/0251434 A1 | 9/2016 | Colonna et al. |
| 2017/0183406 A1 | 6/2017 | Gurney et al. |
| 2017/0190775 A1 | 7/2017 | Stennicke et al. |
| 2017/0298130 A1 | 10/2017 | Henriksen et al. |
| 2017/0320946 A1 | 11/2017 | Colonna et al. |

FOREIGN PATENT DOCUMENTS

| | | | |
|---|---|---|---|
| EP | 0439098 A2 | 7/1991 |
| EP | 0592106 A1 | 4/1994 |
| EP | 0239400-81 | 8/1994 |
| EP | 1022286 A1 | 7/2000 |
| EP | 0592106 B1 | 11/2004 |
| EP | 1498424 A2 | 1/2005 |
| EP | 0519596-81 | 2/2005 |
| TW | 1431878 A | 8/2014 |
| WO | WO-8809810 A1 | 12/1988 |
| WO | WO-8910134 A1 | 11/1989 |
| WO | WO-9002809 A1 | 3/1990 |
| WO | WO-9011354 A1 | 10/1990 |
| WO | WO-9109967 A1 | 7/1991 |
| WO | WO-9110737 A1 | 7/1991 |
| WO | WO-9110741 A1 | 7/1991 |
| WO | WO-9200968 A1 | 1/1992 |
| WO | WO-9201047 A1 | 1/1992 |
| WO | WO-9206180 A1 | 4/1992 |
| WO | WO-9218619 A1 | 10/1992 |
| WO | WO-8220316 A2 | 11/1992 |
| WO | WO-9222324 A1 | 12/1992 |
| WO | WO-9222635 A1 | 12/1992 |
| WO | WO-9304169 A1 | 3/1993 |
| WO | WO-9311236 A1 | 6/1993 |
| WO | WO-9314188 A1 | 7/1993 |
| WO | WO-9320221 A1 | 10/1993 |
| WO | WO-9321232 A1 | 10/1993 |
| WO | WO-9408598 A1 | 4/1994 |
| WO | WO-9410300 A1 | 5/1994 |
| WO | WO-9412649 A2 | 6/1994 |
| WO | WO-9416101 A2 | 7/1994 |
| WO | WO-9515982 A2 | 6/1995 |
| WO | WO-9520401 A1 | 8/1995 |
| WO | WO-9633735 A1 | 10/1996 |
| WO | WO-9634096 A1 | 10/1996 |
| WO | WO-9707668 A1 | 3/1997 |
| WO | WO-9707669 A1 | 3/1997 |
| WO | WO-9808871 A1 | 3/1998 |
| WO | WO-9816654 A1 | 4/1998 |
| WO | WO-9824893 A2 | 6/1998 |
| WO | WO-9839446 A2 | 9/1998 |
| WO | WO-9839448 A2 | 9/1998 |
| WO | WO-9846645 A2 | 10/1998 |
| WO | WO-9850433 A2 | 11/1998 |
| WO | WO-9902686 A1 | 1/1999 |
| WO | WO-0000610 A2 | 1/2000 |
| WO | WO-0153312 A1 | 7/2001 |
| WO | WO-0190304 A2 | 11/2001 |
| WO | WO-03025138 A2 | 3/2003 |
| WO | WO-03029401 A2 | 4/2003 |
| WO | WO-03030835 A2 | 4/2003 |
| WO | WO-03037267 A2 | 5/2003 |
| WO | WO-03060071 A2 | 7/2003 |
| WO | WO-03061712 A1 | 7/2003 |
| WO | WO-03080667 A2 | 10/2003 |
| WO | WO-2004020591 A2 | 3/2004 |
| WO | WO-2004081233 A1 | 9/2004 |
| WO | WO-2005005601 A2 | 1/2005 |
| WO | WO-2005040219 A1 | 5/2005 |
| WO | WO-2005048823 A2 | 6/2005 |
| WO | WO-2005071408 A1 | 8/2005 |
| WO | WO-2005091944 A2 | 10/2005 |
| WO | WO-2005113606 A2 | 12/2005 |
| WO | WO-2006028595 A2 | 3/2006 |
| WO | WO-2006028714 A1 | 3/2006 |
| WO | WO-2006056492 A1 | 6/2006 |
| WO | WO-2006065582 A2 | 6/2006 |
| WO | WO-2006078463 A2 | 7/2006 |
| WO | WO-2006097537 A2 | 9/2006 |
| WO | WO-2006135886 A2 | 12/2006 |
| WO | WO-2006138275 A2 | 12/2006 |
| WO | WO-2007146968 A2 | 12/2007 |
| WO | WO-2008049113 A2 | 4/2008 |
| WO | WO-2008088849 A2 | 7/2008 |
| WO | WO-2008121563 A2 | 10/2008 |
| WO | WO-2009018386 A1 | 2/2009 |
| WO | WO-2009020802 A2 | 2/2009 |
| WO | WO-2009030771 A1 | 3/2009 |
| WO | WO-2009117033 A2 | 9/2009 |
| WO | WO-2009126380 A2 | 10/2009 |
| WO | WO-2009141359 A1 | 11/2009 |
| WO | WO-2010006060 A2 | 1/2010 |
| WO | WO-2010042747 A2 | 4/2010 |
| WO | WO-2010044952 A2 | 4/2010 |
| WO | WO-2010065439 A1 | 6/2010 |
| WO | WO-2010084169 A2 | 7/2010 |
| WO | WO-2010132370 A2 | 11/2010 |
| WO | WO-2010141469 A2 | 12/2010 |
| WO | WO-2010142665 A1 | 12/2010 |
| WO | WO-2011005481 A1 | 1/2011 |
| WO | WO-2011028952 A1 | 3/2011 |
| WO | WO-2011047097 A2 | 4/2011 |
| WO | WO-2011055968 A2 | 5/2011 |
| WO | WO-2011069104 A2 | 6/2011 |
| WO | WO-2011091078 A | 7/2011 |
| WO | WO-2011137362 A1 | 11/2011 |
| WO | WO-2012064733 A2 | 5/2012 |

(56) References Cited

FOREIGN PATENT DOCUMENTS

| | | |
|---|---|---|
| WO | WO-2012088290 A2 | 6/2012 |
| WO | WO-2012088302 A2 | 6/2012 |
| WO | WO-2012109624 A2 | 8/2012 |
| WO | WO-2013120553 A1 | 8/2013 |
| WO | WO-2014072876 A1 | 5/2014 |
| WO | WO-2015042246 A1 | 3/2015 |
| WO | WO-2016009086 A1 | 1/2016 |

OTHER PUBLICATIONS

ABCAM., Atlas Antibodies, United States Biological, Cytokine tag7 Antibodies, List of Anti-PGRP Abs, accessed at http://www.antibodyresource .com/search/ Antibodies/17 a31750-abb9-1 c85-b872-c3a2e 796189c/Cytokine-tag 7 accessed on Jan. 8, 2014.

ABCAM., Atlas Antibodies, United States Biological, Peptidoglycan recognition protein 1 Antibodies, List of Anti-PGRP Abs, accessed at http://www.antibodyresource.com/search/Antibodies/1208015d-1757 -26ad-1 f04-6c9171376236/Peptidoglycan- recognition-protein-1 accessed on Jan. 8, 2014.

ABCAM., Atlas Antibodies, United States Biological, Peptidoglycan recognition protein 1 Antibodies, List of Anti-PGRP Abs, accesses at http://www.antibodyresource. com/search/A ntibod ies/ede383a0-138e-c073-1710-f9db 1294bc02/Peptidoglycan- recognition-protein-1 accessed on Jan. 8, 2014.

ABCAM., Atlas Antibodies, United States Biological Peptidoglycan recognition protein short Antibodies, List of Anti- PGRP Abs accessed on http://www.antibodyresource.com/search/Antibodies/3a8d5b63-12d8-12d6-1 b99-11fb615758f5/Peptidoglycan- recognition-protein-short accessed on Jan. 8, 2014.

ABCAM., Atlas Antibodies, United States Biological,Tag7 Antibodies, List of Anti-PGRP Abs accessed at http://www.antibodyresource. com/search/ Anti bod ies/04 1 07168-8402-51 df-bb36-4dd2bf8e 16d 1/Tag accessed on Jan. 8, 2014.

ABCAM., Atlas Antibodies, United States Biological,TNFSF3L Antibodies, List of Anti-PGRP Abs accessed at http://www.antibodyresource.com/search/Antibodies/f33a5126-45cd-5220-878c-0fd9aa63ba35/TNFSF3L accessed on Jan. 8, 2014.

Abravaya, K., et al., "Detection of Point Mutations with a Modified Ligase Chain Reaction (Gap-LCR)," Nucleic Acids Research 23(4):675-682, Oxford University Press, England (Feb. 1995).

Adams, P.D., et al., "PHENIX: A comprehensive Python-based System for Macromolecular Structure Solution," Acta Crystallographica. Section D, Biological Crystallography 66(Pt 2):213-221, Wiley-Blackwell, United States (2010).

Aderem, A. and Ulevitch, R.J., "Toll-like Receptors in the Induction of the Innate Immune Response," Nature 406(6797):782-787, Nature Publishing Group, England (Aug. 2000).

Adrie, C., et al., "Postresuscitation Disease After Cardiac Arrest: A Sepsis-like Syndrome?," Current Opinion in Critical Care 10(3):208-212, Lippincott Williams & Wilkins, United States (Jun. 2004).

Alexander, H.R., et al., "A Recombinant Human Receptor Antagonist to Interleukin 1 Improves Survival After Lethal Endotoxemia in Mice," The Journal of Experimental Medicine 173(4):1029-1032, Rockefeller University Press, United States (Apr. 1991).

Allahham, A., et al., "Flow and Injection Characteristics of Pharmaceutical Parenteral Formulations Using a Micro-capillary Rheometer," International Journal of Pharmaceutics 270(1-2):139-148, Elsevier/North-Holland Biomedical Press, Netherlands (2004).

Amann, E., et al., "Tightly Regulated Tac Promoter Vectors Useful for the Expression of Unfused and Fused Proteins in *Escherichia coli*," Gene 69(2):301-315, Elsevier/North-Holland, Netherlands (1988).

Amatngalim, G.D., et al., "Cathelicidin Peptide LL-37 Modulates TREM-1 Expression and Inflammatory Responses to Microbial Compounds," Inflammation 34(5):412-425, Kluwer Academic/Plenum Publishers, United States (Oct. 2011).

Ames, R.S., et al., "Coversion of Murine Fabs Isolated From a Combinatorial Phage Display Library to Full Length Immunoglobulins," Journal of Immunological Methods 184(2):177-186, Elsevier, Netherlands (1995).

Andersen, M.D. and Faber, J.H., "Structural Characterization of Both the Non-proteolytic and Proteolytic Activation Pathways of Coagulation Factor XIII Studied by Hydrogen-deuterium Exchange Mass Spectrometry," International Journal of Mass Spectrometry 302(1-3):139-148, (2011).

Angal, S., et al., "A Single Amino Acid Substitution Abolishes the Heterogeneity of Chimeric Mouse/Human (IgG4) Antibody," Molecular Immunology 30(1):105-108, Pergamon Press, England (Jan. 1993).

Anti-TREM1 antibody produced in rabbit, Sigma-Aldrich HPA005563 product information, accessed at, https://www.laborme.com/product/Sigma-Aldrich/HPA005563.html, last accessed on Jun. 12, 2018, 3 pages.

Appelmelk, B.J., et al., "Use of Mucin and Hemoglobin in Experimental Murine Gram-negative Bacteremia Enhances the Immunoprotective Action of Antibodies Reactive With the Lipopolysaccharide Core Region," Antonie van Leeuwenhoek 52(6):537-542, Springer, Netherlands (1986).

Arnon, et al., "Monoclonal Antibodies for Immunotargeting of Drugs in Cancer Therapy," in Monoclonal Antibodies And Cancer Therapy, Reisfeld et al., eds., Alan R. Liss, Inc., (1985), pp. 243-256.

Arts, R.J., et al., "TREM-1 Interaction with the LPS/TLR4 Receptor Complex," European Cytokine Network 22(1):11-14, John Libbey Eurotext Ltd, France (2011).

Attwood, T.K., "Genomics, The Babel of Bioinformatics," Science 290(5491):471-473, American Association for the Advancement of Science, United States (Oct. 2000).

Ausubel, et al., Current Protocols in Molecular Biology, John Wiley & Sons (1992).

Bakker, A.B., et al., "DAP12-deficient Mice Fail to Develop Autoimmunity Due to Impaired Antigen Priming," Immunity 13(3):345-353, Cell Press, United States (Sep. 2000).

Bakker, A.B., et al., "Myeloid DAP12-associating Lectin (MDL)-1 is a Cell Surface Receptor Involved in the Activation of Myeloid Cells," Proceedings of the National Academy of Sciences 96(17):9792-9796, National Academy of Sciences, United States (Aug. 1999).

Bakker, A.B., et al., "NK Cell Activation: Distinct Stimulatory Pathways Counterbalancing Inhibitory Signals," Human Immunology 61(1):18-27, Elsevier/North-Holland, United States (Jan. 2000).

Baldari, C., et al., "A Novel Leader Peptide Which Allows Efficient Secretion of a Fragment of Human Interleukin 1 Beta in *Saccharomyces Cerevisiae*," The EMBO Journal 6(1):229-234, Wiley Blackwell, England (Jan. 1987).

Baldwin, et al., "Analysis Results, and Future Prospective of the Therapeutic Use of the Radiolabeled Antibody in Cancer Therapy," in Monoclonal Antibodies for Cancer Detection and Therapy, eds. Adacemic Press, pp. 303-316 (1985).

Banerji, J., et al., "A Lymphocyte-specific Cellular Enhancer Is Located Downstream of the Joining Region in Immunoglobulin Heavy Chain Genes," Cell 33(3):729-740, Cell Press, United States (Jul. 1983).

Barany, F., "Genetic Disease Detection and Dna Amplification Using Cloned Thermostable Ligase," Proceedings of the National Academy of Sciences 88(1):189-193, National Academy of Sciences, United States (Jan. 1991).

Bartel, D.P. and Szostak, J.W., "Isolation of New Ribozymes From a Large Pool of Random Sequences," Science 261(5127):1411-1418, American Association for the Advancement of Science, United States (Sep. 1993).

Bartel, P. "Elimination of false positives that arise in using the two-hybrid system." Biotechniques 14(6):920-924, (1993).

Bauer, S., et al., "Activation of NK Cells and T Cells by NKG2D, a Receptor for Stress-inducible MICA," Science 285(5428):727-729, American Association for the Advancement of Science, United States (Jul. 1999).

Begum, N.A., et al., "Mycobacterium Bovis Bcg Cell Wall-specific Differentially Expressed Genes Identified by Differential Display

(56) References Cited

OTHER PUBLICATIONS and cDNA Subtraction in Human Macrophages," Infection and Immunity 72(2):937-948, Americans Society For Microbiology, United States (Feb. 2004).
Benda, P., et al., "Differentiated Rat Glial Cell Strain in Tissue Culture," Science 161(3839):370-371, American Association for the Advancement of Science, United States (Jul. 1968).
Bethea, D., et al., "Mechanisms of Self-association of a Human Monoclonal Antibody CNTO607," Protein Engineering, Design & Selection 25(10):531-537, Oxford University Press, England (2012).
Better, M., et al., "*Escherichia coli* Secretion of an Active Chimeric Antibody Fragment," Science 240(4855):1041-1043, Association for the Advancement of Science, United States (May 1988).
Beutler, B., "Endotoxin, Toll-like Receptor 4, and the Afferent Limb of Innate Immunity" Current opinion in microbiology 3(1):23-28, Current Biology, England (Feb. 2000).
Beutler, B., et al., "Passive Immunization Against Cachectin/tumor Necrosis Factor Protects Mice From Lethal Effect of Endotoxin," Science 229(4716):869-871, American Association for the Advancement of Science, United States (Aug. 1985).
Bird, R.E., et al., "Single-chain Antigen-binding Proteins," Science 242(4877):423-426, Association for the Advancement of Science, United States (Oct. 1988).
Bleharski, J.R., et al., "A Role for Triggering Receptor Expressed on Myeloid Cells-1 in Host Defense During the Early-induced and Adaptive Phases of the Immune Response," Journal of Immunology 170(7):3812-3818, American Association of Immunologists, United States (Apr. 2003).
Boesen, J.J., et al., "Circumvention of Chemotherapy-induced Myelosuppression by Transfer of the mdr1 Gene," Biotherapy 6(4):291-302, Kluwer Academic Publishers, Netherlands (1993).
Bolin, S.R., et al., "Survey of Cell Lines in the American Type Culture Collection for Bovine Viral Diarrhea Virus," Journal of Virological Methods 48(2-3):211-221, Elsevier/North-Holland Biomedical Press, Netherlands (Jul. 1994).
Bone, R.C., et al., "Definitions for Sepsis and Organ Failure and Guidelines for the Use of Innovative Therapies in Sepsis. The ACCP/SCCM Consensus Conference Committee. American College of Chest Physicians/Society of Critical Care Medicine," Chest 101(6):1644-1655, Elsevier, United States (Jun. 1992).
Bone, R.C., "The Pathogenesis of Sepsis," Annals of Internal Medicine 115(6):457-469, American College of Physicians, United States (Sep. 1991).
Bordelon-Riser, M.E., "Necessity for Two Human Chromosomes for Human Chorionic Gonadotropin Production in Human-mouse Hybrids," Somatic Cell Genetics 5(5):597-613, Plenum, United States (Sep. 1979).
Bork, P. and Bairoch, A., "Go Hunting in Sequence Databases but Watch out for the Traps," Trends in Genetics 12(10):425-427, Elsevier Trends Journals, England (Oct. 1996).
Bork, P., "Powers and Pitfalls in Sequence Analysis: The 70% Hurdle," Genome Research 10(4):398-400, Cold Spring Harbor Laboratory Press, United States (Apr. 2000).
Bostanci, N., et al., "Involvement of the TREM-1/DAP12 Pathway in the Innate Immune Responses to Porphyromonas Gingivalis," Molecular Immunology 49(1-2):387-394, Pergamon Press, England (Oct. 2011).
Bouchon, A., et al., "Cutting Edge: Inflammatory Responses Can Be Triggered by TREM-1, A Novel Receptor Expressed on Neutrophils and Monocytes," Journal of Immunology 164(10):4991-4995, American Association of Immunologists, United States (2000).
Bouchon, A., et al., "TREM-1 Amplifies Inflammation and is a Crucial Mediator of Septic Shock," Nature 410(6832):1103-1107, Nature Publishing Group, England (2001).
Bout, A., et al., "Lung Gene Therapy: In Vivo Adenovirus-mediated Gene Transfer to Rhesus Monkey Airway Epithelium," Human Gene Therapy 5(1):3-10, Liebert, United States (Jan. 1994).
Bradley, A., "Modifying the Mammalian Genome by Gene Targeting," Current Opinion in Biotechnology 2(6):823-829, Elsevier, England (Dec. 1991).

Bradley, "Teratocarcinomas and Embryonic Stem Cells: A Practical Approach," Robertson, ed., IRL, Oxford, pp. 113-152 (1987).
Brenner, S.E., "Errors In Genome Annotation," Trends in Genetics 15(4):132-133, Elsevier Trends Journals, England (Apr. 1999).
Brinkmann, U., et al., "Phage Display of Disulfide-stabilized Fv Fragments," Journal of Immunological Methods 182(1):41-50, Elsevier, Netherlands (1995).
Brown, M., et al., "Tolerance to Single, but not Multiple, Amino Acid Replacements in Antibody VH CDR2: A Means of Minimizing B Cell Wastage from Somatic Hypermutation?," Journal of Immunology 156(9):3285-3291, American Association of Immunologists, United States (May 1996).
Burton, D.R. and Barbas, C.F. 3rd., "Human Antibodies From Combinatorial Libraries," Advances in Immunology 57:191-280, Academic Press, United States (1994).
Byrne, G.W. and Ruddle, F.H., "Multiplex Gene Regulation: a Two-tiered Approach to Transgene Regulation in Transgenic Mice," Proceedings of the National Academy of Sciences USA 86(14):5473-5477 (Jul. 1989).
Calame, K., et al., "Transcriptional Controlling Elements in the Immunoglobulin and T Cell Receptor Loci," Advances in Immunology 43:235-275 (1988).
Calandra, T., et al, "Protection From Septic Shock by Neutralization of Macrophage Migration Inhibitory Factor," Nature Medicine 6(2):164-170, Nature Publishing Company, United States (2000).
Camper, S.A. and Tilghman, S.M., "Postnatal Repression of the Alpha-fetoprotein Gene is Enhancer Independent," Genes & Development 3:537-546 (1989).
Cantoni, C., et al., "Nkp44, a Triggering Receptor Involved in Tumor Cell Lysis by Activated Human Natural Killer Cells, Is a Novel Member of the Immunoglobulin Superfamily," Journal of Experimental Medicine 189(5):787-796, Rockefeller University Press, United States (Mar. 1999).
Carrell., et al., "A Novel Procedure for the Synthesis of Libraries Containing Small Organic Molecules," Angewandte Chemie International Edition in English 33:2059-2061, (1994).
Casset, F., et al., "A Peptide Mimetic of an Anti-CD4 Monoclonal Antibody By Rational Design," Biochemical and Biophysical Research Communications 307(1):198-205, Academic Press,United States (Jul. 2003).
Cella, M., et al., "A Novel Inhibitory Receptor (ILT3) Expressed on Monocytes, Macrophages, and Dendritic Cells Involved in Antigen Processing," Journal of Experimental Medicine 185(10):1743-1751, Rockefeller University Press, United States (May 1997).
Chaudhri, A., et al., "The Role of Amino Acid Sequence in the Self-association of Therapeutic Monoclonal Antibodies: Insights From Coarse-grained Modeling," The Journal of Physical Chemistry. B 117(5):1269-1279, American Chemical Society, United States (2013).
Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (Nov. 1999).
Cho, C.Y., et al., "An unnatural biopolymer," Science 261(5126):1303-1305, American Association for the Advancement of Science, United States (1993).
Chomel, B.B., et al., "Bartonella Henselae Prevalence in Domestic Cats in California: Risk Factors and Association Between Bacteremia and Antibody Titers," Journal of Clinical Microbiology 33(9):2445-2450, American Society for Microbiology, United States (Sep. 1995).
Chothia, C. and Lesk, A.M., "Canonical Structures for the Hypervariable Regions of Immunoglobulins," Journal of Molecular Biology 196(4):901-917, Elsevier Science, United States (Aug. 1987).
Clowes, M.M., et al., "Long-term Biological Response of Injured Rat Carotid Artery Seeded With Smooth Muscle Cells Expressing Retrovirally Introduced Human Genes," The Journal of Clinical Investigation 93(2):644-651, American Society for Clinical Investigation, United States (Feb. 1994).

(56) References Cited

OTHER PUBLICATIONS

Cohen, A.S., et al., "Emerging Technologies for Sequencing Antisense Oligonucleotides: Capillary Electrophoresis and Mass Spectrometry," Advances in Chromatography 36:127-162, CRC Press, United States (1996).

Cohen, J., "The Immunopathogenesis of Sepsis," Nature 420(6917):885-891, Nature Publishing Group, England (Dec. 2002).

Cohen, J., "TREM-1 in Sepsis," Lancet 358(9284):776-778, Elsevier, England (Sep. 2001).

Colbere-Garapin, F., et al., "A New Dominant Hybrid Selective Marker for Higher Eukaryotic Cells," Journal of Molecular Biology 150(1):1-14, Elsevier, England (Jul. 1981).

Collart, M.A., et al., "Regulation of Tumor Necrosis Factor Alpha Transcription in Macrophages: Involvement of Four Kappa B-like Motifs and of Constitutive and Inducible Forms of NF-kappa B," Molecular and Cellular Biology 10(4):1498-1506, American Society for Microbiology, United States (Apr. 1990).

Colonna, M. and Facchetti, F., "TREM-1 (Triggering Receptor Expressed on Myeloid Cells): A New Player in Acute Inflammatory Responses," The Journal of Infectious Diseases 187(2):S397-S401, Oxford University Press, United States (Jun. 2003).

Colonna, M., "TREMS in the Immune System and Beyond," Nature Reviews. Immunology 3(6):445-453, Nature Pub. Group, England (Jun. 2003).

Connolly, B.D., et al., "Weak Interactions Govern the Viscosity of Concentrated Antibody Solutions. High-throughput Analysis Using the Diffusion Interaction Parameter," Biophysical Journal 103(1):69-78, Cell Press, United States.

Coskun, T., et al., "Fibroblast Growth Factor 21 Corrects Obesity in Mice," Endocrinology 149(12):6018-6027, Oxford University Press, United States (Dec. 2008).

Cotten, M., et al., "Receptor-mediated Transport of DNA Into Eukaryotic Cells," Methods in Enzymology 217:618-644, Academic Press, United States (1993).

Cotton, R.G., "Current Methods of Mutation Detection," Mutation Research 285(1):125-144, Elsevier, Netherlands (Jan. 1993).

Cotton, R.G., et al., "Reactivity of Cytosine and Thymine in Single-base-pair Mismatches With Hydroxylamine and Osmium Tetroxide and Its Application to the Study of Mutations," Proceedings of the National Academy of Sciences 85(12):4397-4401, National Academy of Sciences, United States (Jun. 1988).

Cox, G., et al., "IL-10 Enhances Resolution of Pulmonary Inflammation in Vivo by Promoting Apoptosis of Neutrophils," The American Journal of Physiology 271(4 Pt 1):L566-L571, American Physiological Society, United States (Oct. 1996).

Cronin, M.T., et al., "Cystic Fibrosis Mutation Detection by Hybridization to Light-generated DNA Probe Arrays," Human Mutation 7(3):244-255, Wiley-Liss, United States (1996).

Cruickshank, D.W., "Remarks About Protein Structure Precision," Acta Crystallographica. Section D, Biological Crystallography 55(Pt 3):583-601, Wiley-Blackwell, United States (1999).

Cruikshank, W.W., et al., "A Lipidated Anti-Tat Antibody Enters Living Cells and Blocks HIV-1 Viral Replication," Journal of Acquired Immune Deficiency Syndromes and Human Retrovirology 14(3):193-203, Lippincott Williams & Wilkins, United States (Mar. 1997).

Cull, M.G., et al., "Screening for Receptor Ligands Using Large Libraries of Peptides Linked to the C Terminus of the Lac Repressor," Proceedings of the National Academy of Sciences 89(5):1865-1869, National Academy of Sciences, United States (Mar. 1992).

Cwirla, S.E., et al., "Peptides on phage: a vast library of peptides for identifying ligands," Proceedings of the National Academy of Sciences 87(16):6378-6382, National Academy of Sciences, United States, (1990).

Database EMBL, Sequence from Patent WO200283856-A2, Sep. 17, 2003 "Human G-protein Coupled Receptor Phosphorylation Site Peptide SEQ ID 131," retrieved from EBI Database accession No. ABJ38803.

Database EMBL, Sequence Information from JP2000116377-A, Oct. 10, 2000 "N-terminus of Porcine Trypsin," retrieved from EBI Database accession No. AAB03087.

Davenport, C.M., et al., "Inhibition of Pro-inflammatory Cytokine Generation by CTLA4-lg in the Skin and Colon of Mice Adoptively Transplanted with CD45RBhi CD4+T Cells Correlates with Suppression of Psoriasis and Colitis," International Immunopharmacology 2(5):653-672, Elsevier Science, Netherlands (2002).

Daws, M.R., et al., "Cloning and Characterization of a Novel Mouse Myeloid DAP12-associated Receptor Family," European Journal of Immunology 31(3):783-791, Wiley-VCH, Germany (Mar. 2001).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

Devlin, J.J., et al., "Random peptide libraries: a source of specific protein binding molecules," Science 249(4967):404-406, American Association for the Advancement of Science, United States (1990).

Dewitt, S.H., et al., "Diversomers: an approach to nonpeptide, nonoligomeric chemical diversity," Proceedings of the National Academy of Sciences 90(15):6909-6913, National Academy of Sciences, United States (1993).

Dietrich, J., et al., "Cutting Edge: Signal-regulatory Protein Beta 1 is a DAP12-associated Activating Receptor Expressed in Myeloid Cells," Journal of Immunology 164(1):9-12, American Association of Immunologists, United States (Jan. 2000).

Dinarello, C.A., "Proinflammatory and Anti-inflammatory Cytokines as Mediators in the Pathogenesis of Septic Shock," Chest 112(6):321S-329S, Elsevier, United States (Dec. 1997).

Doerks T., et al., "Protein Annotation: Detective Work for Function Prediction," Trends in Genetics 14(6):248-250, Elsevier Trends Journals, England (Jun. 1998).

Downey, G.P., et al., "Intracellular Signaling in Neutrophil Priming and Activation," Seminars in Cell Biology 6(6):345-356, Academic Press, England (Dec. 1995).

Drescher, A., "Characterization of Biological Interactions with Biacore," XP007919211, pp. 1-26 (Jun. 2011).

Dziarski, R., et al., "Peptidoglycan Recognition in Innate Immunity," Endotoxin Research 11(5):304-310, Sage Publications, United States (2005).

Dziarski, R., et al., "Review: Mammalian Peptidoglycan Recognition Proteins (PGRPs) in Innate Immunity," Innate Immunity 16(3):168-174, Sage Publications, United States (Jun. 2010).

Dziarski, R., Gupta, D., "The Peptidoglycan Recognition Proteins (PGRPs)," Genome Biology 7(8):232.1-232.13, BioMed Central Ltd, England (2006).

Dziarski, R., "Peptidoglycan Recognition Proteins (PGRPS)," Molecular Immunology 40(12):877-886, Pergamon Press, England (Feb. 2004).

Echtenacher, B., et al., "Critical Protective Role of Mast Cells in a Model of Acute Septic Peritonitis," Nature 381(6577):75-77, Nature Publishing Group, England (May 1996).

Echtenacher, B., et al., "Requirement of Endogenous Tumor Necrosis Factor/cachectin for Recovery From Experimental Peritonitis," Journal of Immunology 145(11):3762-3766, American Association of Immunologists, United States (Dec. 1990).

Echtenacher, B., et al., "Tumor Necrosis Factor-dependent Adhesions as a Major Protective Mechanism Early in Septic Peritonitis in Mice," Infection and Immunity 69(6):3550-3555, American Society For Microbiology, United States (Jun. 2001).

Edlund, T., et al., "Cell-specific Expression of the Rat Insulin Gene: Evidence for Role of Two Distinct 5' Flanking Elements," Science 230(4728):912-916, American Association for the Advancement of Science, United States (Nov. 1985).

Emsley, P., et al., "Features and Development of Coot," Acta Crystallographica. Section D, Biological Crystallography 66(Pt 4):486-501, Wiley-Blackwell, United States (2010).

Engh, R.A. and Huber, R., "Accurate Bond and Angle Parameters for X-ray Protein Structure Refinement," Acta Crystallographica Section A 47(4):392-400, (1991).

(56) References Cited

OTHER PUBLICATIONS

Erb, E., et al., "Recursive deconvolution of combinatorial chemical libraries," Proceedings of the National Academy of Sciences 91(24):11422-11426, National Academy of Sciences, United States (1994).

Erickson, S.K., "Nonalcoholic Fatty Liver Disease," Journal of Lipid Research 50:S412-S416, American Society for Biochemistry and Molecular Biology, United States (Apr. 2009).

Eskandari, M.K., et al., "Anti-tumor Necrosis Factor Antibody Therapy Fails to Prevent Lethality After Cecal Ligation and Puncture or Endotoxemia," Journal of Immunology 148(9):2724-2730, American Association of Immunologists, United States (May 1992).

European Search Report for EP Application No. 14177547.8, European Patent Office, Munich, Germany, mailed on Feb. 2, 2015, 10 pages.

European Search Report for EP Application No. 14194893.5, European Patent Office, Munich, Germany, mailed on Jan. 14, 2016, 12 pages.

Facchetti, F., et al., "Suppurative Granulomatous Lymphadenitis. Immunohistochemical Evidence for a B-cell-associated Granuloma," The American Journal of Surgical Pathology 16(10):955-961, Wolters Kluwer Health, Inc., United States (Oct. 1992).

Felici, F., et al., "Selection of Antibody Ligands from a Large Library of Oligopeptides Expressed on a Multivalent Exposition Vector," Journal of Molecular Biology 222(2):301-310, Elsevier Science, United States (Nov. 1991).

Fell, H.P., et al., "Genetic Construction and Characterization of a Fusion Protein Consisting of a Chimeric F(ab') With Specificity for Carcinomas and Human IL-2," Journal of Immunology 146(7):2446-2452, American Association of Immunologists, United States (Apr. 1991).

Fiering, S., et al., "Single Cell Assay of a Transcription Factor Reveals a Threshold in Transcription Activated by Signals Emanating From the T-cell Antigen Receptor," Genes & Development 4(10):1823-1834, Cold Spring Harbor Laboratory Press, United States (1990).

Finn, P.J., et al., "Synthesis and Properties of DNA-PNA Chimeric Oligomers," Nucleic Acids Research 24(17):3357-3363, Oxford University Press, England (Sep. 1996).

Fisher, C.J., et al., "Treatment of Septic Shock with the Tumor Necrosis Factor Receptor: Fc Fusion Protein The Soluble TNF Receptor Sepsis Study Group," The New England Journal of Medicine 334(26):1697-1702, Massachusetts Medical Society, United States (Jun. 1996).

Fodor, S.P., et al., "Multiplexed biochemical assays with biological chips," Nature 364(6437):555-556, Nature Publishing Group, United States (1993).

Forster, R., et al., "CCR7 Coordinates the Primary Immune Response by Establishing Functional Microenvironments in Secondary Lymphoid Organs," Cell 99(1):23-33, Cell Press, United States (Oct. 1999).

Gallop, M.A., et al., "Applications of combinatorial technologies to drug discovery. 1. Background and peptide combinatorial libraries," Journal of Medicinal Chemistry 37(9):1233-1251, (1994).

Garcia, R.A., et al., "Hydrogen/deuterium Exchange Mass Spectrometry for Investigating Protein-ligand Interactions," Assay and Drug Development Technologies 2(1):81-91, Mary Ann Liebert, Inc., United States (2004).

Gasparini, P., et al., "Restriction Site Generating-polymerase Chain Reaction (RG-PCR) for the Probeless Detection of Hidden Genetic Variation: Application to the Study of Some Common Cystic Fibrosis Mutations," Molecular and Cellular Probes 6(1):1-7, Academic Press, England (Feb. 1992).

Gautier, C., et al., "alpha-DNA Iv: alpha-anomeric an beta-anomeric Tetrathymidylates Covalently Linked to Intercalating Oxazolopyridocarbazole Synthesis, Physicochemical Properties and Poly," Nucleic Acids Research 15(16):6625-6641, Oxford University Press, England (Aug. 1987).

GenBank, "AL681036 XGC-gastrula Xenopus tropicalis cDNA clone TGas068I03 5-, mRNA sequence," Accession No. AL681036.2, accessed at https://www.ncbi.nlm.nih.gov/nucest/Al681036, Nov. 10, 2003.

GenBank, "AL962750 XGC-gastrula Xenopus tropicalis cDNA clone TGas109m03 5-, mRNA sequence," Accession No. AL962750.2, accessed at https://www.ncbi.nlm.nih.gov/nucest/Al962750, Dec. 5, 2003.

GenBank, "AL968134 XGC-gastrula Xenopus tropicalis cDNA clone TGas113h24 5-, mRNA sequence," Accession No. AL968134.2, accessed at https://www.ncbi.nlm.nih.gov/nucest/Al968134, Dec. 5, 2003.

GenBank, "Cloning Vector plRED1hyg, Complete Plasmid Sequence," Accession No. U89672.1, accessed at https://www.ncbi.nlm.nih.gov/nuccore/U89672, Mar. 21, 1997.

GenBank, "CM0-TT0011-251099-080-f05 TT0011 *Homo sapiens* cDNA, mRNA sequence," Accession No. AW394041.1, accessed at https://www.ncbi.nlm.nih.gov/nucest/AW394041, Feb. 4, 2000.

GenBank, "*Homo sapiens* triggering receptor expressed on monocytes 1 mRNA, complete cds," Accession No. AF196329.1, accessed at https://www.ncbi.nlm.nih.gov/nuccore/AF196329, May 24, 2000.

GenBank, "*Homo sapiens* Triggering Receptor Expressed on Myeloid Cells 1 (TREM1), mRNA," Accession No. NM_018643.2, accessed at https://www.ncbi.nlm.nih.gov/nuccore/NM_018643.2, May 15, 2011.

GenBank, "*Homo sapiens* triggering receptor expressed on myeloid cells 2 mRNA, complete cds," Accession No. AF213457.1, accessed at https://www.ncbi.nlm.nih.gov/nucest/AF213457, May 23, 2000.

GenBank, "HUM517F10B Human placenta polyA+ (TFujiwara) *Homo sapiens* cDNA clone GEN-517F10 5-, mRNA sequence," Accession No. D78812.1, accessed at https://www.ncbi.nlm.nih.gov/nucest/D78812, Jul. 20, 2006.

GenBank, "ne55f09.s1 NCI_CGAP_Co3 *Homo sapiens* cDNA clone IMAGE:901289 3-, mRNA sequence" Accession No. AA494171.1, accessed at https://www.ncbi.nlm.nih.gov/nucest/AA494171, Jan. 6, 2011.

GenBank, "T3 end of clone 024CH09 of library smBAC1 from strain Puerto-Rican of Schistosoma mansoni, genomic survey sequence," Accession No. AL621023.1, accessed at https://www.ncbi.nlm.nih.gov/nucest/Al621023, Oct. 11, 2001.

GenBank, "T3 end of clone AR0AA015A03 of library AR0AA from strain CBS 732 of Zygosaccharomyces rouxii, genomic survey sequence," Accession No. AL394092.1, accessed at https://www.ncbi.nlm.nih.gov/nucgss/AI394092, Feb. 16, 2014.

GenBank, "tb95h04.x1 NCI_CGAP_Co16 *Homo sapiens* cDNA clone IMAGE:2062135 3-, mRNA sequence," Accession No. AI337247.1, accessed at https://www.ncbi.nlm.nih.gov/nucest/AI337247, Jan. 8, 2011.

GenBank, "Tetraodon nigroviridis genome survey sequence T7 end of clone 245F13 of library G from Tetraodon nigroviridis, genomic survey sequence," Accession No. AL186456, accessed at https://www.ncbi.nlm.nih.gov/nucgss/AL186456, May 19, 2010.

GenBank, "Triggering Receptor Expressed on Myeloid Cells 1 isoform 1 Precursor [*Homo sapiens*]," Accession No. NP_061113.1, accessed at https://www.ncbi.nlm.nih.gov/protein/8924262/, Jul. 31, 2017.

GenBank, "Triggering Receptor Expressed on Myeloid Cells 1 Isoform 1 Precursor [Mus musculus]," Accession No. NP_067381.1, accessed at http://www.ncbi.nlm.nih.gov/protein/NP_067381, Jun. 3, 2017.

GenBank, "Triggering Receptor Expressed on Myeloid Cells," Accession No. Q9NP99, accessed at http://www.uniprot.org/uniprot/Q9NP99, Jun. 7, 2017.

GenBank, "UI-H-BI1-acf-g-10-0-UI.s1 NCI_CGAP_Sub3 *Homo sapiens* cDNA clone IMAGE:2714299 3-, mRNA sequence," Accession No. AW135801.1, accessed at https://www.ncbi.nlm.nih.gov/nucest/AW135801, Jan. 6, 2011.

GenBank, "UI-H-Bl1-ada-h-08-0-UI.s1 NCI_CGAP_Sub3 *Homo sapiens* cDNA clone IMAGE:2716286 3-, mRNA sequence," Accession No. AW139363.1, accessed at https://www.ncbi.nlm.nih.gov/nucest/AW139363, Jan. 7, 2011.

(56) References Cited

OTHER PUBLICATIONS

GenBank, "UI-H-Bl1-aea-d-11-0-UI.s1 NCI_CGAP_Sub3 *Homo sapiens* cDNA clone IMAGE:2718764 3-, mRNA sequence," Accession No. AW139572.1, accessed at https://www.ncbi.nlm.nih.gov/nucest/AW139572, Jan. 7, 2011.

Genbank, "UI-H-Bl1-aea-d-12-0-Uls1 NCI_CGAP_Sub3 *Homo sapiens* cDNA clone IMAGE:2718766 3-, mRNA sequence," Accession No. AW139573.1, accessed at https://www.ncbi.nlm.nih.gov/nucest/AW139573, Oct. 30, 1999.

GenBank, "xm62e07.x1 NCI_CGAP_GC6 *Homo sapiens* cDNA clone IMAGE:2688804 3-, mRNA sequence," Accession No. AW274906.1. accessed at https://www.ncbi.nlm.nih.gov/nucest/AW274906, Jan. 3, 2000.

GenBank, "yw70g03.r1 Soares_placenta_8to9weeks_2NbHP8to9W *Homo sapiens* cDNA clone IMAGE:257620 5-, mRNA sequence," Accession No. N41388.1, accessed https://www.ncbi.nlm.nih.gov/nucest/N41388, Jan. 24, 1996.

GenBank, "zk87c02.r1 Soares_pregnant_uterus_NbHPU *Homo sapiens* cDNA clone IMAGE:489794 5-, mRNA sequence," Accession No. AA099288.1, accessed at https://www.ncbi.nlm.nih.gov/nucest/AA099288, Jan. 28, 2011.

GenBank, "zk87c02.r1 Soares_pregnant_uterus_NbHPU *Homo sapiens* cDNA clone IMAGE:489794 3-, mRNA sequence," Accession No. AA101983.1, accessed at https://www.ncbi.nlm.nih.gov/nucest/AA101983, Jan. 28, 2011.

Gencic, S. and Hudson, L.D., "Conservative Amino Acid Substitution in the Myelin Proteolipid Protein of Jimpymsd Mice," The Journal of Neuroscience 10(1):117-124, Society for Neuroscience, United States (Jan. 1990).

Gentz, R., et al., "Bioassay for Trans-activation using Purified Human Immunodeficiency Virus Tat-encoded Protein: Trans-activation Requires mRNA Synthesis," Proceedings of the National Academy of Sciences USA 86(3):821-824, National Academy of Sciences, United States (Feb. 1989).

Ghosh, A., et al., "A Novel Antimicrobial Peptidoglycan Recognition Protein in the Cornea," Investigative Ophthalmology & Visual Science 50(9):4185-4191, Association For Research In Vision And Ophthalmology, United States (Sep. 2009).

Gibbs, R.A., et al., "Detection of Single DNA Base Differences by Competitive Oligonucleotide Priming," Nucleic Acids Research 17(7):2437-2448, Oxford University Press, England (Apr. 1989).

Gibot, S., et al., "A Soluble Form of the Triggering Receptor Expressed on Myeloid Cells-1 Modulates the Inflammatory Response in Murine Sepsis," The Journal of Experimental Medicine 200(11):1419-1426, Rockefeller University Press, United States (Dec. 2004).

Gibot, S., et al., "Modulation of the Triggering Receptor Expressed on the Myeloid Cell Type 1 Pathway in Murine Septic Shock," Infection and immunity 74(5):2823-2830, American Society For Microbiology, United States (May 2006).

Gibot, S., et al., "Soluble Triggering Receptor Expressed on Myeloid Cells and the Diagnosis of Pneumonia," The New England Journal of Medicine 350(5):451-458, Massachusetts Medical Society, United States (Jan. 2004).

Gibot, S., et al., "Plasma Level of a Triggering Receptor Expressed on Myeloid Cells-1: its Diagnostic Accuracy In Patients with Suspected Sepsis," Annals of Internal Medicine 141(1):9-15, American College of Physicians—American Society of Internal Medicine, United States (Jul. 2004).

Gillies, S.D., et al., "Antibody-targeted Interleukin 2 Stimulates T-cell Killing of Autologous Tumor Cells," Proceedings of the National Academy of Sciences of the United States of America 89(4):1428-1432, National Academy of Sciences, United States (1992).

Gillies, S.D., et al., "High-level Expression of Chimeric Antibodies Using Adapted cDNA Variable Region Cassettes," Journal of Immunological Methods 125(1-2):191-202, Elsevier, Netherlands (1989).

Gingras, M.C., et al., "TREM-1, MDL-1, and DAP12 Expression is Associated with a Mature Stage of Myeloid Development," Molecular Immunology 38(11):817-824, Pergamon Press, England (Mar. 2002).

Glauser, M.P., et al., "Septic Shock: Pathogenesis," Lancet 338(8769):732-736, Elsevier, England (Sep. 1991).

Goldspiel, B.R., et al., "Human Gene Therapy," Clinical Pharmacy 12(7):488-505, American Society Of Hospital Pharmacists, United States (1993).

Gon, S., et al., "Involvement of Two Types of TNF Receptor in TNF-alpha Induced Neutrophil Apoptosis," Microbiology and Immunology 40(6):463-465, Wiley-Blackwell, Australia (1996).

Griffin, H.G. and Griffin, A.M., "DNA Sequencing, Recent Innovations and Future Trends," Applied Biochemistry and Biotechnology 38(1-2):147-159, Humana Press, United States (Jan.-Feb. 1993).

Griffin, M.P., et al., "Abnormal Heart Rate Characteristics Preceding Neonatal Sepsis and Sepsis-like Illness," Pediatric Research 53(6):920-926, Nature Publishing Group, United States (Jun. 2003).

Grossman, M. and Wilson, J.M., "Retroviruses: Delivery Vehicle to the Liver," Current Opinion in Genetics & Development 3(1):110-114, Elsevier, England (Feb. 1993).

Grundy, S.M., et al., "Definition of Metabolic Syndrome: Report of the National Heart, Lung, and Blood Institute/American Heart Association Conference on Scientific Issues Related to Definition," Circulation 109(3):433-438, Lippincott Williams & Wilkins, United States (Jan. 2004).

Guan, R., et al., "Crystal Structure of Human Peptidoglycan Recognition Protein S (PGRP-S) at 1.70 A Resolution," Molecular Biology 347(4):683-691, Elsevier, England (Apr. 2005).

Guatelli, J.C., et al., "Isothermal, in Vitro Amplification of Nucleic Acids by a Multienzyme Reaction Modeled After Retroviral Replication," Proceedings of the National Academy of Sciences 87(5):1874-1878, Naional Academy of Sciences, United States (Mar. 1990).

Haapala, D.K., et al., "Isolation From Cats of an Engogenous Type C Virus With a Novel Envelope Glycoprotein," Journal of Virology 53(3):827-833, American Society For Microbiology, United States (Mar. 1985).

Hammerling, G.J., et al., "Monoclonal Antibodies and T -Cell Hybridomas," pp. 563-681, Elsevier, Newyork (1981).

Harlow, E. and Lane, D., Antibodies: A Laboratory Manual, 2nd Edition, Cold Spring Harbor Press (1988).

Haselmayer, P., et al., "TREM-1 Ligand Expression on Platelets Enhances Neutrophil Activation," Blood 110(3):1029-1035, American Society of Hematology, United States (Aug. 2007).

Haseloff, J., et al., "Simple RNA Enzymes with New and Highly Specific Endoribonuclease Activities," Nature 334(6183):585-591, Nature Publishing Group, England (Aug. 1988).

Hayashi, K., "PCR-SSCP: A Method for Detection of Mutations," Genetic Analysis, Techniques and Applications 9(3):73-79, Elsevier, Netherlands (Jun. 1992).

He, F., et al., "High-throughput Dynamic Light Scattering Method for Measuring Viscosity of Concentrated Protein Solutions," Analytical Biochemistry 399(1):141-143, Elsevier, United States (2010).

He, X.M., et al., "Expression of O6-methylguanine-DNA Methyltransferase in Six Human Medulloblastoma Cell Lines," Cancer Research 52(5):1144-1148, American Association for Cancer Research, United States (Mar. 1992).

Hebert, M.J., et al., "Sequential Morphologic Events During Apoptosis of Human Neutrophils. Modulation by Lipoxygenase-derived Eicosanoids," Journal of Immunology 157(7):3105-3115, American Association of Immunologists, United States (Oct. 1996).

Helene, C., et al., "Control of Gene Expression by Triple Helix-forming Oligonucleotides. The Antigene Strategy," Annals of the New York Academy of Sciences 660:27-36, Blackwell, United States (Oct. 1992).

Helene, C., "The Anti-gene Strategy: Control of Gene Expression by Triplex-forming-oligonucleotides," Anti-cancer Drug Design 6(6):569-584, Oxford University Press, United States (1991).

Hellstrom, et al., "Antibodies for Drug Delivery" in Controlled Drug Delivery, 2nd edition, Robinson et al., eds., Marcel Dekker, Inc., (1987), pp. 623-653.

Hiscott, J., et al., "Characterization of a Functional NF-kappa B Site in the Human Interleukin 1 Beta Promoter: Evidence for a Positive Autoregulatory Loop," Molecular and Cellular Biology 13(10):6231-6240, American Society For Microbiology, United States (Oct. 1993).

(56) References Cited

OTHER PUBLICATIONS

Hoffmann, J.A., et al., "Phylogenetic Perspectives in Innate Immunity," Science 284(5418):1313-1318, American Association for the Advancement of Science, United States (May 1999).
Holliger, P, and Hudson, P.J., "Engineered Antibody Fragments and the Rise of Single Domains," Nature Biotechnology 23(9):1126-1136, Nature America Publishing, United States (2005).
Hotchkiss, R.S. and Karl, I.E., "The Pathophysiology and Treatment of Sepsis," The New England Journal of Medicine 348(2):138-150, Massachusetts Medical Society, United States (Jan. 2003).
Houghten, R.A., et al., "The Use of Synthetic Peptide Combinatorial Libraries for the Identification of Bioactive Peptides," Biotechniques 13(3):412-421, Informa Healthcare USA, England (Sep. 1992).
Hsu, I.C., et al., "Detection of DNA Point Mutations with DNA Mismatch Repair Enzymes," Carcinogenesis 15(8):1657-1662, Irl Press, England (Aug. 1994).
Huston, J.S., et al., "Protein Engineering of Antibody Binding Sites: Recovery of Specific Activity in an Anti-digoxin Single-chain Fv Analogue Produced in Escherichia coli," Proceedings of the National Academy of Sciences USA 85(16):5879-5883, National Academy of Sciences, United States (Aug. 1988).
Huston, J.S., et al., "Protein Engineering of Single-chain Fv Analogs and Fusion Proteins," Methods in Enzymology 203:46-88, Academic Press, United States (1991).
Hybridization with Radioactive Probes, Current Protocols in Molecular Biology, John Wiley & Sons, N.Y. 6.3.1-6.3.6 (1989).
Hyrup, B. and Nielsen, P.E., "Peptide Nucleic Acids (PNA): Synthesis, Properties and Potential Applications," Bioorganic & Medicinal Chemistry 4(1):5-23, Elsevier Science, England (Jan. 1996).
Ill, C.R., et al., "Design and Construction of a Hybrid Immunoglobulin Domain With Properties of Both Heavy and Light Chain Variable Regions," Protein Engineering 10(8):949-957, IRL Press, England (1997).
Inoue, H., et al., "Sequence-dependent Hydrolysis of RNA using Modified Oligonucleotide Splints and RNase H," FEBS letters 215(2):327-330, Elsevier Science B.V, Netherlands (May 1987).
Inoue, H., et al., "Synthesis and Hybridization Studies on Two Complementary Nona(2'-O-Methyl)Ribonucleotides," Nucleic Acids Research 15(15):6131-6148, Oxford University Press, England (Aug. 1987).
International Search Report for International Application No. PCT/EP2012/074092, European Patent Office, Rijswijk, mailed on Jun. 20, 2013, 5 pages.
International Search Report for International Application No. PCT/EP2015/066501, European Patent Office, Rijswijk, mailed on Oct. 12, 2015, 6 pages.
Iwabuchi, K., et al., "Use of the two-hybrid system to identify the domain of p53 involved in oligomerization," Oncogene 8(6):1693-1696, (1993).
Jespers, L.S., et al., "Guiding the Selection of Human Antibodies from Phage Display Repertoires to a Single Epitope of an Antigen," Bio/technology 12(9):899-903, Wiley-Blackwell, United States (1994).
Jezek, J., et al., "Viscosity of Concentrate Therapeutic Protein Compositions," Advanced Drug Delivery Reviews 63(13):1107-1117, Elsevier Science Publishers, Netherlands (2011).
Jobling, M.G. and Holmes, R.K., "Analysis of Structure and Function of the B Subunit of Cholera Toxin by the Use of Site-directed Mutagenesis," Molecular Microbiology 5(7):1755-1767, Blackwell Scientific Publications, England (Jul. 1991).
Kabat, E.A., et al., "Sequences of Proteins of Immunological Interest," 5th Edition, U.S. Department of Public Health and Human Services, Public Health Service, NIH publication no 91-3242, National Institutes of Health, Bethesda (1991).
Kabsch, W., "Integration, Scaling, Space-group Assignment and Post-refinement," Acta Crystallographica, Section D, Biological Crystallography 66(Pt 2):133-144, Wiley-Blackwell, United States (2010).
Kamerzell, T.J., et al., "Protein-excipient Interactions: Mechanisms and Biophysical Characterization Applied to Protein Formulation Development," Advanced Drug Delivery Reviews 63(13):1118-1159, Elsevier Science Publishers, Netherlands (2011).
Kanai, S., et al., "Reversible Self-association of a Concentrated Monoclonal Antibody Solution Mediated by Fab-fab Interaction That Impacts Solution Viscosity," Journal of Pharmaceutical Sciences 97(10):4219-4227, Elsevier, United States (2008).
Kang, D., et al. "A Peptidoglycan Recognition Protein in Innate Immunity Conserved From Insects to Humans," Proceedings of the National Academy of Sciences of the United States of America 95(17):10078-10082, National Academy of Sciences, United States (Aug. 1998).
Karttunen, J. and Shastri, N., "MEasurement of Ligand-induced Activation in Single Viable T Cells Using the IacZ Reporter Gene," Proceedings of the National Academy of Sciences of the United States of America 88(9):3972-3976, National Academy of Sciences, United States (1991).
Katsuura, M., et al., "CD48 Expression on Leukocytes in Infectious Diseases: Flow Cytometric Analysis of Surface Antigen," Acta Paediatrica Japonica 40(6):580-585, Blackwell Scientific, Australia (Dec. 1998).
Kaufman, R.J., et al., "Translational Efficiency of Polycistronic mRNAs and Their Utilization to Express Heterologous Genes in Mammalian Cells," The EMBO Journal 6(1):187-195, Wiley Blackwell, England (Jan. 1987).
Keane, J., et al., "Tuberculosis Associated With Infliximab, a Tumor Necrosis Factor Alpha-neutralizing Agent," The New England Journal of Medicine 345(15):1098-1104, Massachusetts Medical Society, United States (Oct. 2001).
Keen, J., et al., "Rapid Detection of Single Base Mismatches as Heteroduplexes on Hydrolink Gels," Trends in Genetics 7(1):5, Elsevier Trends Journals, England (Jan. 1991).
Kelker, M.S., et al., "Crystal Structure of Human Triggering Receptor Expressed on Myeloid Cells 1 (TREM-1) at 1.47 A," Journal of Molecular Biology 342(4):1237-1248, Elsevier, England (2004).
Kessel, M. and Gruss, P., "Murine Developmental Control Genes," Science 249(4967):374-379, American Association for the Advancement of Science, United States (Jul. 1990).
Ketchem, R.R., et al., "Mitigation of Monoclonal Antibody Viscosity by Modification of Protein Surface Charge," American Chemical Society, vol. 243, p. 1 (Mar. 2012) XP008171180, Retrieve from the internet <URL: http://abstracts.acs.org/chem/243nm/program/view.php?obj_id=122153&terms=>.
Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).
Kharitonenkov, A., et al., "FGF-21 as a Novel Metabolic Regulator," The Journal of Clincal Investigation 115(6):1627-1635, American Society for Clincal Investigation, United States (Jun. 2005).
Kharitonenkov, A., et al., "The Metabolic State of Diabetic Monkeys Is Regulated by Fibroblast Growth Factor-21," Endocrinology 148(2):774-781, Oxford University Press, United States (Feb. 2007).
Kiem, H.P., et al., "Retrovirus-mediated Gene Transduction Into Canine Peripheral Blood Repopulating Cells," Blood 83(6):1467-1473, American Society of Hematology, United States (Mar. 1994).
Knappik, A. and Pluckthun, A., "An Improved Affinity Tag Based on the FLAG Peptide for the Detection and Purification of Recombinant Antibody Fragments," Biotechniques 17(4):754-761, Informa Healthcare USA, England (Oct. 1994).
Knudsen, L.B., "Glucagon-like Peptide-1: The Basis of a New Class of Treatment for Type 2 Diabetes," Journal of Medicinal Chemistry 47(17):4128-4134, American Chemical Society, United States (Aug. 2004).
Kohler, G., "Immunoglobulin Chain Loss in Hybridoma Lines," Proceedings of the National Academy of Sciences USA 77(4):2197-2199, National Academy of Sciences, United States (Apr. 1980).
Koller, B.H. and Smithies, O., "Inactivating the beta 2-Microglobulin Locus in Mouse Embryonic Stem Cells by Homologous Recombination," Proceedings of the National Academy of Sciences USA 86(22):8932-8935, National Academy of Sciences, United States (Nov. 1989).

(56) References Cited

OTHER PUBLICATIONS

Kozal, M.J., et al., "Extensive Polymorphisms Observed in HIV-1 Clade B Protease Gene Using High-density Oligonucleotide Arrays," Nature Medicine 2(7):753-759, Nature Publishing Company, United States (Jul. 1996).

Kozarsky, K.F. and Wilson, J.M., "Gene Therapy: Adenovirus Vectors," Current Opinion in Genetics & Development 3(3):499-503, Elsevier, England (Jun. 1993).

Kruse, C.A., et al., "Characterization of a Continuous Human Glioma Cell Line DBTRG-05MG: Growth Kinetics, Karyotype, Receptor Expression, and Tumor Suppressor Gene Analyses," In Vitro Cellular & Development Biology 28A(9-10):609-614, Tissue Culture Association, United States (Sep.-Oct. 1992).

Kuai, J., et al., "TREM-1 Expression is Increased in the Synovium of Rheumatoid Arthritis Patients and Induces the Expression of Pro-inflammatory Cytokines," Rheumatology 48(11):1352-1358, Mercury International, England (2009).

Kubagawa, H., et al., "Biochemical Nature and Cellular Distribution of the Paired Immunoglobulin-like Receptors, PIR-A and PIR-B," The Journal of Experimental Medicine 189(2):309-318, Rockefeller University Press, United States (Jan. 1999).

Kunkel, T.A., et al., "Rapid and Efficient Site-specific Mutagenesis Without Phenotypic Selection," Methods in Enzymology 154:367-382, Academic Press, United States (1987).

Kurjan, J. and Herskowitz, I., "Structure of a Yeast Pheromone Gene (MF Alpha): A Putative Alpha-factor Precursor Contains Four Tandem of Mature Alpha-factor," Cell 30(3):933-943, Cell Press, United States (Oct. 1982).

Kwoh, D.Y., et al., "Transcription-Base Amplification System and Detection of Amplified Human Immunodeficiency Virus Type 1 with a Bead-Based Sandwich Hybridization Format," Proceedings of the National Academy of Sciences of the United States of America 86(4):1173-1177, National Academy of Sciences, United States (1989).

Lakso, M., et al., "Targeted Oncogene Activation by Site-specific Recombination in Transgenic Mice," Proceedings of the National Academy of Sciences 89(14):6232-6236, National Academy of Sciences, United States (Jul. 1992).

Lam, K.S., "Application of Combinatorial Library Methods in Cancer Research and Drug Discovery," Anticancer Drug Design 12(3):145-67, (1997).

Lam, K.S., et al., "A New Type of Synthetic Peptide Library for Identifying Ligand-Binding Activity," Nature 354:82-84, Nature Publishing Group, United States (1991).

Landegren, U., et al., "A Ligase-mediated Gene Detection Technique," Science 241(4869):1077-1080, American Association for the Advancement of Science, United States (Aug. 1988).

Lane, P., et al., "CD40 Ligand-independent B Cell Activation Revealed by CD40 Ligan-deficient T Cell Clones: Evidence for Distinct Activation Requirements for Antibody Formation and B Cell Proliferation," European Journal of Immunology 25(6):1788-1793, Wiley-VCH, Germany (Jun. 1995).

Lanier, L.L., et al., "Immunoreceptor DAP12 Bearing a Tyrosine-based Activation Motif Is Involved in Activating NK Cells," Nature 391(6668): 703-707, Nature Publishing Group, England (Feb. 1998).

Lanier, L.L., "NK Cell Receptors," Annual Review of Immunology 16:359-393, Annual Reviews Inc., United States (1998).

Lantz, M., et al., "Characterization in Vitro of a Human Tumor Necrosis Factor-binding Protein. A Soluble Form of a Tumor Necrosis Factor Receptor," The Journal of Clinical Investigation 86(5):1396-1402, American Society for Clinical Investigation, United States (Nov. 1990).

Larin, S.S., et al., "Immunotherapy with Autologous Tumor Cells Engineered to Secrete Tag7/PGRP, an Innate Immunity Recognition Molecule," Gene Medicine 6(7):798-808, John Wiley & Sons, England (Jul. 2004).

Lemaitre, M., et al., "Specific Antiviral Activity of a Poly (L-Lysine)-Conjugated Oligodeoxyribonucleotide Sequence Complementary to Vesicular Stomatitis Virus N Protein mRNA Initiation Site," Proceedings of the National Academy of Sciences 84(3):648-652, National Academy of Science, United States (Feb. 1987).

Letsinger, R.L., et al., "Cholesteryl-conjugated Oligonucleotides: Synthesis, Properties, and activity as Inhibitors of Replication of Human Immunodeficiency Virus in Cell Culture," Proceedings of the National Academy of Sciences USA 86(17):6553-6556, National Academy of Science, United States (Sep. 1989).

Li, E., et al., "Targeted Mutation of the DNA Methyltransferase Gene Results in Embryonic Lethality," Cell 69(6):915-926, Cell Press, United States (Jun. 1992).

Liu, J., et al., "Reversible Self-association Increases the Viscosity of a Concentrated Monoclonal Antibody in Aqueous Solution," Journal of Pharmaceutical Sciences 94(9):1928-1940, Elsevier, United States (2005).

Lizardi, M.P., et al., "Exponential Amplification of Recombinant—RNA Hybridization Probes," Nature Biotechnology 6:1197-1202 (1988).

Loeffler, J.P., et al., "Gene Transfer Into Primary and Established Mammalian Cell Lines With Lipopolyamine-coated DNA," Methods in Enzymology 217:599-618, Academic Press, United States (1993).

Lolis, E. and Bucala, R., "Therapeutic Approaches to Innate Immunity: Severe Sepsis and Septic Shock," Nature Reviews: Drug Discovery 2(8):635-645, Nature Pub, Group, England (Aug. 2003).

Lonberg, N. and Huszar, D., "Human Antibodies from Transgenic Mice," International Reviews of Immunology 13(1):65-93, Informa Healthcare, England (1995).

Lowy, I., et al., "Isolation of Transforming DNA: Cloning the Hamster aprt Gene," Cell 22(3):817-823, Cell Press, United States (Dec. 1980).

LS Bio/LifeSpan BioSciences, Inc., Pglyrp1/ pgrp antibody (ls-c579), accessed at http://www.lsbio.com/Antibodies/PGLYRP1-PGRP-Antibody-LS-C579/2801, Accessed on Jun. 12, 2014.

LS Bio/LifeSpan BioSciences, Inc., Pglyrp1 1 pgrp antibody (ls-c38137), accessed at http://www.lsbio .com/Antibodies/PGLYRP1-PGRP-Antibody-LS-C38137/37645, Accessed on Aug. 1, 2014.

LS Bio/LifeSpan BioSciences, Inc., Pglyrp1/ pgrp antibody (ls-b4940), accessed at http://www.lsbio.com/Antibodies/PGLYRP1-PGRP-Antibody-LS-B4940/128350.

LS Bio/LifeSpan BioSciences, Inc., Pglyrp1/ pgrp antibody (ls-c578), accessed at http://www.lsbio .com/Antibodies/PGLYRP1-PGRP-Antibody-LS-C578/2800, Accessed on Jun. 12, 2014.

Lucklow, V.A., et al., "High Level Expression of Nonfused Foreign Genes With Autographa California Nuclear Polyhedrosis Virus Expression Vectors," Virology 170(1):31-39 (1989).

MacCallum, R.M., et al., "Antibody-antigen Interactions: Contact Analysis and Binding Site Topography," Journal of Molecular Biology 262(5):732-745, Academic Press, England (Oct. 1996).

Madura, K., et al., "N-Recognin/Ubc2 Interactions in Then-End Rule Pathway," Journal of Biological Chemistry 17:5973-5988 (1993).

Madura, K., et al., "N-recognin/Ubc2 interactions in the N-end rule pathway," The Journal of Biological Chemistry 268(16):12046-12054, The American Society for Biochemistry and Molecular Biology, Inc., United States (1993).

Mag, M., et al., "Synthesis and Selective Cleavage of Oligodeoxyribonucleotides Containing Non-chiral Internucleotide Phosphoramidate Linkages," Nucleic Acids Research 17(15):5973-5988 (Aug. 1989).

Maher, L.J., et al., "DNA Triple-helix Formation: an Approach to Artificial Gene Repressors?," BioEssays 14(12):807-815, Wiley, United States (Dec. 1992).

Malaviya, R., et al., "Mast Cell Modulation of Neutrophil Influx and Bacterial Clearance at Sites of Infection Through TNF-alpha," Nature 381(6577):77-80, Nature Publishing Group, England (May 1996).

Mandell, J.G., et al., "Identification of Protein-protein Interfaces by Decreased Amide Proton Solvent Accessibility," Proceedings of the National Academy of Sciences of the United States of America 95(25):14705-14710, National Academy of Sciences, United States (1998).

(56) References Cited

OTHER PUBLICATIONS

Mansart, A., et al., "Hemodynamic Effects of Early Versus Late Glucocorticosteroid Administration in Experimental Septic Shock," Shock 19(1):38-44, Lippincott Williams & Wilkins, United states (Jan. 2003).

Mastrangeli, A., et al., "Diversity of Airway Epithelial Cell Targets for In Vivo Recombinant Adenovirus-Mediated Gene Transfer," Journal of Clinical Investigation 91(1):225-234, American Society for Clinical Investigation, United States (Jan. 1993).

Maxam, A.M. and Gilbert, W., "A New Method for Sequencing DNA," Proceedings of the National Academy of Sciences USA 74(2):560-564, National Academy of Sciences, United States (Feb. 1977).

McNamara, M.J., et al., "Interleukin-1 Receptor Antibody (Il-1rab) Protection and Treatment Against Lethal Endotoxemia in Mice," Journal of Surgical Research 54(4):316-321, Academic Press, United States (Apr. 1993).

Medzhitov, R., et al., "Innate Immunity," The New England Journal of Medicine 343(5):338-344, Massachusetts Medical Society, United States (Aug. 2000).

Micanovic, R., et al., "Different Roles of N- and C- Termini in the Functional Activity of FGF21," Journal of Cellular Physiology 219(2):227-234, Wiley-Liss, United States (May 2009).

Michael, S.F., et al., "Mutagenesis by Incorporation of a Phosphorylated Oligo During PCR Amplification," BioTechniques 16(3):410-412, Informa Healthcare USA, England (Mar. 1994).

Miller, A.D., et al., "Use of Retroviral Vectors for Gene Transfer and Expression," Methods in Enzymology 217:581-599, Academic Press, United States (1993).

Mohamadzadeh, M., et al., "Activation of Triggering Receptor Expressed on Myeloid Cells-1 on Human Neutrophils by Marbug and Ebola Viruses," Journal of Virology 80(14):7235-7244, American Society For Microbiology, United States (Jul. 2006).

Molloy, E.J., "Triggering Receptor Expressed on Myeloid Cells (TREM) Family and the Application of its Antagonists," Recent Patents on Anti-infective Drug Discovery 4(1):51-56, Bentham Science Publishers, Netherlands (2009).

Morgan, R.A. and Anderson, W.F., "Human Gene Therapy," Annual Review of Biochemistry 62:191-217, Annual Reviews, United States (1993).

Mori, S.I., et al., "A Novel Amino Acid Substitution at the Receptor-binding Site on the Hemagglutinin of H3N2 Influenza a Viruses Isolated From 6 Cases With Acute Encephalopathy During the 1997-1998 Season in Tokyo," Archives of Virology 144(1):147-155, Springer-Verlag, Austria (1999).

Morrison, D.C., et al., "Endotoxins and Disease Mechanisms," Annual Review of Medicine 38:417-432, Annual Reviews, United States (1987).

Morrison, S.L., "Transfectomas Provide Novel Chimeric Antibodies," Science 229(4719):1202-1207, Association for the Advancement of Science, United States (Sep. 1985).

Mulligan, R.C. and Berg, P., "Selection for Animal Cells that Express the *Escherichia coli* Gene Coding for Xanthine-guanine Phosphoribosyltransferase," Proceedings of the National Academy of Sciences USA 78(4):2072-2076, National Academy of Sciences, United States (Apr. 1981).

Mulligan, R.C., "The Basic Science of Gene Therapy," Science 260(5110):926-932, American Association for the Advancement of Science, United States (1993).

Mullinax, R.L., et al., "Expression of a Heterodimeric Fab Antibody Protein in One Cloning Step," BioTechniques 12(6):864-869, Informa Healthcare, England (1992).

Murakami, Y., et al., "Intervention of an Inflammation Amplifier, Triggering Receptor Expressed on Myeloid Cells 1, for Treatment of Autoimmune Arthritis," Arthritis and Rheumatism 60(6):1615-1623, Wiley-Blackwell, United States (Jun. 2009).

Murshudov, G.N., et al., "Refinement of Macromolecular Structures by the Maximum-likelihood Method," Acta Crystallographica, Section D, Biological Crystallography 53(Pt 3):240-255, Wiley-Blackwell, United States (1997).

Myers, R.M., et al., "Detection of Single Base Substitutions by Ribonuclease Cleavage at Mismatches in RNA:DNA Duplexes," Science 230(4731):1242-1246, American Association for the Advancement of Science, United States (Dec. 1985).

Myers, R.M., et al., "Detection of Single Base Substitutions in Total Genomic DNA," Nature 313(6002):495-498, Nature Publishing Group, England (Feb. 1985).

Nakajima, H., et al., "2B4: an Nk Cell Activating Receptor With Unique Specificity and Signal Transduction Mechanism," Human Immunology 61(1):39-43, Elsevier/North-Holland, United States (Jan. 2000).

Nakajima, H., et al., "Cutting Edge: Human Myeloid Cells Express an Activating Ilt Receptor (ILT1) That Associates With Fc Receptor Gamma-chain," Journal of Immunology 162(1):5-8, American Association of Immunologists, United States (Jan. 1999).

Nakazawa, H., et al., "UV and Skin Cancer: Specific P53 Gene Mutation in Normal Skin as a Biologically Relevant Exposure Measurement," Proceedings of the National Academy of Sciences USA 91(1):360-364 (Jan. 1994).

Naramura, M., et al., "Mechanisms of Cellular Cytotoxicity Mediated by a Recombinant Antibody-IL2 Fusion Protein Against Human Melanoma Cells," Immunology Letters 39(1):91-99 (Dec. 1993).

Nathan, C. and Ding, A., "TREM-1: A New Regulator of Innate Immunity in Sepsis Syndrome," Nature Medicine 7(5):530-532, Nature Publishing Company, United States (May 2001).

Nauck, M.A. and Meier, J.J., "Glucagon-like Peptide 1 and Its Derivatives in the Treatment of Diabetes," Regulatory Peptides 128(2):135-148, Elsevier/North Holland, Netherlands (Jun. 2005).

Nederman, T., et al., "An in Vitro Bioassay for Quantitation of Human Interferons by Measurements of Antiproliferative Activity on a Continuous Human Lymphoma Cell Line," Biologicals 18(1):29-34, Academic Press, England (Jan. 1990).

Ngo, J.T., et al., "The Protein Folding Problem and Tertiary Structure Prediction, Chapter 14: Computational Complexity PRotein Structure Prediction, and the Levinthal Paradox," 492-495 (Mar. 1995).

Nicoletti, I., et al., "A Rapid and Simple Method for Measuring Thymocyte Apoptosis by Propidium Iodide Staining and Flow Cytometry," Journal of Immunological Methods 139(2):271-279, Elsevier, Netherlands (Jun. 1991).

O'Gorman, S., et al., "Recombinase-Mediated Gene Activation and Site-specific Integration in Mammalian Cells," Science 251(4999):1351-1355, American Association for the Advancement of Science, United States (Mar. 1991).

O'Hare, K., et al., "Transformation of Mouse Fibroblasts to Methotrexate Resistance by a Recombinant Plasmid Expressing a Prokaryotic Dihydrofolate Reductase," Proceedings of the National Academy of Sciences USA 78(3):1527-1531, National Academy of Sciences, United States (Mar. 1981).

Ohlsson, K., et al., "Interleukin-1 Receptor Antagonist Reduces Mortality from Endotoxin Shock," Nature 348(6301):550-552, Nature Publishing Group, England (Dec. 1990).

Oi, V.T. and Morrison, S.L., "Chimeric Antibodies," BioTechniques 4(3):214-221 (1986).

Oishi, K., et al., "Inhibition of Neutrophil Apoptosis by Antioxidants in Culture Medium," Scandinavian Journal of Immunology 45(1):21-27, Blackwell Scientific Publications, England (Jan. 1997).

Oliveira, J.S., et al., "Fungal Infections in Marrow Transplant Recipients Under Antifungal Prophylaxis With Fluconazol," Brazilian Journal of Medical and Biological Research 35(7):789-798, Brazilian Association of Scientific Dissemination, Brazil (Jul. 2002).

Olopade, O.I., et al., "Molecular Analysis of Deletions of the Short Arm of Chromosome 9 in Human Gliomas," Cancer Research 52(9):2523-2529, American Association for Cancer Research, United States (May 1992).

Orita, M., et al., "Detection of Polymorphisms of Human DNA by Gel Electrophoresis as Single-strand Conformation Polymorphisms," Proceedings of the National Academy of Sciences USA 86(8):2766-2770, National Academy of Sciences, United States (Apr. 1989).

Osanai, A., et al., "Mouse Peptidoglycan Recognition Protein PGLYRP-1 Plays a Role in the Host Innate Immune Response Against Listeria

(56) References Cited

OTHER PUBLICATIONS

Monocytogenes Infection," Journal of Infection and Immunity 79(2):858-866, American Society For Microbiology, United States (Feb. 2011), XP055060881.
Owerbach, D., et al., "Genetics of the Large, External, Transformation-sensitive(LETS) Protein: Assignment of a Gene Coding for Expression of Lets to Human Chromosome 8," Proceedings of the National Academy of Sciences USA 75(11):5640-5644, National Academy of Sciences, United States (Nov. 1978).
Padlan, E.A., "A Possible Procedure for Reducing the Immunogenicity of Antibody Variable Domains While Preserving their Ligand-binding Properties," Molecular Immunology 28(4-5):489-498, Pergamon Press., England (Apr. 1991).
Pajunen, L., et al., "Assignment of the Gene Coding for Both the Beta-subunit of Prolyl 4-hydroxylase and the Enzyme Disulfide Isomerase to Human Chromosome Region 17p11-qter," Cytogenetics and Cell Genetics 47(1-2):37-41, Karger, Switzerland (1988).
Pant, S.,D., et al., "Bovine PGLYRP1 Polymorphisms and their Association with Resistance to Mycobacterium Avium ssp. Paratuberculosis," Animal Genetics 42(4):354-360, Wiley-Blackwell, England (Aug. 2011).
Perry-O'Keefe, H., et al., "Peptide Nucleic Acid Pre-gel Hybridization: an Alternative to Southern Hybridization," Proceedings of the National Academy of Sciences of the United States of America 93(25):14670-14675, National Academy of Sciences, United States (1996).
Persic, L., et al., "An Integrated Vector System for the Eukaryotic Expression of Antibodies or Their Fragments Affer Selection From Phage Display Libraries," Gene 187(1):9-18, Elsevier/North-Holland, Netherlands (1997).
Peschon, J.J., et al., "TNF Receptor-Deficient Mice Reveal Divergent Roles for P55 and P75 in Several Models of Inflammation," Journal of Immunology 160(2):943-952, American Association of Immunologists, United States (Jan. 1998 ).
Petersen, K.H., et al., "A PNA-DNA Linker Synthesis of N-((4,4'-dimethoxytrityloxy)ethyl)- N-(Thymin-1-ylacetyl)glycine," Bioorganic & Medicinal Chemistry Letters 5:1119-1124 (1995).
Pfeffer, K., et al., "Mice Deficient for the 55 Kd Tumor Necrosis Factor Receptor are Resistant to Endotoxic Shock, Yet Succumb to L. Monocytogenes Infection," Cell 73(3):457-467, Cell Press,United States (May 1993).
Phua, J., et al., "Soluble Triggering Receptor Expressed on Myeloid Cells-1 in Acute Respiratory Infections," The European Respiratory Journal 28(4):695-702, European Respiratory Society, England (Oct. 2006).
Pinkert, C.A., et al., "An Albumin Enhancer Located 10 Kb Upstream Functions Along With Its Promoter to Direct Efficient, Liver-specific Expression in Transgenic Mice," Genes & Development 1(3):268-276, Cold Spring Harbor Laboratory Press, United States (May 1987).
Pittelkow, M.R. and Scott, R.E., "New Techniques for the in Vitro Culture of Human Skin Keratinocytes and Perspectives on Their Use for Grafting of Patients With Extensive Burns," Mayo Clinic Proceedings 61(10):771-777, Elsevier, England (Oct. 1986).
Potterton, E., et al., "A Graphical User Interface to the CCP4 Program Suite," Acta Crystallographic, Section D, Biological Crystallography 59(Pt 7):1131-1137, Wiley-Blackwell, United States (2003).
Poukoulidou, T., et al., "TREM-1 Expression on Neutrophils and Monocytes of Septic Patients: Relation to the Underlying Infection and the Implicate Pathogen," BMC Infectious Diseases 11(1): 8 pages, BioMed Central, England (Nov. 2011).
Prosser, J., "Detecting Single-base Mutations," Trends in Biotechnology 11(6):238-246, Elsevier Science Publishers, England (Jun. 1993).
Proudfoot, N.J., "Transcriptional Interference and Termination Between Duplicated Alpha-globin Gene Constructs Suggests a Novel Mechanism for Gene Regulation," Nature 322(6079):562-565, Nature Publishing Group, England (1986).

Purified anti-human CD354 TREM-1 Antibody, accessed at, https//www.biolegend.com/enus/products/purified-anti-human-cd354-trem-1-antibody-2826, last accessed on Jun. 12, 2018, 3 pages.
Queen, C. and Baltimore, D., "Immunoglobulin Gene Transcription Is Activated by Downstream Sequence Elements," Cell 33(3):741-748, Cell Press, United States (Jul. 1983).
Radaev, S., et al., "Crystal Structure of the Human Myeloid Cell Activating Receptor TREM-1," Structure 11(12):1527-1535, Cell Press, United States (Dec. 2003).
Radany, E.H., et al., "Directed Establishment of Rat Brain Cell Lines With the Phenotypic Characteristics of Type 1 Astrocytes," Proceedings of the National Academy of Sciences of the United States of America 89(14):6467-6471, National Academy of Sciences, United States (Jul. 1992).
Ramanathan, B., et al., "Cloning of Porcine Triggering Receptor Expressed on Myeloid Cells-1 (TREM-1) and its Induction by Lipopolysaccharide, Peptidoglycan, and Salmonella Enterica Serovar Typhimurium Infection," Developmental and Comparative Immunology 29(1):1-7, Elsevier Science, United States (2005).
R&D Systems, "Human TREM-1 Antibody," accessed at http:www.mdsystems.com/Products/MAB1278 accessed on Nov. 27, 2012.
R&D Systems: "Human TREM-1 Antibody," Retrieved from the internet<URL: http://www.mdsystems.com/Products/MAB1278> on Oct. 26, 2010, p. 1, XP002688074.
Redl, H., et al., "Animal Models as the Basis of Pharmacologic Intervention in Trauma and Sepsis Patients," World Journal of Surgery 20(4):487-492, Springer International, United States (May 1996).
Rheinwald, J.G., "Chapter 15 Serial Cultivation of Normal Human Epidermal Keratinocytes," Methods in Cell Biology 21A:229-254, Academic Press, United States (1980).
Riechmann, L., et al., "Reshaping Human Antibodies for Therapy," Nature 332(6162):323-327, Nature Publishing Group, United States (Mar. 1988).
Riedemann, N.C., et al., "Novel Strategies for the Treatment of Sepsis," Nature Medicine 9(5):517-524, Nature Publishing Company, United States (May 2003).
Roguska, M.A., et al., "Humanization of Murine Monoclonal Antibodies Through Variable Domain Resurfacing," Proceedings of the National Academy of Sciences USA 91(3):969-973, National Academy of Sciences, United States (Feb. 1994).
Rosenbaum, V. and Riesner, D., "Temperature-gradient Gel Electrophoresis, Thermodynamic Analysis of Nucleic Acids and Proteins in Purified Form and in Cellular Extracts," Biophysical Chemistry 26(2-3):235-246, Elsevier Science B.V, Netherlands (May 1987).
Rosenberg, H.F, and Gallin, J.I., "Inflammation," In Fundamental Immunology, 4th Ed. W. E. Paul, ed., Chapter 32, p. 1051-1058, Lippincott-Raven Publishers, 1999.
Rosenfeld, M.A., et al., "Adenovirus-mediated Transfer of a Recombinant alpha 1-antitrypsin Gene to the Lung Epithelium in Vivo," Science 252(5004):431-434, American Association for the Advancement of Science, United States (Apr. 1991).
Rosenfeld, M.A., et al., "In Vivo Transfer of the Human Cystic Fibrosis Transmembrane Conductance Regulator Gene to the Airway Epithelium," Cell 68(1):143-155, Cell Press, United States (Jan. 1992).
Rothe, J., et al., "Mice Lacking the Tumour Necrosis Factor Receptor 1 are Resistant to TNF-mediated Toxicity but Highly Susceptible to Infection by Listeria Monocytogenes," Nature 364(6440):798-802, Nature Publishing Group, England (Aug. 1993).
Royet, J., et al., "Peptidoglycan Recognition Proteins: Modulators of the Microbiome and Inflammation," Nature Reviews Immunology 11(12):837-851, Nature Pub. Group, England (Nov. 2011).
Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).
Saha, S., et al, "Peptidoglycan Recognition Proteins Protect Mice from Experimental Colitis by Promoting Normal Gut Flora and Preventing Induction of Interferon-Gamma," Cell Host & Microbe 8(2):147-162, Cell Press, United States (Aug. 2010).

(56) References Cited

OTHER PUBLICATIONS

Saha, S., et al, "PGLYRP-2 and Nod2 are both Required for Peptidoglycan-Induced Arthritis and Local Inflammation," Cell Host & Microbe 5(2):137-150, Cell Press, United States (Feb. 2009).
Saiki, R.K., et al., "Analysis of Enzymatically Amplified Beta-globin and HLA-DQ Alpha DNA With Allele-specific Oligonucleotide Probes," Nature 324(6093):163-166, Nature Publishing Group, England (Nov. 1986).
Saiki, R.K., et al., "Genetic Analysis of Amplified DNA With Immobilized Sequence-specific Oligonucleotide Probes," Proceedings of the National Academy of Sciences of the United States of America 86(16):6230-6234, National Academy of Sciences, United States (Aug. 1989).
Saleeba, J.A. and Cotton, R.G., "Chemical Cleavage of Mismatch to Detect Mutations," Methods in Enzymology 217:286-295, Academic Press, United States (1993).
Sallusto, F., et al., "Efficient Presentation of Soluble Antigen by Cultured Human Dendritic Cells Is Maintained by Granulocyte/macrophage Colony-stimulating Factor Plus Interleukin 4 and Downregulated by Tumor Necrosis Factor Alpha," The Journal of Experimental Medicine 179(4):1109-1118, Rockefeller University Press, United States (1994).
Salmons, B. and Gunzburg, W.H., "Targeting of Retroviral Vectors for Gene Therapy," Human Gene Therapy 4(2):129-141, Liebert, United States (Apr. 1993).
Sanger, F., et al., "DNA Sequencing With Chain-terminating Inhibitors," Proceedings of the National Academy of Sciences of the United States of America 74(12):5463-5467, National Academy of Sciences, United States (Dec. 1977).
Santerre, R.F., et al., "Expression of Prokaryotic Genes for Hygromycin B and G418 Resistance as Dominant-selection Markers in Mouse L Cells," Gene 30(1-3):147-156, Elsevier/North-Holland, Netherlands (Oct. 1984).
Sawai, H., et al., "Direct Production of the Fab Fragment Derived From the Sperm Immobilizing Antibody Using Polymerase Chain Reaction and cDNA Expression Vectors," American Journal of reproductive immunology 34(1):26-34, Wiley-Blackwell, Denmark (1995).
Schenk, M., et al., "TREM-1-expressing Intestinal Macrophages Crucially Amplify Chronic Inflammation in Experimental Colitis and Inflammatory Bowel Diseases," The Journal of Clinical Investigation 117(10):3097-3106, American Society for Clinical Investigation, United States (2007).
Schultz, L.D., et al., "Expression and Secretion in Yeast of a 400-kDa Envelope Glycoprotein Derived From Epstein-Barr Virus," Gene 54(1):113-123, Elsevier/North-Holland, Netherlands (1987).
Scott, J.K. and Smith, G.P., "Searching for peptide ligands with an epitope library," Science 249(4967):386-390, American Association for the Advancement of Science, United States (1990).
Seed, B., "An LFA-3 cDNA Encodes a Phospholipid-linked Membrane Protein Homologous to its Receptor CD2," Nature 329(6142):840-842, Nature Publishing Group, England (Oct. 1987).
Sharif, O. and Knapp, S., "From Expression to Signaling: Roles of TREM-1 and TREM-2 in Innate Immunity and Bacterial Infection," Immunobiology 213(9-10):701-713, Elsevier, Netherlands (2008).
Shire, S.J., et al., "Challenges in the Development of High Protein Concentration Formulations," Journal of Pharmaceutical Sciences 93(6):1390-1402, Elsevier, United States (2004).
Shu, L., et al., "Secretion of a Single-gene-encoded Immunoglobulin From Myeloma Cells," Proceedings of the National Academy of Science of the USA 90(17):7995-7999, National Academy of Sciences, United States (1993).
Skerra, A. and Pluckthun, A., "Assembly of a Functional Immunoglobulin Fv Fragment in *Escherichia coli*," Science 240(4855):1038-1041, Association for the Advancement of Science, United States (May 1988).

Skolnick, "From Genes to Protein Stucture and Function: Novel Applications of Computational Approaches in the Genomic era," Trends in Biotechnology 18:34-39, Elsevier Science Publishers, London (Jan. 2000).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (Jul. 1988).
Smith, G.E., et al., "Production of Human Beta Interferon in Insect Cells Infected With a Baculovirus Expression Vector," Molecular and Cellular Biology 3(12):2156-2165, American Society for Microbiology, United States (Dec. 1983).
Smith, T.F. and Zhang, X., "The Challenges of Genome Sequence Annotation Or "The Devil is in the Details"," Nature Biotechnology 15(12):1222-1223, Nature America Publishing, United States (Nov. 1997).
Tomar, D.S., et al., "Molecular basis of high viscosity in concentrated antibody solutions: Strategies for high concentration drug product development," MAbs 8(2):216-28, Taylor Francis, United States (2016).
Springer, T.A., "Traffic Signals for Lymphocyte Recirculation and Leukocyte Emigration: The Multistep Paradigm," Cell 76(2):301-314, Cell Press, United States (Jan. 1994).
Standen, J. and Bihari, D., "Septic Shock," The New England Journal of Medicine 343:447-448 (Aug. 2010).
Steiner, H., , "Peptidoglycan Recognition Proteins: On and Off Switches for Innate Immunity," Immunological Reviews 198:83-96, Blackwell, England (Apr. 2004).
Stemple, D.L. and Anderson, D.J., "Isolation of a Stem Cell for Neurons and Glia From the Mammalian Neural Crest," Cell 71(6):973-985, Cell Press, United States (Dec. 1992).
Stone, R., "Search for Sepsis Drugs Goes on Despite Past Failures," Science 264(5157):365-367, American Association for the Advancement of Science, United States (Apr. 1994).
Studnicka, G.M., et al., "Human-Engineered Monoclonal Antibodies Retain Full Specific Binding Activity By Preserving Non-CDR Complementarity-Modulating Residues," Protein Engineering 7(6):805-814, Oxford University Press, England (1994).
Sugimoto, T., et al., "Determination of Cell Surface Membrane Antigens Common to Both Human Neuroblastoma and Leukemia-lymphoma Cell Lines by a Panel of 38 Monoclonal Antibodies," Journal of the National Cancer Institute 73(1):51-57, Oxford University Press, United States (Jul. 1984).
Sullivan, G.W., et al., "Interaction of Tumor Necrosis Factor-alpha and Granulocyte Colony-stimulating Factor on Neutrophil Apoptosis, Receptor Expression, and Bactericidal Function," Proceedings of the Association of American Physicians 108(6):455-466, Blackwell Science, Inc., United States (Nov. 1996).
Szybalska, E.H. and Szybalski, W., "Genetics of Human Cess Line IV DNA-mediated Heritable Transformation of A Biochemical Trait," Proceedings of the National Academy of Sciences USA 48:2026-2034, National Academy of Sciences, United States (Dec. 1962).
Tessarz, A.S. and Cerwenka, A., "The TREM-1/DAP12 Pathway," Immunology Letters 116(2):111-116, Elsevier/North-Holland Biomedical Press, Netherlands (Mar. 2008).
Thomas, K.R. and Capecchi, M.R., "Site-directed Mutagenesis by Gene Targeting in Mouse Embryo-derived Stem Cells," Cell 51(3):503-512, Cell Press, United States (Nov. 1987).
Thoma-Uszynski, S., et al., "Induction of Direct Antimicrobial Activity Through Mammalian Toll-like Receptors," Science 291(5508):1544-1547, American Association for the Advancement of Science, United States (Feb. 2001).
Thorpe, Antibody Carriers of Cytotoxic Agents in Cencer Therapy: A Review, in Monoclonal Antibodies 84: Biological and Clinical Applications, Pinchera et al., eds., pp. 475-506 (1985).
Thorpe, P.E. and Ross, W.C., "The Preparation and Cytotoxic Properties of Antibody-toxin Conjugates," Immunological Reviews 62:119-158, Blackwell, England (1982).
Tolstoshev, P., "Gene Therapy, Concepts, Current Trials and Future Directions," Annual Review of Pharmacology and Toxicology 33:573-596, Annual Reviews, United States (1993).

(56) References Cited

OTHER PUBLICATIONS

Tomasello, E., et al., "Combined Natural Killer Cell and Dendritic Cell Functional Deficiency in KARA/DAP12 Loss-of-function Mutant Mice," Immunity 13(3):355-364, Cell Press, United States (Sep. 2000).

Tomic, M., et al., "A Rapid and Simple Method for Introducing Specific Mutations Into Any Position of DNA Leaving All Other Positions Unaltered," Nucleic Acids Research 18(6):1656, Oxford University Press, England (Mar. 1990).

Tracey, K.J., et al., "Shock and Tissue Injury Induced by Recombinant Human Cachectin," Science 234(4775):470-474, American Association for the Advancement of Science, United States (1986).

Traunecker, A., et al., "Myeloma Based Expression System for Production of Large Mammalian Proteins," Trends in Biotechnology 9(4):109-113, Elsevier Science Publisher, England (Apr. 1991).

Trowbridge, R.S., et al., "Establishment and Characterization of Ferret Cells in Culture," In Vitro 18(11):952-960, Tissue Culture Assn, United States (Nov. 1982).

Tsuji, E., et al., "Simultaneous Onset of Acute Inflammatory Response, Sepsis-like Symptoms and Intestinal Mucosal Injury After Cancer Chemotherapy," International Journal of Cancer 107(2):303-308, Wiley-Liss, United States (Nov. 2003).

Turnbull, I.R., et al., "Cutting Edge: TREM-2 Attenuates Macrophage Activation," Journal of Immunology 177(6):3520-3524, American Association of Immunologists, United States (Sep. 2006).

Ulevitch, R.J., et al., "Recognition of Gram-negative Bacteria and Endotoxin by the Innate Immune System," Current Opinion in Immunology 11(1):19-22, Elsevier, England (Feb. 1999).

Upender, M., et al., "Megaprimer Method for in Vitro Mutagenesis Using Parallel Templates," Biotechniques 18(1):29-30, Informa Healthcare USA, Inc, England (Jan. 1995).

Urban, M.B., et al., "NF-kappa B Contacts DNA by a Heterodimer of the p50 and p65 Subunit," The EMBO Journal 10(7):1817-1825, Wiley Blackwell, England (Jul. 1991).

Van der Krol, A.R., et al., "Modulation of Eukaryotic Gene Expression by Complementary RNA or DNA Sequences," Biotechniques 6(10):958-976, Informa Healthcare, United States (Nov. 1988).

Van Keuren, M., et al., "Regional Assignment of Human Liver-Type 6-Phosphofructokinase to Chromosome 21q22.3 by Using Somatic Cell Hybrids and a Monoclonal Anti-L Antibody," Human Genetics 74(1):34-40, Springer Verlag, Germany (Sep. 1986).

Van Zeem K.J., et al., "Tumor Necrosis Factor Soluble Receptors Circulate During Experimental and Clinical Inflammation and Can Protect Against Excessive Tumor Necrosis Factor Alpha in Vitro and in Vivo," Proceedings of the National Academy of Sciences of the United States of America 89(11):4845-4849, National Academy of Sciences, United States (Jun. 1992).

Vincent, J.L., et al., "Clinical Trials of Immunomodulatory Therapies in Severe Sepsis and Septic Shock," Clinical Infectious Diseases 34(8):1084-1093, Oxford University Press, United States (Apr. 2002).

Wada, K.N., et al., "Codon Usage Tabulated From the Genbank Genetic Sequence Data," Nucleic Acids Research 20:2111-2118, Oxford University Press, England (May 1992).

Wakayama, T., et al., "Mice Cloned From Embryonic Stem Cells," Proceedings of the National Academy of Sciences of the United States of America 96(26):14984-14989, National Academy of Sciences, United States (Dec. 1999).

Walsh, C.E., et al., "Gene Therapy for Human Hemoglobinopathies," Proceedings of the Society for Experimental Biology and Medicine 204(3):289-300, Blackwell Science, United States (Dec. 1993).

Wang, H., et al., "HMG-1 as a Late Mediator of Endotoxin Lethality in Mice," Science 285(5425):248-251, American Association for the Advancement of Science, United States (1999).

Wang, Q., et al., "A Packaging Cell Line for Propagation of Recombinant Adenovirus Vectors Containing Two Lethal Gene-region Deletions," Gene Therapy 2(10):775-783, Nature Publishing Group, England (Dec. 1995).

Warren, H.S., "Strategies for the Treatment of Sepsis," The New England Journal of Medicine 336(13):952-953, Massachusetts Medical Society, United States (Mar. 1997).

Wasmuth, H.E., et al., "Patients With Acute on Chronic Liver Failure Display "Sepsis-like" Immune Paralysis," Journal of Hepatology 42(2):195-201, Elsevier, Netherlands (Feb. 2005).

Weintraub, H., et al., "Anti-sense RNA as a Molecular Tool for Genetic Analysis," Trends in Genetics 1:22-25 (1985).

Weis, D.D., et al., "Semi-automated Data Processing of Hydrogen Exchange Mass Spectra Using HX-express," Journal of the American Society for Mass Spectrometry 17(12):1700-1703, Springer, United States (2006).

Wells, J.A., "Additivity of Mutational Effects in Proteins," Biochemistry 29(37):8509-8517, American Chemical Society, United States (Sep. 1990).

Wheeler, A.P. and Bernard, G.R., "Treating Patients With Severe Sepsis," The New England Journal of Medicine 340(3):207-214, Massachusetts Medical Society, United States (Jan. 1999).

Wigler, M., et al., "Transfer of Purified Herpes Virus Thymidine Kinase Gene to Cultured Mouse Cells," Cell 11(1):223-232, Cell Press, United States (May 1977).

Wigler, M., et al., "Transformation of Mammalian Cells with an Amplifiable Dominant-Acting Gene," Proceedings of the National Academy of Sciences USA 77(6):3567-3570, National Academy of Sciences, United States (Jun. 1980).

Wilmut, I., et al., "Viable Offspring Derived From Fetal and Adult Mammalian Cells," Nature 385(6619):810-813, Nature Publishing Group, England (Feb. 1997).

Wilson, I.A., et al., "The Structure of an Antigenic Determinant in a Protein, " Cell 37(3):767-778, Cell Press, United States (Jul. 1984).

Winoto, A. and Baltimore, D., "A Novel, Inducible and T Cell-specific Enhancer Located at the 3' End of the T Cell Receptor Alpha Locus." The EMBO Journal 8(3):729-733, Wiley Blackwell, England (Mar. 1989).

Wu, G.Y. and Wu, C.H., "Delivery Systems for Gene Therapy," Biotherapy 3(1):87-95, Kluwer Academic Publishers, Netherlands (1991).

Wu, G.Y. and Wu, C.H., "Receptor-mediated in Vitro Gene Transformation by a Soluble DNA Carrier System," The Journal of Biological Chemistry 262(10):4429-4432, American Society for Biochemistry and Molecular Biology, United States (1987).

Wu, H., et al., "Humanization of a Murine Monoclonal Antibody by Simultaneous Optimization of Framework and CDR Residues," Journal of Molecular Biology 294(1):151-162, Elsevier, England (Nov. 1999).

Xu, J., et al., "Fibroblast Growth Factor 21 Reverses Hepatic Steatosis, Increases Energy Expenditure, and Improves Insulin Sensitivity in Diet-induced Obese Mice," Diabetes 58(1):250-259, American Diabetes Association, United States (2009).

Yadav, S., et al., "Establishing a Link Between Amino Acid Sequences and Self-associating and Viscoelastic Behavior of Two Closely Related Monoclonal Antibodies," Pharmaceutical Research 28(7):1750-1764, Kluwer Academic/Plenum Publishers, United States (2011).

Yadav, S., et al., "Specific Interactions in High Concentration Antibody Solutions Resulting in High Viscosity," Journal of Pharmaceutical Sciences 99(3):1152-1168, Elsevier, United States (2010).

Yadav, S., et al., "The Influence of Charge Distribution on Self-association and Viscosity Behavior of Monoclonal Antibody Solutions," Molecular Pharmaceutics 9(4):791-802, American Chemical Society, United States (2012).

Yadav, S., et al., "Viscosity Behavior of High-concentration Monoclonal Antibody Solutions: Correlation With Interaction Parameter and Electroviscous Effects," Journal of Pharmaceutical Sciences 101(3):998-1011, Elsevier, United States (2012).

Yamashita, Y., et al., "Inhibitory and Stimulatory Functions of Paired Ig-like Receptor (PIR) Family in RBL-2H3 Cells.," Journal of Immunology 161(8):4042-4047, American Association of Immunologists, United States (Oct. 1998).

Yie, J., et al., "FGF21 N- and C-termini Play Different Roles in Receptor Interaction and Activation," FEBS Letters 583(1):19-24, John Wiley & Sons Ltd, England (Jan. 2009).

(56) References Cited

OTHER PUBLICATIONS

Zervos, A.S., et al., Mxi1, a protein that specifically interacts with Max to bind Myc-Max recognition site, Cell 72(2):223-232, Elsevier Science, United States (1993).

Zijlstra, M., et al., "Germ-line Transmission of a Disrupted beta 2-microglobulin Gene Produced by Homologous Recombination in Embryonic Stem Cells," Nature 342(6248):435-438, Nature Publishing Group, England (Nov. 1989).

Zon, G., et al., "Oligonucleotide Analogues as Potential Chemotherapeutic Agents," Pharmaceutical Research 5(9):539-549, Kluwer Academic/Plenum Publishers, United States (Sep. 1988).

Zuckermann, R.N., et al., "Discovery of nanomolar ligands for 7-transmembrane G-protein-coupled receptors from a diverse N-(substituted)glycine peptoid librar," Journal of Medicinal Chemistry 37(17):2678-2685, ACS Publications, United Kingdom (1994).

Zwaveling, J.H., et al., "High Plasma Tumor Necrosis Factor (TNF)-alpha Concentrations and a Sepsis-like Syndrome in Patients Undergoing Hyperthermic Isolated Limb Perfusion With Recombinant TNF-alpha, Interferon-gamma, and Melphalan," Critical Care Medicine 24(5):765-770, Lippincott Williams & Wilkins, United States (May 1996).

Office Action mailed Mar. 12, 2018, in U.S. Appl. No. 15/325,865, inventor Henriksen, A., et al., filed Jan. 12, 2017, 9 pages.

FIG. 2C

| mAb ID | IC50 (nM) |
|---|---|
| 0170 | 0.24 |
| 0317 | 0.21 |
| 0318 | 0.47 |
| 0319 | 0.23 |
| 0320 | 0.39 |
| 0321 | 0.20 |
| 0322 | 0.26 |
| 0323 | 0.35 |
| 0324 | 0.41 |
| 0325 | 0.31 |
| 0326 | 0.36 |
| 0330 | 0.24 |
| 0332 | 0.32 |
| 0333 | 0.33 |

| SEQ. ID. NO | IC50 (nM) |
|---|---|
| 0170 | 0.24 |
| 0317 | 0.33 |
| 0318 | 0.49 |
| 0319 | 0.27 |
| 0320 | 0.32 |
| 0321 | 0.19 |
| 0322 | 0.26 |
| 0323 | 0.34 |
| 0324 | 0.37 |
| 0325 | 0.31 |
| 0326 | 0.31 |
| 0330 | 0.22 |

| SEQ. ID. NO | IC50 (nM) |
|---|---|
| 0170 | 6.0 |
| 0317 | 9.5 |
| 0318 | 5.6 |
| 0319 | 17.7 |
| 0322 | 5.9 |
| 0330 | 10.7 |

SITE DIRECTED MUTAGENESIS OF TREM-1 ANTIBODIES FOR DECREASING VISCOSITY

CROSS-REFERENCE TO RELATED APPLICATIONS

This application is a continuation application of U.S. application Ser. No. 16/203,327, filed Nov. 28, 2018; which is a divisional application of U.S. application Ser. No. 15/325,865, filed Jan. 12, 2017, issued as U.S. Pat. No. 10,179,814; which is a 371 of International Application No. PCT/EP2015/066501, filed Jul. 17, 2015; which claims priority to EP Application No. 14177547.8, filed Jul. 17, 2014, and EP Application No. 14194893.5, filed Nov. 26, 2014. The contents of all above-named applications are incorporated herein by reference.

REFERENCE TO SEQUENCE LISTING SUBMITTED ELECTRONICALLY

The content of the electronically submitted sequence listing in ASCII text file (Name: 105218 03 5002 US 02 Sequence Listing; Size: 50,659 bytes; and Date of Creation: Jul. 19, 2021) is incorporated herein by reference in its entirety.

TECHNICAL FIELD

The invention is directed to TREM-1 mAbs and to mutation of specific negatively charged and uncharged amino acids involved in either TREM-1 mAb self-interactions or TREM-1 mAb to TREM-1 interactions in order to lower the mAb solution viscosity and retain target affinity, and the invention relates to uses for such antibodies for therapeutic and pharmaceutical uses.

SEQUENCE LISTINGS OF THE INVENTION

SEQ ID NO: 1 represents the amino acid sequence of wild type (wt) human TREM-1.

SEQ ID NO: 2 represents the amino acid sequence of the heavy chain of a humanised TREM-1 antibody (mAb 0170 of WO2013/120553).

SEQ ID NO: 3 represents the amino acid sequence of the light chain of a humanised TREM-1 antibody (mAb 0170 of WO2013/120553).

SEQ ID NO: 4 represents the amino acid sequence of the light chain of a humanised TREM-1 antibody (mAb 0317, E27Q, E97S).

SEQ ID NO: 5 represents the amino acid sequence of the light chain of a humanised TREM-1 antibody (mAb 0318, E27Q, E97Q).

SEQ ID NO: 6 represents the amino acid sequence of the light chain of a humanised TREM-1 antibody (mAb 0319, E97S).

SEQ ID NO: 7 represents the amino acid sequence of the light chain of a humanised TREM-1 antibody (mAb 0320, E97Q).

SEQ ID NO: 8 represents the amino acid sequence of the light chain of a humanised TREM-1 antibody (mAb 0321, E27Q).

SEQ ID NO: 9 represents the amino acid sequence of the light chain of a humanised TREM-1 antibody (mAb 0322, F32A).

SEQ ID NO: 10 represents the amino acid sequence of the light chain of a humanised TREM-1 antibody (mAb 0323, F32S).

SEQ ID NO: 11 represents the amino acid sequence of the heavy chain of a humanised TREM-1 antibody (mAb 0324, A59Y).

SEQ ID NO: 12 represents the amino acid sequence of the heavy chain of a humanised TREM-1 antibody (mAb 0325, N57S).

SEQ ID NO: 13 represents the amino acid sequence of the heavy chain of a humanised TREM-1 antibody (mAb 0326, A59Y, N57S).

SEQ ID NO: 14 represents the amino acid sequence of the light chain of a humanised TREM-1 antibody (mAb 0330, F32A, E27Q, E97Q).

SEQ ID NO: 15 represents the amino acid sequence of the heavy chain of a humanised TREM-1 antibody (mAb 0332, A59Y; 0332 is a mAb combined of SEQ ID NO: 15 as the HC and SEQ ID NO 5 as the LC, Table 1).

SEQ ID NO: 16 represents the amino acid sequence of the heavy chain of a humanised TREM-1 antibody (mAb 0333, A59Y; 0333 is a mAb combined of SEQ ID NO: 16 as the HC and SEQ ID NO 14 as the LC, Table 1).

SEQ ID NO: 17 represents the amino acid sequence of full length cTREM-1.

SEQ ID NO 18 represents the heavy chain of the Fab region of mAb 0170.

SEQ ID NO 19 represents the light chain of the Fab region of mAb 0170.

BACKGROUND

TREM-1 is an activating receptor expressed on monocytes, macrophages and neutrophils. These cells play a central role in chronic inflammatory diseases by releasing cytokines and other mediators that drive inflammation. TREM-1 mRNA and protein expression is up-regulated in patients with RA and IBD, and TREM-1-positive cells accumulate at sites of inflammation, correlating with disease severity. Peptidoglycan-recognition-protein 1 (PGLYRP1) expressed primarily by activated neutrophils is a ligand for TREM-1 and mediate TREM-1 signalling upon binding.

In vitro, engagement of TREM-1 triggers secretion of pro-inflammatory cytokines including TNF, IL-8, and monocyte chemotactic protein-1. In addition, TREM-1 signalling synergizes with multiple Toll-like Receptors (TLR) to further boost pro-inflammatory signals. In turn, this up-regulates expression of TREM-1, leading to a vicious cycle amplifying the inflammation. Increasing evidence indicates that TLRs contribute to the development and progression of chronic inflammatory diseases such as RA and IBD.

WO 2013/120553 discloses humanized anti-TREM-1 mAbs which inhibit both human and cynomolgus TREM-1 function. However, the viscosity profile of anti-TREM-1 mAbs may hamper the manufacturing process to produce a drug product at >50 mg/ml and could limit the optimal dose setting in the clinic. High dosage (several mg/kg) of protein therapeutics is often needed to achieve an adequate clinical effect and since the vast majority of these therapeutics are administered by subcutaneous delivery, the consequence is that patient self-administration of the therapeutic is limited to volumes of <1.5 mL (Shire et al., 3. Pharm. Sci. 2004, 93, 1390-1402). The development of high concentration protein formulations suitable for patient self-administration is a general obstacle for manufacturing and delivery when protein formulation results in high viscosity of the resultant solution.

Charge distribution of mAbs has been studied with regards to the effect on the viscosity behaviour of mAb solutions (Ydav et al., Mol. Pharmaceutics 2012, 9, 791-802). Also, weak non-specific charge interactions that persist in dilute solutions have been shown to influence the viscosity of concentrated mAb solutions (Connolly et al., Biophys. 3, 2012, 103, 69-78.). The remedies to reduce the viscosity of mAb solutions have been to introduce site-directed charge swap mutations that disrupt direct charge-charge intermolecular interactions (Ydav et al., Mol. Pharmaceutics 2012, 9, 791-802) or the addition of salts or counter ions (Liu et al., 3. Pharm. Sci. 2005, 94, 1928-1940; Yadav et al., 3. Pharm. Sci. 2010, 99, 1152-1168; Yadav et al., 3. Pharm. Sci. 2012, 101, 998-1011; Kanai et al., 3. Pharm. Sci. 2008, 97, 4219-4227). The addition of salts and counter ions can, however, result in adverse effects for the patient in terms of hyper-osmolality of the administered solution.

Disclosed herein are TREM-1 antibodies generated by site-specific mutation of the CDR's of the WO 2013/120553 disclosed humanized anti-TREM-1 mAb 0170. The disclosed antibodies do not disrupt direct mAb intermolecular charge-charge self-interactions but do have a favourable viscosity profile and maintained target binding profile. The favourable viscosity profile allows drug product to be produced at high concentrations that could be essential for therapeutic and pharmaceutical use. Such antibodies may have a substantial impact upon the quality of life of individuals with sepsis or a chronic inflammatory disease such as rheumatoid arthritis, psoriatic arthritis and inflammatory bowel disease.

SUMMARY

A primary aspect of the invention is directed to an anti-TREM-1 mAb with a viscosity profile in the range expected for monomeric mAbs and which blocks TREM-1 function as potently as mAb0170 of WO 2013/120553. Further to the advantageous viscosity profiles of the variant mAbs of the invention, said variants do not show agonism to the TREM-1 receptor.

One aspect of the invention is directed to an antibody or fragment thereof that is capable of binding to and blocking TREM-1, characterized in that the antibody, or an antibody fragment of said antibody, has a viscosity of less than 5 cP at a concentration of 80 mg/mL, preferably less than 4 cP.

The antibody or fragment thereof may comprise a variant of SEQ ID NO: 3, wherein one or more of the negatively charged residues in CDR1 and CDR3 region of SEQ ID NO: 3 are substituted with uncharged amino acid residues, as described herein.

The antibody or fragment thereof may comprise a variant of SEQ ID NO: 3 wherein phenylalanine at position 32 of SEQ ID NO 3 is mutated to an amino acid selected from amino acid residues glycine, serine, threonine, cysteine, alanine, valine, leucine, isoleucine and methionine, preferably selected from alanine, glycine, serine valine and leucine, more preferably wherein F32 of SEQ ID NO: 3 is mutated to alanine or serine.

The antibody or fragment thereof may comprise a variant of SEQ ID NO: 2 wherein any one of residues Y32, R52, S55, S56, N57, A59, M102, 1104 and R106 of SEQ ID NO: 2 or F32, D33, Y34, Y53, R54, D98 of SEQ. ID NO 3 ("Fab-Fab interaction" mutations) is substituted with another amino acid, such as natural amino acid, preferably an amino acid residue selected from the group consisting of glycine, alanine, serine, asparagine, glutamine, threonine, cysteine, lysine, arginine, tryptophan, histidine and tyrosine.

A further aspect of the invention is directed to an antibody or fragment thereof that is capable of specifically binding to and blocking TREM-1 of SEQ ID NO: 1 and comprises variants of SEQ ID NO: 2 or SEQ ID NO: 3 or both, wherein the variants are selected from the group consisting of "Fab-Fab interaction" mutations, "Fab-TREM-1 interaction" mutations and "charge-patch" mutations of SEQ ID NO: 2 or SEQ ID NO: 3 (table 1).

In one embodiment of an antibody or fragment thereof of the invention, one or more of the negatively charged residues in CDR1 and CDR3 regions of SEQ ID NO: 3 are substituted with uncharged amino acid residues. In one embodiment, the negatively charged residues in CDR1 and CDR3 regions of SEQ ID NO: 3 are substituted with uncharged amino acid residues.

In one embodiment, an antibody or fragment thereof of the invention comprises a variant of SEQ ID NO 3 wherein any one of the "charge patch" residues D1, D30, D33, D74, D98, E27, E97 of SEQ ID NO: 3 is mutated to an amino acid residue selected from the group consisting of glycine, alanine, serine, asparagine, glutamine, threonine, cysteine, and tyrosine. In one embodiment, more than one of the "charge patch" residues D1, D30, D33, D74, D98, E27, E97 of SEQ ID NO 3 is mutated to an amino acid residue selected from the group consisting of glycine, alanine, serine, asparagine, glutamine, threonine, cysteine, and tyrosine.

In one embodiment, one of E27 and E97 of the CDR1 and CDR3 regions of SEQ ID NO 3 is substituted with an uncharged amino acid residue, such as an amino acid selected from the group consisting of glycine, alanine, serine, asparagine, glutamine, threonine, cysteine, and tyrosine. By way of example, E27 of SEQ ID NO 3 may remain unmutated and E97 may be mutated with an amino acid selected from the group consisting of glycine, alanine, serine, asparagine, glutamine, threonine, cysteine, and tyrosine, more preferably with an amino acid selected from the group consisting of serine and glutamine. Alternatively, E97 of SEQ ID NO 3 may remain unmutated and E27 may be substituted with an amino acid selected from the group consisting of glycine, alanine, serine, asparagine, glutamine, threonine, cysteine, and tyrosine, more preferably with an amino acid selected from the group consisting of serine and glutamine.

In one embodiment, both E27 and E97 of the CDR1 and CDR3 regions of SEQ ID NO 3 are substituted with uncharged amino acid residues, such as an amino acid selected from the group consisting of glycine, alanine, serine, asparagine, glutamine, threonine, cysteine, and tyrosine. By way of example, E27 of SEQ ID NO 3 may be mutated to glutamine and E97 of SEQ ID NO 3 may be substituted with an amino acid selected from the group consisting of glycine, serine, asparagine, glutamine, threonine, cysteine, and tyrosine, more preferably with an amino acid selected from the group consisting of serine and glutamine.

In a further aspect, the invention provides an antibody or fragment thereof comprising a variant of SEQ. ID. NO 2 wherein any one of residues Y32, R52, S55, S56, N57, A59, M102, 1104 and R106 of SEQ ID NO: 2 or F32, D33, Y34, Y53, R54, D98 of SEQ ID NO: 3 ("Fab-Fab interaction" mutations) is substituted with another amino acid, such as natural amino acid, preferably an amino acid residue selected from the group consisting of glycine, alanine, serine, asparagine, glutamine, threonine, cysteine, lysine, arginine, tryptophan, histidine and tyrosine.

In one embodiment of the antibody or fragment thereof of the invention, at least one of residues A59 and N57 of SEQ ID NO: 2 is mutated to an amino acid residue, such as a natural amino acid, preferably an amino acid selected from the group consisting of glycine, alanine, serine, asparagine, glutamine, threonine, cysteine, lysine, arginine, tryptophan, histidine and tyrosine, more preferably serine or tyrosine. By way of example, A59 of SEQ ID NO: 2 may remain unmutated and N57 may be mutated to another amino acid residue, such as a natural amino acid, preferably selected from the group consisting of glycine, alanine, serine, asparagine, glutamine, threonine, cysteine, lysine, arginine, tryptophan, histidine and tyrosine, more preferably serine or tyrosine. Alternatively, N57 of SEQ ID NO: 2 may remain unmutated and A59 of SEQ ID NO 2 may be mutated to another amino acid residue, such as a natural amino acid, preferably selected from the group consisting of glycine, alanine, serine, asparagine, glutamine, threonine, cysteine, lysine, arginine, tryptophan, histidine and tyrosine, more preferably serine or tyrosine. In a further embodiment, both A59 and N57 of SEQ ID NO: 2 are mutated to another amino acid residue, such as a natural amino acid, preferably selected from the group consisting glycine, alanine, serine, asparagine, glutamine, threonine, cysteine, lysine, arginine, tryptophan, histidine and tyrosine, more preferably serine or tyrosine.

A further aspect of the invention is directed to an improved preclinical evaluation value obtained by introduction of site-directed mutations in SEQ ID NO: 3 in the "Fab-TREM-1 interaction" amino acid residues to achieve the same mAb affinity for cynomolgus TREM-1 as for human TREM-1 of SEQ ID NO: 1, such as wherein a Phe residue of SEQ ID NO: 3 is substituted with Ala or Ser.

The invention thus provides an antibody or fragment thereof wherein the "Fab-TREM-1 interaction" amino acid residue, F32 of SEQ ID NO: 3, is substituted with an amino acid residue selected from the group consisting of glycine, alanine, serine, threonine, proline and cysteine.

A further aspect of the invention is directed to a combined effect of improved viscosity properties and improved preclinical evaluation value obtained by introduction of site-directed mutations in SEQ ID NO: 2 in the mAb-TREM-1 interface to achieve the same mAb affinity for cynomolgus as exist for human TREM-1 of SEQ ID NO: 1 (e.g. as described above) in combination with substitution of negatively charged residues in CDR1 and CDR3 regions of SEQ ID NO: 3 with uncharged amino acid residues (e.g. as described above).

In accordance with any of the above-described aspects of the invention, there is provided an antibody or fragment thereof wherein:
i) at least one negatively charged residue of the CDR1 and CDR3 regions of SEQ ID NO: 3 is mutated to an amino acid residue selected from the group consisting of glycine, alanine, serine, asparagine, glutamine, threonine, cysteine, and tyrosine; and
ii) at least one residue of residues Y32, R52, S55, S56, N57, A59, M102, I104 and R106 of SEQ ID NO: 2 or F32, D33, Y34, Y53, R54, D98 of SEQ ID NO: 3 ("Fab-Fab interaction" mutations) is mutated to an amino acid residue selected from the group consisting of glycine, alanine, serine, asparagine, glutamine, threonine, cysteine, lysine, arginine, and tryptophan, histidine and tyrosine.

In one embodiment, there is provided an antibody or fragment thereof wherein:
i) one or both of E27 and E97 of SEQ ID NO: 3 is/are mutated to an amino acid residue selected from the group consisting of glycine, alanine, serine, asparagine, glutamine, threonine, cysteine, and tyrosine; and
ii) one or both of A59 and N57 of SEQ ID NO: 2 is/are mutated to an amino acid residue selected from the group consisting of glycine, alanine, serine, asparagine, glutamine, threonine, cysteine, lysine, arginine, tryptophan, histidine and tyrosine, more preferably serine or tyrosine.

The invention further relates to an antibody or fragment thereof comprising any one of SEQ ID NOs 4 to 16.

BRIEF DESCRIPTION OF DRAWINGS

FIGS. 2A-2E depict the ability of mAb 0170 variants to inhibit human TREM-1 signalling in human TREM-1 reporter cell line (BWZ'36/hTREM-1) stimulated with PGN and (FIGS. 2A-2C) recombinant PGLYRP1 or (FIGS. 2D-2E) PGLYRP1 expressed by activated neutrophils (average of N donors).

DESCRIPTION

Figure 1:
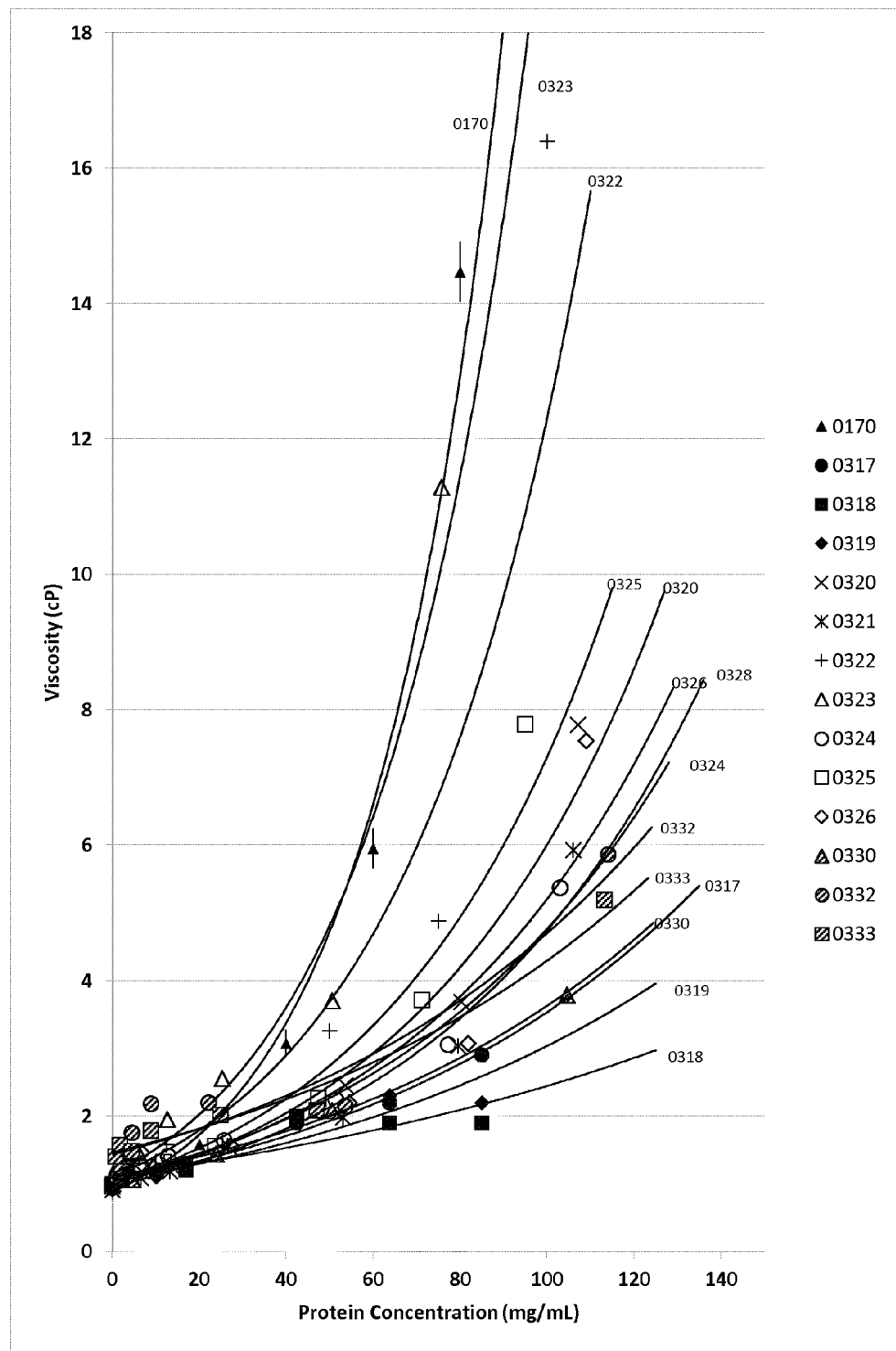
FIG. 1 depicts the viscosity profile of anti-TREM-1 mAb variants and their exponential curve fits.
Figure 2A:
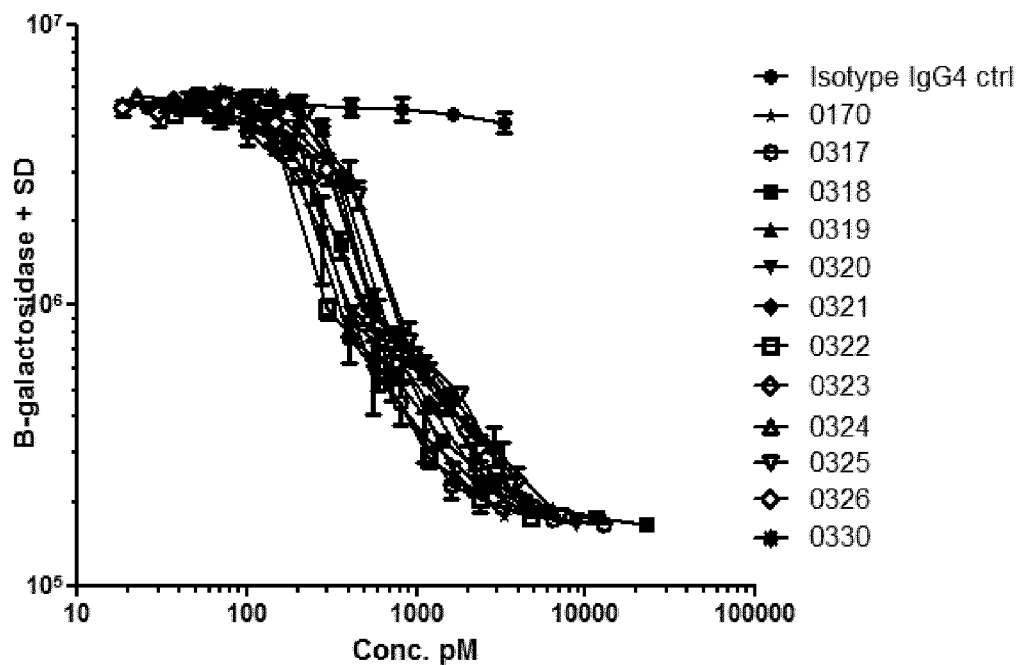
Figure 2B:
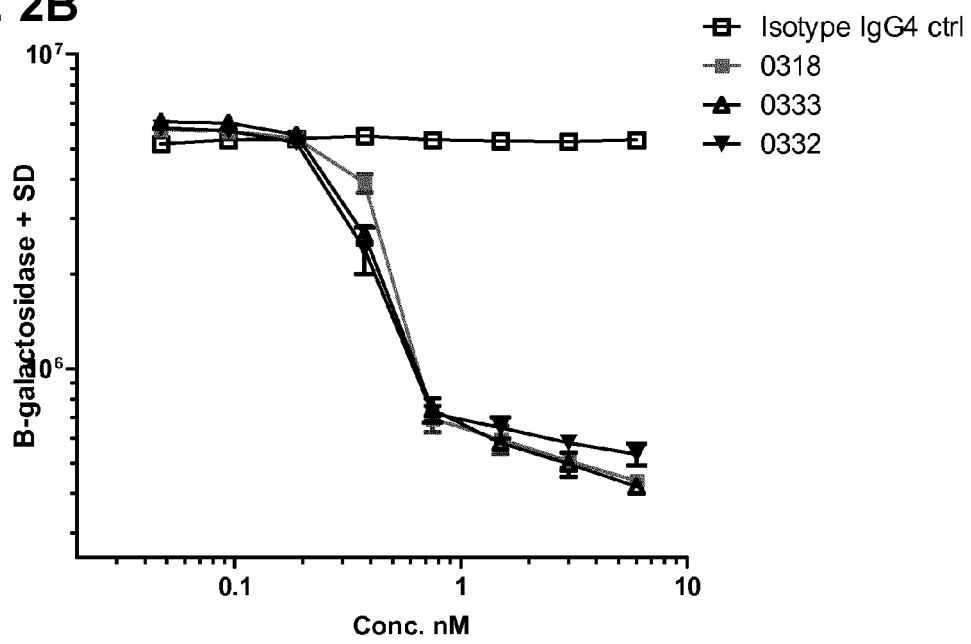
Figures 2D, 2E:
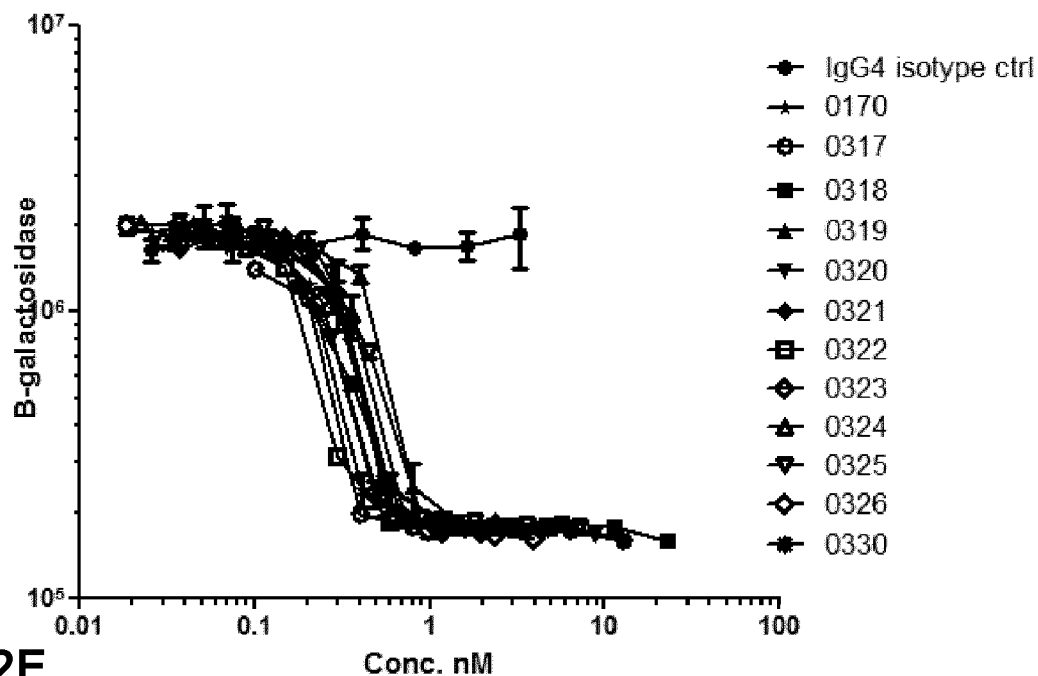

TREM-1 is a transmembrane protein that consists of 234 amino acids, including a single extracellular immunoglobulin domain and a short cytoplasmic tail with no apparent signaling motif. When activated, TREM-1 associates with the ITAM-containing signaling adaptor protein, DAP12. Downstream signalling may include activation of the NFAT transcription factor, causing an up-regulation of pro-inflammatory cytokine production.

The present invention relates to antibodies that are capable of specifically binding and blocking the function of TREM-1. Antibodies of the invention may block TREM-1 function by reducing/blocking TREM-1 activation and downstream signalling.

Antibodies according to the invention may block TREM-1 by means of one or a combination of several different mechanisms, blocking TREM-1 directly or indirectly. For example, antibodies of the invention may prevent the natural ligand of TREM-1, peptidoglycan recognition protein 1 (PGLYRP1), from creating a functional complex with TREM-1 and/or antibodies of the invention may block TREM-1 by preventing individual TREM-1 molecules from forming dimers or multimers. TREM-1 dimerisation or multimerisation may be reduced or prevented by TREM-1 antibodies that are capable of binding to a portion of TREM-1 that would otherwise reside in the interface of a TREM-1 dimer, thus preventing individual TREM-1 molecules from associating with one another.

TREM-1 dimerisation or multimerisation may be reduced or prevented by TREM-1 antibodies that interfere with the interaction of TREM-1 with its ligand. Antibodies according to the current invention may block PGLYRP1-induced activation of TREM-1. PGLYRP1, a highly conserved, 196 amino acid long protein consisting of a signal peptide and a peptidoglycan binding domain, is expressed in neutrophils and released upon their activation. Antibodies according to the current invention may down-regulate pro-inflammatory cytokine release from myeloid cells. Antibodies according to the current invention may block the release of TNF, MIP-1beta, MCP-1, IL-1beta, GM.CSF, IL-6 and/or IL-8 from macrophages, neutrophils, synovial tissue cells and/or a reporter cell, as disclosed herein.

Antibodies of the invention may be capable of binding both human TREM-1 and TREM-1 from another species than a human being. The term "TREM-1", as used herein, thus encompasses any naturally occurring form of TREM-1 which may be derived from any suitable organism. For example, TREM-1 for use as described herein may be vertebrate TREM-1, such as mammalian TREM-1, such as TREM-1 from a primate (such as a human, a chimpanzee, a cynomolgus monkey or a rhesus monkey); a rodent (such as a mouse or a rat), a lagomorph (such as a rabbit), or an artiodactyl (such a cow, sheep, pig or camel). Preferably, the TREM-1 is SEQ ID NO: 1 (human TREM-1). The TREM-1 may be a mature form of TREM-1 such as a TREM-1 protein that has undergone post-translational processing within a suitable cell. Such a mature TREM-1 protein may, for example, be glycosylated. The TREM-1 may be a full length TREM-1 protein.

Antibodies of the invention may be monoclonal antibodies, in the sense that they are directly or indirectly derived from a single clone of a B lymphocyte. TREM-1 antibodies may be produced, screened and purified using, for example, the methods described in the Examples of WO2013/120553. In brief, a suitable mouse such as a TREM-1 or TREM-1/TREM-3 knock-out (KO) mouse may be immunised with TREM-1, a cell expressing TREM-1 or a combination of both.

Antibodies of the invention may be polyclonal in the sense of being a mixture of monoclonal antibodies according to the current invention.

Primary screening of hybridoma supernatants may be performed using direct ELISA or FMAT and secondary screening may be performed using flow cytometry. Positive hybridoma supernatants may then be screened in a reporter gene assay.

Antibodies may be recombinantly expressed in prokaryotic or eukaryotic cells. The prokaryotic cell may be *E. coli*. The eukaryotic cell may be a yeast, insect or mammalian cell, such as a cell derived from an organism that is a primate (such as a human, a chimpanzee, a cynomolgus monkey or a rhesus monkey), a rodent (such as a mouse or a rat), a lagomorph (such as a rabbit) or an artiodactyl (such a cow, sheep, pig or camel). Suitable mammalian cell lines include, but are not limited to, HEK293 cells, CHO cells and HELA cells. TREM-1 antibodies may also be produced by means of other methods known to the person skilled in the art, such as a phage display or a yeast display.

Once produced, antibodies may be screened for binding to, for example, full length TREM-1 or mutants thereof using the methods described in the Examples of WO2013/120553.

Functional TREM-1 antibodies of the current invention are antibodies that are capable of specifically binding TREM-1 and that have an effect upon TREM-1 activation and downstream signalling by either blocking or stimulating TREM-1 and they are herein referred to as "functional TREM-1 antibodies". The method of identifying a functional TREM-1 antibody comprises (a) culturing a first cell expressing TREM-1, a signalling protein and a reporter construct; (b) measuring the activity of the first cell when said cell is incubated with a TREM-1 modifying agent; (c) contacting the co-culture of (b) with a TREM-1 antibody; and (d) measuring that the activity of the first cell is less than or more than the activity measured in (b).

The "first cell" of (a) may be a cell of haematopoietic origin, such as a myeloid cell, such as a T-cell. The signalling protein of (a) may be any signalling protein that is capable of forming a complex with TREM-1. Suitable signalling proteins include DAP10, DAP12, TCR zeta, Fc gamma RIII and an Fc receptor, or part thereof. The reporter construct of (a) may be any construct that is capable of being activated via the signalling protein and generating a recognisable signal. Suitable reporter constructs comprise a transcription factor and a reporter gene. The signalling protein may signal via a transcription factor selected from the group consisting of the NFAT and NFkB. The reporter gene is a gene that is not natively expressed in said first cell and may be but is not limited to be a gene that encodes β-galactosidase, luciferase, green fluorescent protein (GFP) or chloramphenicol transferase. Said first cell may be transfected with a transcription factor and a reporter gene using methods that are well known in the art.

The "BWZ/hTREM-1 reporter cell" and "TE426.27 reporter cell" described in the Examples is one example of a "first cell".

The modifying agent of (b) may be a TREM-1 ligand or an activated neutrophil. The "TREM-1 antibody" of (c) may be a TREM-1 specific hybridoma supernatant or a purified antibody. The activity measured in (d) is the signal produced by the reporter construct. An example of such signalling is the luminescence caused by NFAT-driven LacZ (β-lactamase luciferase) production.

The method may be tailored to identify a blocking TREM-1 antibody. The method of identifying a blocking TREM-1 antibody comprises (a) culturing a first cell expressing TREM-1, a signalling protein and a reporter construct; (b) measuring the activity of the first cell when said cell is incubated with an activated neutrophil; (c) contacting the co-culture of the first cell and the activated neutrophil with a TREM-1 antibody; and (d) measuring that the activity of the first cell is less than the activity measured in (b).

The method may also be tailored to identify a stimulating TREM-1 antibody. The method of identifying a stimulating TREM-1 antibody comprises (a) culturing a first cell expressing TREM-1, a signalling protein and a reporter construct; (b) measuring the activity of the first cell; (c) contacting/incubating said cell with a TREM-1 antibody; and (d) measuring that the activity of the first cell is more than the activity of the measured in (b).

The present invention relates to blocking TREM-1 antibodies that may be identified by means of the method, herein disclosed, of identifying a blocking antibody. When tested using the method described above and in the Examples, an antibody according to the current invention may, at a concentration of less than 50 μg/ml, such as less than 40 μg/ml, such as less than 30 μg/ml, such as less than 20 μg/ml, such as less than 10 μg/ml, such as less than 5 μg/ml, such as less than 1 μg/ml—be capable of reducing the activity of said first cell by 50%, such as 60%, such as 70%, such as 80%, such as 90%, such as 95%, such as 100%. An antibody according to the invention may be capable of completely extinguishing the activity of the first cell. When tested using the method described above and in the Examples, an antibody according to the current invention may, at a concentration of less than 1 µg/ml—such as less than 0.9 µg/ml, such as less than 0.8 µg/ml, such as less than 0.7 µg/ml, such as less than 0.6 µg/ml, such as less than 0.5 µg/ml, such as less than 0.4 µg/ml, such as less than 0.3 µg/ml, such as less than 0.2 µg/ml—be capable of extinguishing the activity of the first cell.

The present invention also relates to blocking TREM-1 antibodies that may be identified by other means than the method herein disclosed.

The term "antibody" herein refers to a protein, derived from a germline immunoglobulin sequence, which is capable of specifically binding to an antigen (TREM-1) or a portion thereof. The term includes full length antibodies of any class or isotype (that is, IgA, IgE, IgG, IgM and/or IgY) and any single chain or fragment thereof. An antibody that specifically binds to an antigen, or portion thereof, may bind exclusively to that antigen, or portion thereof, or it may bind to a limited number of homologous antigens, or portions thereof. Full-length antibodies usually comprise at least four polypeptide chains: two heavy (H) chains and two light (L) chains that are interconnected by disulfide bonds. One immunoglobulin sub-class of particular pharmaceutical interest is the IgG family. In humans, the IgG class may be sub-divided into 4 sub-classes: IgG1, IgG2, IgG3 and IgG4, based on the sequence of their heavy chain constant regions. The light chains can be divided into two types, kappa and lambda, based on differences in their sequence composition. IgG molecules are composed of two heavy chains, inter-linked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hyper-variability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a [binding] domain that is capable of interacting with an antigen, whilst the constant region of an antibody may mediate binding of the immunoglobulin to host tissues or factors, including but not limited to various cells of the immune system (effector cells), Fc receptors and the first component (Clq) of the classical complement system.

Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain the ability to specifically bind to an antigen, such as TREM-1, as described herein. Examples of antigen-binding fragments include Fab, Fab', F(ab)2, F(ab')2, F(ab)S, Fv (typically the VL and VH domains of a single arm of an antibody), single-chain Fv (scFv; see e.g. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 25:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

An antibody of the invention may be a human antibody or a humanised antibody. The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma, which includes a B cell obtained from a transgenic nonhuman animal, e.g., a transgenic mouse, having a genome comprising a human heavy chain transgene and a light chain transgene fused to an immortalized cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains one or more sequences (CDR regions or parts thereof) that are derived from a non-human immunoglobulin. A humanised antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (backmutation) of the amino acid residue from the donor antibody has beneficial impact on the properties of the humanised antibody. In addition to donor antibody derived backmutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another agent or antibody.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant segments.

The fragment crystallisable region ("Fc region"/"Fc domain") of an antibody is the N-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprises one or more, and perhaps all of the following mutations that will result in decreased affinity to certain Fc receptors (L234A, L235E, and G237A) and in reduced Clq-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may be modified to stabilize the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilise inter heavy chain disulphide bridge formation at the hinge (see, e.g., Angal et al., Mol Immunol. 1995; 30: 105-8).

Antibodies or fragments thereof may also be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-59 (L2) and 89-97 (L3) of the light-chain variable domain and 31-35 (H1), 50-65 (H2) and 95-102 (H3) in the heavy-chain variable domain; (Kabat et al. 1991; Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, 3. Mol. Biol 1987; 196: 901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

The mAb 0170 antibody has a variable heavy chain sequence as shown in SEQ ID NO: 2 and a variable light chain sequence as shown in SEQ ID NO: 3. An antibody of the invention may comprise this variable heavy chain sequence and/or this variable light chain sequence. The mAb 0170 antibody has the CDR sequences shown at amino acids 31 to 35, 50 to 68 and 101 to 110 of SEQ ID NO: 2 and amino acids 24 to 38, 54 to 60 and 93 to 101 of SEQ ID NO: 3.

The heavy chain of an antibody according to the invention may comprise a CDR1 sequence of amino acids 31 to 35 (TYAMH) of SEQ ID NO: 2, wherein one of these amino acids may be substituted by a different amino acid.

The heavy chain of an antibody according to the invention may comprise a CDR2 sequence of amino acids 50 to 68 (RIRTKSSNYATYYADSVKD) of SEQ ID NO: 2, wherein one, two or three of these amino acids may be substituted by a different amino acid.

The heavy chain of an antibody according to the invention may comprise a CDR3 sequence of amino acids 101 to 110 (DMGQRRQFAY) of SEQ ID NO: 2, wherein one, two or three of these amino acids may be substituted by a different amino acid.

The light chain of an antibody according to the invention may comprise a CDR1 sequence of amino acids 24 to 38 (RASESVDTFDYSFLH) of SEQ ID NO: 3, wherein one, two or three of these amino acids may be substituted with a different amino acid.

The light chain of an antibody according to the invention may comprise a CDR2 sequence of amino acids 54 to 60 (RASNLES) of SEQ ID NO: 3, wherein one or two of these amino acids may be substituted with a different amino acid.

The light chain of an antibody according to the invention may comprise a CDR3 sequence of amino acids 93 to 101 (QQSNEDPYT) of SEQ ID NO: 3, wherein one or two of these amino acids may be substituted with a different amino acid.

The mAb 0170 antibody has a heavy chain sequence as shown in SEQ ID NO: 2 and a light chain sequence as shown in SEQ ID NO: 3. An antibody of the invention may comprise this heavy chain sequence or this light chain sequence. Either the heavy or light chain of the antibody of the invention, or both, may be a variant of mAb 0170. The mAb 0170 antibody has the CDR sequences shown at amino acids 31 to 35, 50 to 68 and 101 to 110 of SEQ ID NO: 2 and amino acids 24 to 38, 54 to 60 and 93 to 101 of SEQ ID NO: 3. An antibody of the invention may comprise 1, 2, 3, 4, 5 or all 6 of these CDR sequences.

The heavy chain of an antibody according to the invention may comprise a CDRH3 sequence of amino acids 101 to 110 (DMGIRRQFAY) of SEQ ID NO: 2, wherein one, two or three of these amino acids may be substituted by a different amino acid.

The term "antigen" (Ag) refers to the molecular entity used for immunization of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process, or other process, e.g. phage display, used for generating the Ab.

The term "epitope", as used herein, is defined in the context of a molecular interaction between an "antigen binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined through various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term epitope herein comprises both types of binding region in any particular region of TREM-1 that specifically binds to a TREM-1 antibody. TREM-1 may comprise a number of different epitopes, which may include, without limitation, conformational epitopes which consist of one or more non-contiguous amino acids located near each other in the mature TREM-1 conformation and post-translational epitopes which consist, either in whole or part, of molecular structures covalently attached to TREM-1, such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At an even less detailed level the epitope can be characterized by the amino acid residues that it comprises as defined by a specific criteria such as the distance between or solvent accessibility of atoms in the Ab:Ag complex. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as TREM-1 residues characterized by having a heavy atom (i.e. a non-hydrogen atom) within a distance of, eg., 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue are shared by the epitopes.

Epitopes may also be defined indirectly, by means of comparing the binding kinetics of antibodies to wild type human TREM-1 with those of human TREM-1 variants that have alanine mutations in anticipated epitopes. Decreased affinity or abrogated binding of an antibody to variants of human TREM-1 in which an amino acid residue has been replaced with an alanine residue indicates that the mutated amino acid contributes to the interaction between said antibody and wild type human TREM-1. This approach provides a negative identification of the epitope. The method is compromised in effectively defining the epitope by the fact that protein misfolding or unfolding would give similar results as abrogation of interaction. The analysis can be complemented by comparative gain of function mutational analyses of an orthologous target protein (eg., cynomolgus monkey TREM-1), if a cross-reactive antibody exists. The comparison will define the epitope differences between the antibody that does not cross-react with, eg., cynomolgus monkey TREM-1 and the cross-reactive antibody.

Indirect identification of the epitope can also be provided by means of measuring antibody (or antibody fragment) binding to variants of the wild type antigen (TREM-1). If an antibody or fragment thereof binds, eg., human but not cynomolgus monkey TREM-1 and if said antibody or fragment thereof is capable of binding a partly humanised variant of cynomolgus monkey TREM-1 then this regained binding indicates that the substituted amino acid residue(s) is/are important for the interaction of the antibody with the antigen. In the same way, increased affinity for humanized variants of cynomolgus monkey TREM-1, of an anti-human TREM-1 antibody (or its Fab fragment) that has a weaker binding to cynomolgus monkey TREM-1 compared to human TREM-1, can provide information on the identity of residues composing the binding epitope.

The effect of the same mutations on any given cross-reactive antibody makes it possible to discriminate between possible protein misfolding (abrogated binding to both antibodies) and loss of interaction in human TREM-1 (binding to one of the antibodies and abrogated binding to the other antibody), whilst unambiguously providing information on the epitope differences between the antibody that does not cross-react and the cross reactive antibody on an amino acid level.

Antibodies of the current invention may be capable of binding variants of human TREM-1 as determined using, eg., surface plasmon resonance.

Antibodies of the current invention may be capable of binding variants of cynomolgus monkey TREM-1 as determined using, eg., surface plasmon resonance.

An antibody of the invention may be capable of specifically binding TREM-1, wherein said antibody is capable of specifically binding (i) at least one amino acid residue selected from the group consisting of the A21, T22, K23, L24, T25, E26, and (ii) at least one amino acid residue selected from the group consisting of the A49, 550, 551, Q52, K53, A54, W55, Q56, I57, I58, R59, D60, G61, E62, M63, P64, K65, T66, L67, A68, C69, T70, E71, R72, P73, 574, K75, N76, 577, H78, P79, V80, Q81, V82, G83, R84, 185 and (iii) at least one amino acid residue selected from the group consisting of the C113, V114, I115, Y116, Q117, P118 and P119 of human TREM-1.

An antibody of the invention may be capable of specifically binding a polypeptide comprising amino acids D38 to F48 of SEQ ID NO: 1 (human TREM-1), as determined using, eg., HX-MS or X-ray diffraction.

An antibody of the invention may have an epitope comprising one, two, three, four, five, six, seven or all of the amino acid residues D38, V39, K40, C41, D42, Y43, T44 and L45 of SEQ ID NO: 1 (human TREM-1) and one, two or all of the amino acid residues selected from the group consisting of the E46, K47 and F48 of SEQ ID NO: 1 (human TREM-1), as determined using, eg., HX-MS or X-ray diffraction.

An antibody of the invention may have an epitope comprising one, two, three or all of the amino acid residues selected from the group consisting of the D42, E46, D92 and H93 of SEQ ID NO: 1 (human TREM-1), as determined using variants of TREM-1 and surface plasmon resonance.

An antibody of the invention may have an epitope comprising at least the amino acid residues E46 and/or D92 of SEQ ID NO: 1 (human TREM-1), as determined using variants of TREM-1 and surface plasmon resonance.

An antibody of the invention may further comprise one, two or all of the amino acid residues selected from the group consisting of L31, I86 and V101 of SEQ ID NO: 1 (human TREM-1).

An antibody of the invention may be capable of specifically binding a polypeptide comprising amino acid residues E19 to L26 of cynomolgus monkey TREM-1 (SEQ ID NO: 17), as determined using, eg. HX-MS or X-ray diffraction.

An antibody of the invention may be capable of specifically binding human TREM-1, wherein the epitope of said antibody comprises one, two, three, four, five, six, seven, eight, nine or all of the amino acid residues selected from the group consisting of the V39, K40, C41, D42, Y43, L45, E46, K47, F48 and A49 of SEQ ID NO: 1.

An antibody of the invention may be capable of specifically binding human TREM-1, wherein the epitope of said antibody comprises the D42 of SEQ ID NO: 1. An antibody of the invention may be capable of specifically binding human TREM-1, wherein the epitope of said antibody comprises the E46 of SEQ ID NO: 1. The epitope of said antibody may comprise the V39, C41, D42, Y43, L45 of SEQ ID NO: 1. The epitope of said antibody may comprise the E46, K47 and A49 of SEQ ID NO: 1. The epitope of said antibody may further comprise the F48 of SEQ ID NO: 1.

The definition of the term "paratope" is derived from the above definition of "epitope" by reversing the perspective. Thus, the term "paratope" refers to the area or region on the antibody to which an antigen specifically binds, i.e. with which it makes physical contact to the antigen.

In the context of an X-ray derived crystal structure, defined by spatial coordinates of a complex between an antibody, such as a Fab fragment, and its antigen, the term paratope is herein, unless otherwise specified or contradicted by context, specifically defined as antigen residues characterized by having a heavy atom (i.e. a non-hydrogen atom) within a distance of 4 Å from a heavy atom in TREM-1.

The epitope and paratope for a given antibody (Ab)/antigen (Ag) pair may be identified by routine methods. For example, the general location of an epitope may be determined by assessing the ability of an antibody to bind to different fragments or variant TREM-1 polypeptides. The specific amino acids within TREM-1 that make contact with an antibody (epitope) and the specific amino acids in an antibody that make contact with TREM-1 (paratope) may also be determined using routine methods. For example, the antibody and target molecule may be combined and the Ab:Ag complex may be crystallised. The crystal structure of the complex may be determined and used to identify specific sites of interaction between the antibody and its target.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

An antibody of the invention may compete with mAb 0170 for binding to human TREM-1. An antibody of the invention may compete with mAb 0170 for binding to cynomolgus monkey TREM-1. In other words, an antibody of the invention may belong to the same "bin" as mAb 0170.

The term "binding affinity" herein refers to a measurement of the strength of a non-covalent interaction between two molecules, e.g. an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

An antibody of the invention may bind human TREM-1 with an affinity ($K_D$) that is $1\times10^{-7}$ M or less, $1\times10^{-8}$ M or less, or $1\times10^{-9}$ M or less, or $1\times10^{-10}$ M or less, $1\times10^{-11}$ M or less, $1\times10^{-12}$ M or less or $1\times10^{-13}$ M or less, as determined using surface plasmon resonance. An antibody of the invention may bind cynomolgus monkey TREM-1 with an affinity ($K_D$) that is $1\times10^{-7}$ M or less, $1\times10^{-8}$ M or less, or $1\times10^{-9}$ M or less, $1\times10^{-10}$ M or less, $1\times10^{-11}$ M or less, $1\times10^{-12}$ M or less or $1\times10^{-13}$ M or less, as determined using surface plasmon resonance.

The term "binding specificity" herein refers to the interaction of a molecule such as an antibody, or fragment thereof, with a single exclusive antigen, or with a limited number of highly homologous antigens (or epitopes). In contrast, antibodies that are capable of specifically binding to TREM-1 are not capable of binding dissimilar molecules. Antibodies according to the invention may not be capable of binding Nkp44, the Natural killer cell p44-related protein.

The specificity of an interaction and the value of an equilibrium binding constant can be determined directly by well-known methods. Standard assays to evaluate the ability of ligands (such as antibodies) to bind their targets are known in the art and include, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

In another aspect, the present invention provides compositions and formulations comprising molecules of the invention, such as the TREM-1 antibodies, polynucleotides, vectors and cells described herein. For example, the invention provides a pharmaceutical composition that comprises one or more TREM-1 antibodies of the invention, formulated together with a pharmaceutically acceptable carrier.

Accordingly, one object of the invention is to provide a pharmaceutical formulation comprising such a TREM-1 antibody which is present in a concentration from 0.25 mg/ml to 250 mg/ml, such as a concentration of from 10 to 200 mg/ml, and wherein said formulation has a pH from 2.0 to 10.0, such as a pH of from 4.0 to 8.0. The formulation may further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, $19^{th}$ edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0, such as a pH of from 4.0 to 8.0.

The TREM-1 antibodies of the present invention and pharmaceutical compositions comprising such antibodies may be used for the treatment of inflammatory diseases such as the following: inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogrens's syndrome, autoimmune nephritis, Goodpasture's syndrome, chronic inflammatory demyelinating polyneuropathy, allergy, asthma and other autoimmune diseases that are a result of either acute or chronic inflammation.

TREM-1 antibodies of the invention may be suitable for use in the treatment of individuals with inflammatory bowel disease. Inflammatory Bowel Disease (IBD) is a disease that may affect any part of the gastrointestinal tract from mouth to anus, causing a wide variety of symptoms. IBD primarily causes abdominal pain, diarrhoea (which may be bloody), vomiting or weight loss, but may also cause complications outside of the gastrointestinal tract such as skin rashes, arthritis, inflammation of the eye, fatigue and lack of concentration. Patients with IBD can be divided into two major classes, those with ulcerative colitis (UC) and those with Crohn's disease (CD). CD generally involves the ileum and colon, it can affect any region of the intestine but is often discontinuous (focused areas of disease spread throughout the intestine). UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

TREM-1 antibodies of the invention may be suitable for use in the treatment of individuals with rheumatoid arthritis. Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain, among other physiologic effects. The involved joint can lose its shape and alignment, resulting in pain and loss of movement.

There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

TREM-1 antibodies of the invention may be suitable for use in the treatment of individuals with psoriasis. Psoriasis is a T-cell mediated inflammatory disorder of the skin that can cause considerable discomfort. It is a disease for which there is currently no cure and it affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+ T cells mimics many aspects of human psoriasis and therefore can be used to identify compounds suitable for use in treatment of psoriasis (Davenport et al., Internat. Immunopharmacol 2:653-672, 2002). Efficacy in this model is a measured by reduction in skin pathology using a scoring system. Similarly, efficacy in patients is measured by a decrease in skin pathology.

TREM-1 antibodies of the invention may be suitable for use in the treatment of individuals with psoriatic arthritis. Psoriatic arthritis (PA) is a type of inflammatory arthritis that occurs in a subset of patients with psoriasis. In these patients, the skin pathology/symptoms are accompanied by a joint swelling similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

The term "treatment", as used herein, refers to the medical therapy of any human or other animal subject in need thereof. Said subject is expected to have undergone physical examination by a medical or veterinary medical practitioner, who has given a tentative or definitive diagnosis which would indicate that the use of said treatment is beneficial to the health of said human or other animal subject. The timing and purpose of said treatment may vary from one individual to another, according to many factors, such as the status quo of the subject's health. Thus, said treatment may be prophylactic, palliative, symptomatic and/or curative.

In terms of the present invention, prophylactic, palliative, symptomatic and/or curative treatments may represent separate aspects of the invention.

An antibody of the invention may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

In a first aspect of the invention, the substitution of negatively charged residues of the CDR1 and CDR3 regions of SEQ ID NO: 3 (the variable light chain of mAb 0170) was observed to influence the viscosity of the mAb. In this first aspect of the invention, the mAb of the invention is a variant of mAb 0170 having a heavy chain and a light chain, wherein the light chain of mAb 0170, namely SEQ ID NO: 3, comprises mutations wherein negatively charged residues in CDR1 and CDR3 region of SEQ ID NO: 3 are substituted with uncharged residues. Accordingly, an aspect of the invention is directed to a variant of mAb 0170 comprising substituting any one or any combination of residues D1, D30, D33, D74, D98, E27, E97 of SEQ ID NO: 3 with an amino acid residue selected from the group consisting of glycine, alanine, serine, asparagine, glutamine, threonine, cysteine, and tyrosine. Otherwise stated, an interesting embodiment of the invention is directed to an antibody or fragment thereof comprising SEQ ID NO: 2 (or a variant thereof) as a heavy chain and as light chain comprising a variant of SEQ ID NO: 3 wherein any one or any combination of residues D1, D30, D33, D74, D98, E27, E97 of SEQ ID NO: 3 is mutated to an amino acid residue selected from the group consisting of glycine, alanine, serine, asparagine, glutamine, threonine, cysteine, and tyrosine. These mutations will be referred to as "charge patch" mutations. In a preferred embodiment, at least one or both of E27 and E97 of the CDR1 and CDR3 regions of SEQ ID NO: 3 are substituted with uncharged amino acid residues, such as an amino acid selected from the group consisting of glycine, alanine, serine, asparagine, glutamine, threonine, cysteine, and tyrosine. In a preferred embodiment, E27 of the CDR1 and CDR3 regions of SEQ ID NO: 3 is mutated to glutamine and E97 is substituted with an amino acid selected from the group consisting of glycine, alanine, serine, asparagine, glutamine, threonine, cysteine, and tyrosine, more preferably with an amino acid selected from the group consisting of serine and glutamine. In a further embodiment, E27 remains unmutated and E97 is mutated with an amino acid selected from the group consisting of glycine, alanine, serine, asparagine, glutamine, threonine, cysteine, and tyrosine, more preferably with an amino acid selected from the group consisting of serine and glutamine. In another embodiment, residue E97 remains unmutated and E27 is substituted with an amino acid selected from the group consisting of glycine, alanine, serine, asparagine, glutamine, threonine, cysteine, and tyrosine, more preferably with an amino acid selected from the group consisting of serine and glutamine.

Another aspect of the invention is based on the observation that Fab-Fab dimers were formed due to interactions in the paratope area. Since mAbs comprise two Fabs, it was envisioned that mAbs would be able to multimerize, which could have an impact on the viscosity properties. Thus, another aspect of the invention is directed to mutate residues in the Fab-Fab interaction area of SEQ ID NO: 2 (namely in the variable heavy chain area of mAb 0170) to reduce Fab-Fab dimerization. These mutations are referred to as "Fab-Fab interaction" mutations. Accordingly, an aspect of the invention is directed to substituting any one of residues Y32, R52, S55, S56, N57, A59, M102, I104 and R106 of SEQ ID NO: 2 or F32, D33, Y34, Y53, R54, D98 of SEQ. ID NO 3 with an amino acid residue selected from the group consisting of glycine, alanine, serine, asparagine, glutamine, threonine, cysteine, lysine, arginine, tryptophan, histidine and tyrosine. Otherwise stated, an interesting embodiment of the invention is directed to an antibody or fragment thereof comprising a variant of SEQ ID NO: 2 wherein any one of residues Y32, R52, S55, S56, N57, A59, M102, I104 and R106 of SEQ ID NO: 2 or F32, D33, Y34, Y53, R54, D98 of SEQ. ID NO 3 ("Fab-Fab interaction" mutations) is substituted with another amino acid, such as natural amino acid, preferably an amino acid residue selected from the group consisting of glycine, alanine, serine, asparagine, glutamine, threonine, cysteine, lysine, arginine, tryptophan, histidine and tyrosine. Preferably, at least one of residues A59 and N57 SEQ ID NO: 2 is mutated to an amino acid residue selected from the group consisting of glycine, alanine, serine, asparagine, glutamine, threonine, cysteine, lysine, arginine, tryptophan, histidine and tyrosine, more preferably serine or tyrosine. In one embodiment, A59 remains unmutated and N57 is mutated to an amino acid residue selected from the group consisting of glycine, alanine, serine, asparagine, glutamine, threonine, cysteine, lysine, arginine, tryptophan, histidine and tyrosine, more preferably serine or tyrosine. In another embodiment, N57 remains unmutated and A59 is mutated to an amino acid residue selected from the group consisting of glycine, alanine, serine, asparagine, glutamine, threonine, cysteine, lysine, arginine, tryptophan, histidine and tyrosine. In at least one embodiment, both A59 and N57 are mutated to an amino acid residue selected from the group consisting of glycine, alanine, serine, asparagine, glutamine, threonine, cysteine, lysine, arginine, tryptophan, histidine and tyrosine, more preferably serine or tyrosine.

In an interesting embodiment, i) at least one negatively charged residues of the CDR1 and CDR3 regions of SEQ ID NO: 3 is mutated to an amino acid residue selected from the group consisting of glycine, alanine, serine, asparagine, glutamine, threonine, cysteine, and tyrosine and ii) at least one residue of residues Y32, R52, S55, S56, N57, A59, M102, I104 and R106 of SEQ ID NO: 2 or F32, D33, Y34, Y53, R54, D98 of SEQ. ID NO 3 ("Fab-Fab interaction" mutations) is mutated to an amino acid residue selected from the group consisting of glycine, alanine, serine, asparagine, glutamine, threonine, cysteine, lysine, arginine, and tryptophan, histidine and tyrosine.

In a suitable embodiment, one or both of E27 and E97 of SEQ ID NO: 3 is/are mutated to an amino acid residue selected from the group consisting of glycine, alanine, serine, asparagine, glutamine, threonine, cysteine, and tyrosine and one or both of A59 and N57 of SEQ ID NO: 2 is/are mutated to an amino acid residue selected from the group consisting of glycine, alanine, serine, asparagine, glutamine, threonine, cysteine, lysine, arginine, tryptophan, histidine and tyrosine, more preferably serine or tyrosine.

A further aspect of the invention is based on the observation that an Ala substitution in position Y90 of SEQ. ID NO 1 of TREM-1 improved the affinity of SEQ. ID NO 3 to TREM-1. The Y90 was found to interact with a phenylalanine residue of SEQ ID NO: 3. Mutation of SEQ ID NO: 3 in order to improve the Fab-TREM-1 interaction are referred to as Fab-TREM-1 interaction mutations. In one embodiment of this aspect of the invention, phenylalanine at position 32 of SEQ ID NO: 3 is mutated to an amino acid selected from amino acid residues glycine, serine, threonine, cysteine, alanine, valine, leucine, isoleucine and methionine, preferably selected from alanine, glycine, serine valine and leucine. In an interesting embodiment, F32 of SEQ ID NO: 3 is mutated to alanine or serine.

Figure 6:
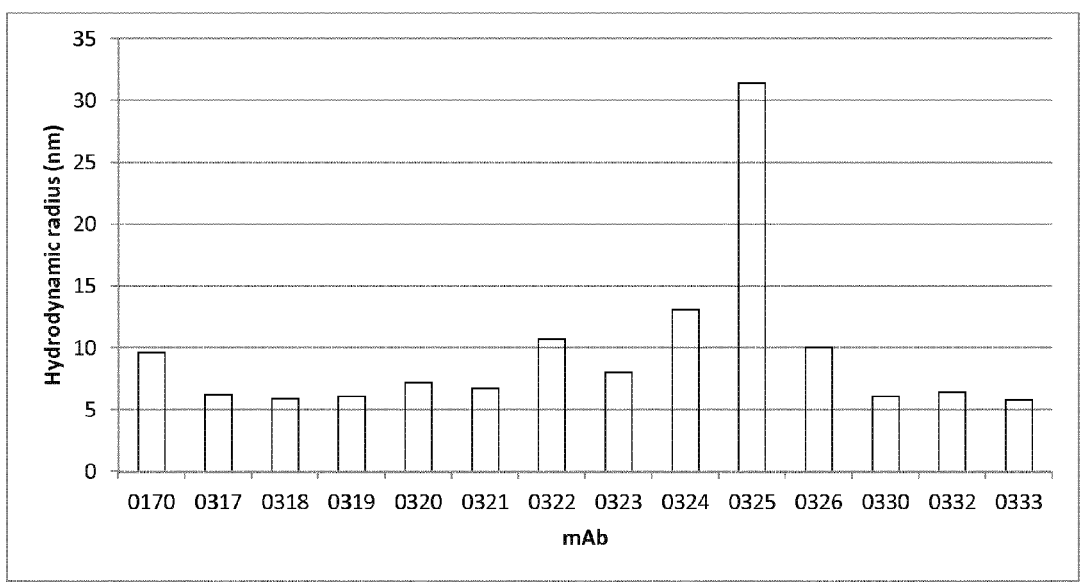
FIG. 6 depicts the hydrodynamic radius of the anti-TREM-1 mAb variants compared to mAb 0170.

Charge patch mutations in the CDR1 and CDR3 of SEQ ID NO: 3 reduced the hydrodynamic radius (Rh) while mutations in the Fab-Fab interaction region increased Rh (FIG. 6). Mutations in the "Fab-TREM-1 interaction" site did not influence Rh and had very little effect on viscosity (FIGS. 6 and 1, Tables 3C and 3E).

TABLE 1

Overview of SEQ ID No (0170) mAb variants generated.
L = light chain, H = heavy chain.

| | mAb ID | Comprise Sequence ID No. | Mutation(s) to SEQ ID NO: 2 or 3 | Chain |
|---|---|---|---|---|
| Charge patch mutations | 0317 | SEQ ID NO: 4 and 2 | E27Q, E97S | L |
| | 0318 | SEQ ID NO: 5 and 2 | E27Q, E97Q | L |
| | 0319 | SEQ ID NO: 6 and 2 | E97S | L |
| | 0320 | SEQ ID NO: 7 and 2 | E97Q | L |
| | 0321 | SEQ ID NO: 8 and 2 | E27Q | L |

TABLE 1-continued

Overview of SEQ ID No (0170) mAb variants generated.
L = light chain, H = heavy chain.

| | mAb ID | Comprise Sequence ID No. | Mutation(s) to SEQ ID NO: 2 or 3 | Chain |
|---|---|---|---|---|
| Fab-Fab interaction mutations | 0324 | SEQ ID NO: 11 and 3 | A59Y | H |
| | 0325 | SEQ ID NO: 12 and 3 | N57S | H |
| | 0326 | SEQ ID NO: 13 and 3 | A59Y, N57S | H |
| Fab-TREM-1 interaction mutations | 0322 | SEQ ID NO: 9 and 2 | F32A | L |
| | 0323 | SEQ ID NO: 10 and 2 | F32S | L |
| Charge patch and Fab-TREM-1 interaction mutations | 0330 | SEQ ID NO: 14 and 2 | F32A, E27Q, E97Q | L |
| Charge patch and Fab-Fab interaction mutations | 0332 | SEQ ID NO:: 15 and 5 | A59Y/E27Q, E97Q | H/L |
| Charge patch, Fab-TREM-1 interaction and Fab-Fab interaction | 0333 | SEQ ID NO: 14 and 16 | A59Y/F32A, E27Q, E97Q | H/L |

The viscosity was determined for the mAb 0170 variants by DLS or micro rheology and showed that both "charge patch" mutations and "Fab-Fab interaction" mutations reduced the viscosity. The mAb variant 0318, which comprise the charge patch mutations E27Q and E97Q was found to have the lowest viscosity.

The binding kinetics of the mAb 0170 variants towards human TREM-1-Fc and cynomolgus TREM-1-Fc were determined, respectively. The mAb 0170 variants were all found to have similar affinity towards human TREM-1-Fc. Interestingly, the mAb variant, SEQ ID NO: 9 comprising a "Fab-TREM-1 interaction" mutation was found to have increased affinity towards cynomolgus TREM-1-Fc (Table 2).

TABLE 2

Affinity of anti-TREM-1 mAb variants towards human TREM-1-Fc and cynomolgus TREM-1-Fc respectively.

| | Human TREM-1-Fc | | | Cynomolgus TREM-1-Fc | | |
|---|---|---|---|---|---|---|
| mAb | ka (1/Ms) | kd (1/s) | KD (nM) | ka (1/Ms) | kd (1/s) | KD (nM) |
| 0170 | 3E+06 | 5E−04 | 0.1 | 0.3E+06 | 4E−04 | 2 |
| 0317 | 4E+06 | 6E−04 | 0.2 | 0.3E+06 | 7E−04 | 3 |
| 0318 | 3E+06 | 7E−04 | 0.2 | 0.3E+06 | 7E−04 | 2 |
| 0319 | 4E+06 | 6E−04 | 0.2 | 0.3E+06 | 6E−04 | 2 |
| 0320 | 4E+06 | 7E−04 | 0.2 | 0.2E+06 | 6E−04 | 3 |
| 0321 | 3E+06 | 6E−04 | 0.2 | 0.3E+06 | 6E−04 | 2 |
| 0322 | 3E+06 | 3E−04 | 0.1 | 0.6E+06 | 1E−04 | 0.1 |
| 0323 | 2E+06 | 6E−04 | 0.3 | 0.4E+06 | 2E−04 | 0.6 |
| 0324 | 3E+06 | 8E−04 | 0.3 | 0.2E+06 | 6E−04 | 4 |

TABLE 2-continued

Affinity of anti-TREM-1 mAb variants towards human TREM-1-Fc and cynomolgus TREM-1-Fc respectively.

| | Human TREM-1-Fc | | | Cynomolgus TREM-1-Fc | | |
|---|---|---|---|---|---|---|
| mAb | ka (1/Ms) | kd (1/s) | KD (nM) | ka (1/Ms) | kd (1/s) | KD (nM) |
| 0325 | 4E+06 | 3E−04 | 0.08 | 0.2E+06 | 6E−04 | 1 |
| 0326 | 3E+06 | 7E−04 | 0.2 | 0.2E+06 | 3E−04 | 5 |
| 0330 | 2E+06 | 3E−04 | 0.1 | 0.6E+06 | 7E−05 | 0.1 |
| 0332 | 3E+06 | 1E−03 | 0.4 | 0.2E+06 | 8E−04 | 4 |
| 0333 | 2E+06 | 5E−04 | 0.3 | 0.4E+06 | 1E−04 | 0.3 |

In an embodiment with both improved affinity towards TREM-1 and having low viscosity, the mutations from SEQ ID NO: 9 were combined with the mutations in SEQ ID NO: 5 to generate the light chain from SEQ ID NO: 14 and the mutations from the light chain from SEQ ID NO: 14 were further combined with the heavy chain mutations from SEQ ID NO: 16. The increased affinity towards cynomolgus TREM-1-Fc was retained for the mAb variants comprising the combined mutations of SEQ ID NO: 14 and the mutations did not negatively affect the affinity towards human TREM-1-Fc. Accordingly, embodiments comprising both "charge patch" mutations and "Fab-TREM-1 interaction" mutations are envisaged by the present invention, as well as embodiments comprising both "charge patch" mutations and "Fab-Fab interaction" mutations as well as embodiments comprising both "Fab-Fab interaction" mutations and "Fab-TREM-1 interaction" mutations and embodiments comprising "Fab-Fab interaction" mutations, "Fab-TREM-1 interaction" mutations and "charge patch" mutations.

TABLE 3A

Viscosity versus protein concentrations of mAb 0170, 0317 and 0318

| mAb | | | | | |
|---|---|---|---|---|---|
| 0170 | | 0317 | | 0318 | |
| Protein concentration (mg/mL) | Viscosity (cP) | Protein concentration (mg/mL) | Viscosity (cP) | Protein concentration (mg/mL) | Viscosity (cP) |
| 100.0 | 26.0 | 85.0 | 2.9 | 85.0 | 1.9 |
| 80.0 | 14.5 | 63.8 | 2.2 | 63.8 | 1.9 |
| 60.0 | 6.0 | 42.5 | 1.9 | 42.5 | 2.0 |
| 40.0 | 3.1 | 17.0 | 1.3 | 17.0 | 1.2 |
| 20.0 | 1.6 | 10.2 | 1.2 | 10.2 | 1.2 |

TABLE 3A-continued

Viscosity versus protein concentrations of mAb 0170, 0317 and 0318

| mAb | | | | | |
|---|---|---|---|---|---|
| 0170 | | 0317 | | 0318 | |
| Protein concentration (mg/mL) | Viscosity (cP) | Protein concentration (mg/mL) | Viscosity (cP) | Protein concentration (mg/mL) | Viscosity (cP) |
| 12.0 | 1.3 | 3.4 | 1.1 | 3.4 | 1.2 |
| 4.0 | 1.1 | 0.0 | 1.0 | 0.0 | 1.0 |
| 0.0 | 0.9 | | | | |

TABLE 3B

Viscosity versus protein concentrations of mAb 0319 and 0320 and 321.

| mAb | | | | | |
|---|---|---|---|---|---|
| 0319 | | 0320 | | 0321 | |
| Protein concentration (mg/mL) | Viscosity (cP) | Protein concentration (mg/mL) | Viscosity (cP) | Protein concentration (mg/mL) | Viscosity (cP) |
| 85.0 | 2.2 | 107.0 | 7.8 | 106.0 | 5.9 |
| 63.8 | 2.3 | 80.3 | 3.7 | 79.5 | 3.0 |
| 42.5 | 2.0 | 53.5 | 2.5 | 53.0 | 2.0 |
| 17.0 | 1.2 | 26.8 | 1.6 | 26.5 | 1.6 |
| 10.2 | 1.1 | 13.4 | 1.3 | 13.3 | 1.2 |
| 3.4 | 1.1 | 6.7 | 1.2 | 6.6 | 1.1 |
| 0.0 | 1.0 | 3.3 | 1.1 | 3.3 | 1.1 |
| | | 0.0 | 1.0 | 0.0 | 0.9 |

TABLE 3C

Viscosity versus protein concentrations of mAb 0322, 0323 and 324.

| mAb | | | | | |
|---|---|---|---|---|---|
| 0322 | | 0323 | | 0324 | |
| Protein concentration (mg/mL) | Viscosity (cP) | Protein concentration (mg/mL) | Viscosity (cP) | Protein concentration (mg/mL) | Viscosity (cP) |
| 100.0 | 16.4 | 101.0 | 21.3 | 103.0 | 5.4 |
| 75.0 | 4.9 | 75.8 | 11.3 | 77.3 | 3.1 |
| 50.0 | 3.3 | 50.5 | 3.7 | 51.5 | 2.2 |
| 25.0 | 2.0 | 25.3 | 2.6 | 25.8 | 1.6 |
| 12.5 | 1.6 | 12.6 | 2.0 | 12.9 | 1.4 |
| 6.3 | 1.4 | 6.3 | 1.4 | 6.4 | 1.3 |
| 3.1 | 1.3 | 3.2 | 1.2 | 3.2 | 1.2 |
| 0.0 | 1.0 | 0.0 | 1.0 | 0.0 | 0.9 |

TABLE 3D

Viscosity versus protein concentrations of mAb 0325, 0326 and 0330.

| mAb | | | | | |
|---|---|---|---|---|---|
| 0325 | | 0326 | | 0330 | |
| Protein concentration (mg/mL) | Viscosity (cP) | Protein concentration (mg/mL) | Viscosity (cP) | Protein concentration (mg/mL) | Viscosity (cP) |
| 95.0 | 7.8 | 109.0 | 7.5 | 104.5 | 3.8 |
| 71.3 | 3.7 | 81.8 | 3.1 | 50.5 | 2.1 |
| 47.5 | 2.3 | 54.5 | 2.2 | 23.9 | 1.4 |

TABLE 3D-continued

Viscosity versus protein concentrations of mAb 0325, 0326 and 0330.

| mAb | | | | | |
|---|---|---|---|---|---|
| 0325 | | 0326 | | 0330 | |
| Protein concentration (mg/mL) | Viscosity (cP) | Protein concentration (mg/mL) | Viscosity (cP) | Protein concentration (mg/mL) | Viscosity (cP) |
| 23.8 | 1.6 | 27.3 | 1.6 | 9.4 | 1.3 |
| 11.9 | 1.3 | 6.8 | 1.5 | 4.7 | 1.1 |
| 5.9 | 1.3 | 3.4 | 1.1 | 1.9 | 1.1 |
| 3.0 | 1.2 | 0.0 | 0.9 | 1.0 | 1.3 |
| 0.0 | 1.0 | | | | |

TABLE 3E

Viscosity versus protein concentrations of mAb 0332 and 0333.

| mAb | | | |
|---|---|---|---|
| 0332 | | 0333 | |
| Protein concentration (mg/mL) | Viscosity (cP) | Protein concentration (mg/mL) | Viscosity (cP) |
| 114.1 | 5.9 | 113.2 | 5.2 |
| 53.6 | 2.1 | 47.1 | 2.1 |
| 22.2 | 2.2 | 24.9 | 2.0 |
| 9.0 | 2.2 | 9.0 | 1.8 |
| 4.6 | 1.8 | 4.5 | 1.5 |
| 1.9 | 1.2 | 1.8 | 1.6 |
| 1.1 | 1.1 | 0.9 | 1.4 |

Non-limiting embodiments of the present invention further comprise:

1. An antibody or fragment thereof that is capable of binding to and blocking TREM-1 of SEQ ID NO: 1, characterized in that the antibody, or an antibody fragment of said antibody, has a viscosity of less than 5 cP at a concentration of 50 mg/mL, such as less than 4 cP, preferably less than 3 cP (wherein the method of determining viscosity versus protein concentration conditions are conventional or as described herein.)

2. An antibody or fragment thereof that is capable of binding to and blocking TREM-1, characterized in that the antibody, or an antibody fragment of said antibody, has a viscosity of less than 5 cP at a concentration of 80 mg/mL, preferably less than 4 cP (wherein the method of determining viscosity versus protein concentration conditions are conventional or as described herein.)

3. An antibody or fragment thereof according to embodiments 1 or 2 wherein the antibody or fragment thereof blocks TREM-1 function with a KD to SEQ ID NO: 1 of less than 0.5 nM, such as less than 0.4 nM, preferably of 0.3 nM or less.

4. An antibody or fragment thereof wherein the antibody or fragment thereof competitively binds with mAb 0170 for binding to SEQ ID NO: 1 and has a viscosity profile such that:
(a) the antibody or an antibody fragment of said antibody has a viscosity of less than 5 cP at a concentration of 50 mg/mL, such as less than 4 cP, preferably less than 3 cP; or
(b) the antibody or an antibody fragment of said antibody, has a viscosity of less than 5 cP at a concentration of 80 mg/mL, preferably less than 4 cP.

5. An antibody or fragment thereof that is capable of specifically binding to and blocking TREM-1, wherein the antibody or fragment thereof has "Fab-Fab interaction" mutations of SEQ ID NO: 2.

6. An antibody or fragment thereof that is capable of specifically binding to and blocking TREM-1 of SEQ ID NO: 1, wherein the antibody or fragment thereof has "charge patch" mutations, such as wherein at least one of the negatively charged residues of the CDR1 and CDR3 of SEQ ID NO: 3 are substituted with uncharged residues.

7. An antibody or fragment thereof according to any of the embodiments of the invention wherein negatively charged amino acids are substituted with amino acid residues which can form hydrogen bonding partners, such as mutation of an Asp or Glu residue to any one of Asn, Gln, Ser and Thr.

8. An antibody or fragment thereof according to any of the embodiments of the invention having a lowered viscosity compared to mAb 0170, but still having a $K_D$ to SEQ ID NO: 1 of less than 0.5 nM.

9. An antibody or fragment thereof according to any of the embodiments of the invention having a lowered viscosity compared to mAb 0170, a $K_D$ to SEQ ID NO: 1 of less than 0.5 nM and a $K_D$ to SEQ ID NO: 17 of less than 0.6 nM, by substituting uncharged amino acids of SEQ ID NO: 2 and/or 3, involved in specific "Fab-Fab interactions" with amino acids with altered size or hydrogen bonding potential.

10. An antibody or fragment thereof according to any of the embodiments of the invention that is capable of specifically binding to and blocking TREM-1 of SEQ ID NO: 1 and comprises variants of SEQ ID NO: 2 or SEQ ID NO: 3 or both, wherein the variants are selected from the group consisting of "Fab-Fab interaction" mutations, "Fab-TREM-1 interaction" mutations and "charge-patch" mutations of SEQ ID NO: 2 or SEQ ID NO: 3.

11. An antibody or fragment thereof according to any of the embodiments of the invention comprising "Fab-TREM-1 interaction" mutations, such as wherein a Phe residue of SEQ ID NO: 3 is substituted with Ala or Ser.

12. An antibody or fragment thereof according to any of the embodiments of the invention which competes with SEQ ID NO: 2 or 3 for binding to SEQ ID NO: 1 and which has an epitope comprising one, two, three, four, five, six, seven or all of the amino acid residues D38, V39, K40, C41, D42, Y43, T44 and L45 and one, two or all of the amino acid residues E46, K47, F48 of SEQ ID NO: 1.

13. The antibody or fragment thereof according to any of the embodiments of the invention, which competes for binding with SEQ ID NO: 3, and comprising a LC having one or both glutamate (E) residues of positions 27 and 97 of SEQ ID NO: 3 mutated to serine (S) or glutamine (Q), such as wherein E27Q, E97S, such as wherein both E27 and E97 are mutated to glutamine or wherein E27 remains un-mutated and E97 is mutated to S (E27, E97S), or wherein E27 remains un-mutated and E97 is mutated to Q (E27, E97Q), or wherein E97 remains un-mutated and E27 is mutated to Q or S, more preferably to Q (E27, E97Q).

14. The antibody or fragment thereof according to any of the embodiments of the invention comprising SEQ ID NO: 3, wherein the phenylalanine at position 32 (F32) is mutated, such as mutated to A (mAb 0322) or to S (mAb 0323).

15. The antibody or fragment thereof according to any one of the embodiments, comprising SEQ ID NO: 2 wherein one or both of residue N57 and residue A59 has been mutated, such as wherein residue A59 has been mutated to a tyrosine, or wherein residue N57 has been mutated to a serine, or wherein residue N57 has been mutated to a serine and residue A59 has been mutated to a tyrosine.

16. An antibody or fragment thereof comprising a variant of SEQ ID NO: 2 wherein uncharged amino acids involved in specific Fab-Fab interactions are substituted with amino acids with altered size or hydrogen bonding potential, such as wherein alanine (A) or asparagine (N) are substituted with any one of Ser, Thr, Phe, Tyr and Trp.

17. An antibody or fragment thereof comprising a variant of SEQ ID NO: 3 and which competes for binding with SEQ ID NO: 3 wherein one or both glutamate (E) residues of positions 27 and 97 of SEQ ID NO: 3 are mutated to serine (S) or glutamine (Q), such as wherein both E27 and E97 are mutated to glutamine (318), or wherein E27 remains un-mutated and E97 is mutated to S (E27, E97S), or wherein E27 remains un-mutated and E97 is mutated to Q (E27, E97Q), or wherein E97 remains un-mutated and E27 is mutated to Q or S, more preferably to Q (E27, E97Q).

18. An antibody or fragment thereof comprising a variant of SEQ ID NO: 2 and which competes for binding with SEQ ID NO: 2, wherein one or both of residue N57 and residue A59 has been mutated, such as wherein residue A59 has been mutated to a tyrosine, or wherein residue N57 has been mutated to a serine, or wherein both residue N57 has been mutated to a serine and residue A59 has been mutated to a tyrosine.

19. An antibody or fragment thereof comprising SEQ ID NO: 4.

20. An antibody or fragment thereof comprising SEQ ID NO: 5.

21. An antibody or fragment thereof comprising SEQ ID NO: 6.

22. An antibody or fragment thereof comprising SEQ ID NO: 7.

23. An antibody or fragment thereof comprising SEQ ID NO: 8.

24. An antibody or fragment thereof comprising SEQ ID NO: 9.

25. An antibody or fragment thereof comprising SEQ ID NO: 10.

26. An antibody or fragment thereof comprising SEQ ID NO: 11.

27. An antibody or fragment thereof comprising SEQ ID NO: 12.

28. An antibody or fragment thereof comprising SEQ ID NO: 13.

29. An antibody or fragment thereof comprising SEQ ID NO: 14.

30. An antibody or fragment thereof comprising SEQ ID NO: 15.

31. An antibody or fragment thereof comprising SEQ ID NO: 16.

32. An antibody or fragment thereof comprising any one of SEQ ID NOs: 4 to 16.

33. A composition comprising an antibody as defined in any of embodiments 1-32.

34. An antibody of the invention, such as of embodiment 1-32, for use as a medicament.

35. An antibody of the invention, such as of embodiment 1-32, for use in the treatment of a disease selected from an inflammatory disease or an autoimmune disease.

36. An antibody according to embodiment 35, wherein the disease is selected from the group consisting of rheumatoid arthritis and inflammatory bowel disease.

37. Use of an antibody of the invention, such as of any of embodiments 1-32, for the preparation of a medicament for the treatment of a disease selected from the group consisting of an inflammatory disease or an autoimmune disease.

38. The use according to embodiment 35 wherein the disease is selected from the group consisting of rheumatoid arthritis and inflammatory bowel disease.

39. A method of treating a disease selected from an inflammatory disease or an autoimmune disease comprising administering an antibody of the invention (such as an antibody of any of embodiments 1-32), a composition comprising the antibody of the invention, or a medicament comprising the antibody of the invention.

EXAMPLES

Example 1: Hydrodynamic Radius and Viscosity of mAb0170 Variants

The hydrodynamic radius of mAb0170 of WO2013/120553 was found to be higher (9-10 nm) than desired (5-6 nm). The hydrodynamic radius was determined by dynamic light scattering analysis using a 96-well plate setup with a DynaPro plate reader (Wyatt Inc.). The plates used were Corning 3540 assay plates (Corning). Total sample volume was approximately 20 µL and the temperature was kept at 25° C. for the mAb0170 variants (FIG. 6).

Charge patch mutations in the CDR1 and CDR3 of the variable light chain reduced the Rh to the level expected for monomeric mAbs while mutations in the Fab-Fab interaction region seemed to increase Rh. Mutations in the Fab-TREM-1 interaction site did not influence Rh.

The viscosity was determined for the mAb0170 variants 0317, 0318, 0319, 0320, 0321, 0322, 0323, 0324, 0325, 0326 and 0330 by DLS. Hydrodynamic radius was measured on a Wyatt DynaPro Platereader using Corning 3540 clear bottom, black not-treated polystyrene microplates and plain polystyrene nanospheres from Phosphorex Inc. with a mean diameter of 206.5 nm (Cat. no. 106). The protein samples were transferred to a Corning 3540 plate and covered with a top seal. The samples were centrifuged and the hydrodynamic radii of the protein samples were measured in the Wyatt DynaPro DLS plate reader. Each well was added 0.5 µL polystyrene beads and mixed gently by pipetting. The plate was centrifuged again and the hydrodynamic radii of the beads were measured in the Wyatt DynaPro DLS plate reader.

The viscosities of the protein samples were calculated as $$\text{viscosity(protein)} = (\text{hydrodynamic radius(beads, meas)} \times \text{viscosity(buffer)}) / \text{hydrodynamic radius(beads, real)}$$

where viscosity(protein) is the calculated viscosity of the protein solution, hydrodynamic radius(beads, meas) is the measured hydrodynamic radius of the polystyrene beads in the protein solution, viscosity(buffer) is the viscosity of the buffer and hydrodynamic radius(beads, real) is the real mean diameter of the beads [He et al., Anal Biochem, 399, 141-143, 2010].

The viscosity was determined by micro-rheology for the mAb0170 variants 0332 and 0333. For the rheological analysis, a 250 μl Hamilton LT syringe (Hamilton-Bonaduz Inc) with a 30G Novofine needle attached was used. The syringe was placed in a custom made aluminium holder fastened to a platform. The plunger of the syringe was driven by a TAXTPlus Texture Analyzer, which measured the resulting force on the plunger with a pre-determined injection speed. Each sample was tested with three different injection speeds. The cross-head speed and the measured force were used to calculate the shear rate and the shear stress respectively. Viscosity can be expressed in relation to shear rate as:

$$\eta_{protein} = \tau_W / \gamma = (\Delta P D/4L)/((32Q)/(\pi D^3))$$

where $\eta_{protein}$ is the viscosity of the protein solution, $\gamma$ is the apparent shear rate, $\tau_W$ is the shear stress, P is the pressure resulting from driving the plunger, Q is the volumetric flow rate of the fluid passing through the capillary needle and D and L are the internal diameter and length, respectively of the capillary (Allahham et al., 2004; Intl 3 Pharm 270, 139-148). The viscosity, $\eta_{protein}$ was calculated from the know values of D, L and Q and the measured value of P.

The analysis showed that both "charge patch" mutations and "Fab-Fab interaction" mutations reduced the viscosity (FIG. 1). The mAb variant SEQ ID NO: 5, which comprises the charge patch mutations E27Q and E97Q was found to have the lowest viscosity.

Example 2: Kinetics of mAb0170 Variants

The binding kinetics of the mAb 0170 variants towards human TREM-1-Fc and cynomolgus TREM-1-Fc were determined, respectively. Binding studies were performed on a ProteOn Analyzer (BioRad) that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in the six parallel flow cells. Anti-human Fc monoclonal or anti-murine Fc polyclonal antibody from Biacore human or mouse Fc capture kits were immobilized in horizontal direction onto flow cells of a GLM sensor chip according to the manufacturer's instructions. The final immobilization level of capture antibody was approximately 2600-6000 RU in each experiment. The capture of purified monoclonal mouse or recombinantly expressed anti-hTREM-1 antibodies was conducted by diluting the antibodies to 5-10 nM into running buffer (10 mM Hepes 0.15 M NaCl, 5 mM EDTA, 0.05% surfactant P20, pH 7.4) followed by injection in vertical direction at 30 μL/min for 60 sec, creating reference interspots adjacent to all flow cells with only anti-Fc antibody immobilized. This typically resulted in final capture levels of test antibodies of approximately 100-300 RU and Rmax values of analyte of 30-90 RU. Binding of hTREM-1 or cTREM-1 proteins was conducted by injecting analyte (antigen) over all flow cells in horizontal direction to allow for comparative analyses of binding to different captured anti-TREM-1 antibodies relative to binding to the reference interspot. hTREM-1 or cTREM-1 proteins were diluted serially 1:3 to 1.2-100 nM or into running buffer, injected at 100 μL/min for 250 s and allowed to dissociate for 600s. The GLM surface was regenerated after each injection cycle of analyte via two 18 s injections of 10 mM Glycine, pH 1.7 and 50 mM NaOH at 100 μL/min. This regeneration step removed the anti-TREM-1 antibody and any bound TREM-1 protein from the immobilized capture antibody surface and allowed for the subsequent binding of the next interaction sample pair. The regeneration procedure did not remove the directly immobilized anti-Fc capture antibody from the chip surface.

Binding affinity between antibodies and the antigen was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by fitting data to 1:1 Langmuir model using the ProteOn evaluation software for data analysis. $K_D$ is related to $k_a$ and $k_d$ through the equation $K_D = k_d/k_a$.

Binding curves were processed by double referencing (subtraction of reference surface signals as well as blank buffer injections over captured anti-TREM-1 antibodies) prior to data analysis. This allowed correction for instrument noise, bulk shift and drift during sample injections.

The mAb 0170 variants were all found to have similar affinity towards human TREM-1-Fc as mAb 0170. Interestingly, mAb variants comprising a "Fab-TREM-1 interaction" mutation, such as mAb 0322, had increased affinity towards cynomolgus TREM-1-Fc (Table 2).

Example 3: Kinetics and Viscosity of mAb 0330 and mAb 0333

In the attempt to generate a mAb with both improved affinity towards cynomolgus TREM-1 and having low viscosity, the mutations from SEQ ID NO 9 was combined with the mutations in SEQ ID NO 5, which was found to have the lowest viscosity among the mAb0170 variants and with SEQ ID NO: 11, which was found to have a modest effect on the viscosity. The increased affinity towards cynomolgus TREM-1-Fc was retained for the mAb variant comprising the combined mutations (mAb 0330 and mAb 0333) and the mutations did not affect the affinity towards human TREM-1-Fc. The viscosity of mAb0330 and mAb 0333 were markedly reduced compared to mAb 0170 of WO2013/120553 (FIG. 1).

Example 4: Cultivation of a BWZ'36/hTREM-1 Stable Cell Line

BWZ/hTREM-1 reporter cell were cultured in RPMI 1640 w/o phenol red (Cat #11835, Gibco, Carlsbad CA, USA), supplemented with 10% FCS (Cat #16140-071, Gibco, New York, USA), 1% Pen/Strep (Cat #15070-06, Gibco), 1 mM Sodium Pyruvate (Cat #11360, Gibco), 5 μM –2ME (Cat #31350-010, Gibco) and 2 mM L-Glutamine (Cat #25030, Gibco). No special plates or coating was required. 10 ml Versene (Cat #15040, Gibco) was added to detach the cells which then were transferred to tubes, centrifuged 1200 rpm 5 min and washed in fresh RPMI 1640 w/o phenol red. These cells were then ready to use in an assay or re-culture for further propagation.

Example 5: Functional Characterization mAb 0170 Variants

The ability of the anti-TREM-1 mAb 0170 variants to inhibit human TREM-1 signalling was determined using a reporter cell line (BWZ'36/hTREM-1) provided by Bioxell. The reporter cell line was stimulated with PGN and TREM-1 ligand PGLYRP1 either as recombinant protein or expressed by activated neutrophils prior to incubation with mAbs. The potency of the variants to inhibit TREM-1 signalling was found to be clinical relevant and on par with that of the mAb 0170 of WO2013/120553 (FIGS. 2A-2E).

Figures 3A, 3B:
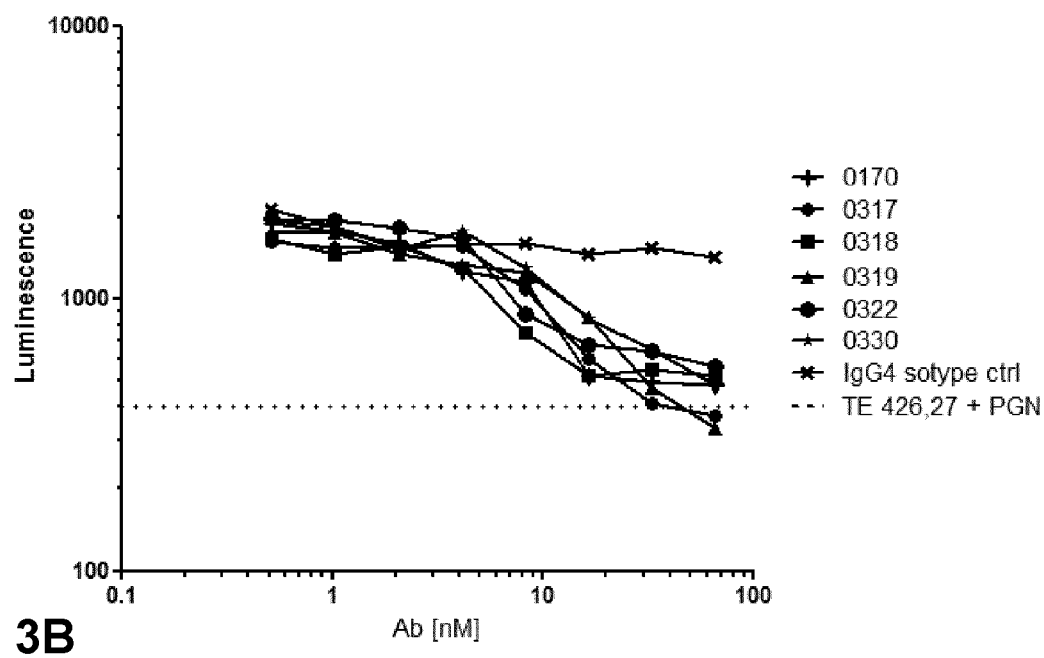
FIGS. 3A and 3B depict the ability of mAb 0170 variants to inhibit cynomolgus TREM-1 signalling in cynomolgus TREM-1 reporter cell line (TE426.27) stimulated with PGN and recombinant PGLYRP1.

Likewise, the ability to inhibit cynomolgus TREM-1 signalling was determined for the three mAb0170 variants with the lowest viscosity and two variants observed to have increased affinity towards cynomolgus TREM-1. In this assay using an established reporter cell line TE 426.27, similar potencies of the mAb variants and mAb0170 of WO2013/120553 was observed (FIGS. 3A-3B).

Figure 4:
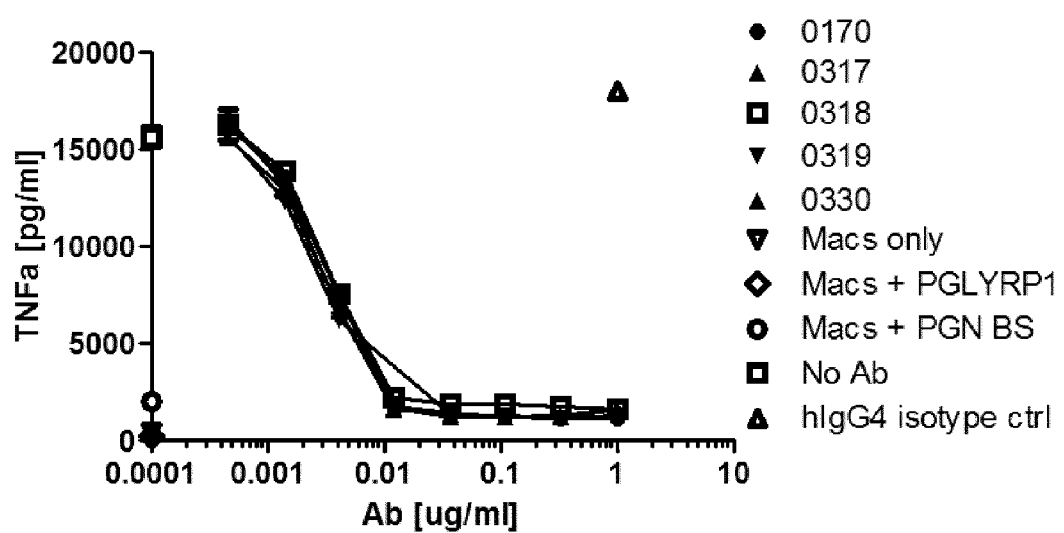
FIG. 4 depicts the ability of mAb 0170 variants to inhibit TNFa release from hypoxic M2 macrophages stimulated with PGN and recombinant PGLYRP1.
Figure 5:
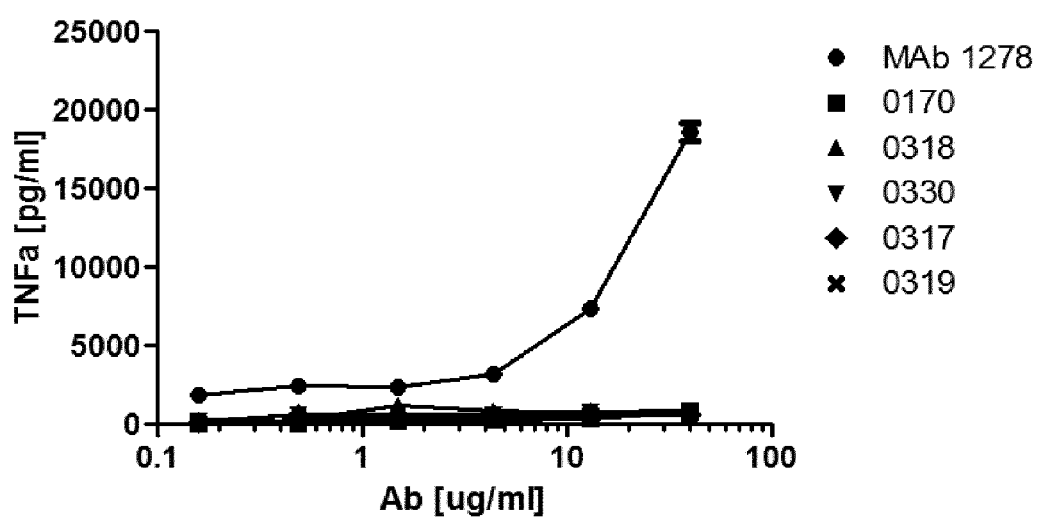
FIG. 5 depicts the agonistic potential of plate-bound of mAb 0170 variants to induce TNF release from hypoxic M2 macrophages. MAb 1278 (R&D) was used as positive control.

Also, the potency of the mAb variants to block TNFa release from primary cells from healthy donors was assessed. In this assay monocytes were differentiated to M2 macrophages under hypoxic conditions in order to increase TREM-1 expression and activated with PGN and recombinant PGLYRP1 prior to incubation with mAb. The mAb variants were found to be as potent as 0170 at inhibiting TREM-1-mediated TNFa release from hypoxic M2 macrophages (FIG. 4).

Example 6 Crystal Structure of a Fab 0170-Fab 0170 Complex

The potential of mAb 0170 molecules to interact by specific self-interactions were evaluated from by crystallographic analysis of a Fab 0170-Fab 0170 crystal structure.

Materials: The Fab region of mAb 0170 (SEQ ID NO: 18 and SEQ ID NO: 19) in a buffer consisting of 10 mM phosphate, 2.68 mM KCl, 140 mM NaCl, pH 7.4 at a protein concentration of 8.5 mg/mL.

Methods: The Fab region of mAb 0170 was crystallized in a hanging drop vapour diffusion experiment by equilibration of a droplet consisting of 2 µL protein solution mixed with 2 µL reservoir solution against a 0.5 mL reservoir composed of 20% (w/v) PEG 8000, 200 mM $K_2HPO_4$. The crystal was transferred to a drop consisting of 2 µL 35% (w/v) PEG3350, 200 mM $K_2HPO_4$ and mounted in a 0.2 mm diameter litholoop (Molecular Dimensions Limited) and flash-cooled in liquid nitrogen.

X-ray diffraction data was collected at MAXLAB 911-2, Lund University, Sweden using a Cryo-stream operated at 100 K. The raw data images were indexed, integrated and scaled using the XDS program package (Kabsch, Acta Crystallogr. D66, 133-144 (2010)). The space group of the crystal was P2(1)2(1)2(1), with unit cell parameters, a=62.4 Å, b=110.9 Å, c=158.4 Å. Data were collected to a resolution of 2.40 Å. The structure was solved by molecular replacement using the Phenix software (Adams et al., Acta Crystallogr. D66, 213-221 (2010)) as implemented in the CCP4i program suite (Potterton et al., Acta Crystallogr. D59, 1131-1137 (2003)). The search models were structures of the heavy chain from the pdb entry 1AD0.pdb (85% identity) and the light chain from the pdb entry 2QRG (94% identity). Structure refinement was carried out using Refmac5 (Murshudov et al., Acta Crystallogr. D53, 240-255 (1997)) from the CCP4i program suite. Coot version 7 (Emsley et al., Acta Crystallogr. D66, 486-501 (2010)) was used for manual structure rebuilding and validation.

Results and Discussion

The crystal structure of the mAb 170 Fab region contained four Fab molecules in the asymmetric unit (heavy chains were labelled A and C, light chains were labelled B and D). The Fab molecules were packed as dimers with the antigen binding region of one Fab molecule interacting with the antigen binding region of another Fab molecule. It was not possible to include and refine the last cysteine from the SEQ ID NO: 19 in the crystal structure although it would be expected to be in disulphide bond with a Cys from SEQ ID NO: 18 from the heavy chain. There was some indication of excess 2Fo-Fc and Fo-Fc electron density in the area, and it is possible that the disulphide bond is present in a subset of the Fab molecules. There was not significant sigma weighted 2Fo-Fc electron density for residues G26, K78-N79, I104-R105 and S138-E141 from SEQ ID NO: 18 in chain A in the asymmetric unit and for E1, G26-F 27, M102-R105, S136-E141, S195-K200 from SEQ ID NO: 18 chain C in the other Fab molecule in the asymmetric unit. Significant sigma weighted 2Fo-Fc electron density was also missing for residues D30-Y34 from SEQ ID NO: 19 in chain D. These residues were not included in the crystal structure but were included in molecular interaction analysis of the Fab-Fab interface by superposition with the mAb 0170 fragment crystal structure from the WO2013/120553 disclosed humanized anti-TREM-1 mAb 0170 crystal structure.

The quality parameters of the mAb 0170 Fab fragment structure showed an overall R-factor of the structure=24% and the Free R-factor=30%. The overall correlation coefficient was 0.93 and the diffraction-component precision index, DPI=0.3 Å (Cruickshank, Acta Crystallogr. D55, 583-601 (1999)). The root-mean-square deviation of the bond lengths in the structure from ideal bond lengths=0.025 Å and the root-mean-square deviation from ideal bond angles=2.326° (Engh and Huber, Acta Crystallogr. A47, 392-400 (1991)).

Analysis of intermolecular distances was carried out using the program NCONT in the CCP4 program suite (Potterton et al., Acta Crystallogr. D59, 1131-1137 (2003)) with a cutoff of 4 Å for intermolecular distances (Table 4). The analysis showed amino acid residues N57 and A59 from SEQ ID NO: 2 to belong to the group of amino acids involved in Fab-Fab interactions in the crystal structure.

TABLE 4

Predicted Fab-Fab interactions based on superposition of the WO2013/120553 disclosed humanized anti-TREM-1 mAb 0170 crystal structure with the present observed mAb 0170 Fab region crystal structure.

| Source amino acids, Fab 1 (Chain A and B) | | Target amino acids, Fab 2 (Chain C and D) | |
|---|---|---|---|
| F32 | SEQ ID NO: 3 | Y32 | SEQ ID NO: 2 |
| F32 | SEQ ID NO: 3 | M102 | SEQ ID NO: 2 |
| D33 | SEQ ID NO: 3 | Y53 | SEQ ID NO: 3 |
| Y34 | SEQ ID NO: 3 | Y34 | SEQ ID NO: 3 |
| Y34 | SEQ ID NO: 3 | R54 | SEQ ID NO: 3 |
| D98 | SEQ ID NO: 3 | S55 | SEQ ID NO: 2 |
| R52 | SEQ ID NO: 2 | S55 | SEQ ID NO: 2 |
| R52 | SEQ ID NO: 2 | S56 | SEQ ID NO: 2 |
| S55 | SEQ ID NO: 2 | A59 | SEQ ID NO: 2 |
| S55 | SEQ ID NO: 2 | R52 | SEQ ID NO: 2 |
| S56 | SEQ ID NO: 2 | S56 | SEQ ID NO: 2 |
| N57 | SEQ ID NO: 2 | S56 | SEQ ID NO: 2 |
| N57 | SEQ ID NO: 2 | N57 | SEQ ID NO: 2 |
| N57 | SEQ ID NO: 2 | A59 | SEQ ID NO: 2 |
| A59 | SEQ ID NO: 2 | S55 | SEQ ID NO: 2 |
| A59 | SEQ ID NO: 2 | S56 | SEQ ID NO: 2 |
| A59 | SEQ ID NO: 2 | N57 | SEQ ID NO: 2 |
| I104 | SEQ ID NO: 2 | I104 | SEQ ID NO: 2 |
| I104 | SEQ ID NO: 2 | R106 | SEQ ID NO: 2 |
| R106 | SEQ ID NO: 2 | F32 | SEQ ID NO: 3 |

The invention claimed is:

1. An antibody or fragment thereof that is capable of binding to and blocking TREM-1, wherein:
   the antibody or fragment thereof has a viscosity of less than 5 cP at a concentration of 80 mg/mL; and
   the antibody or fragment thereof comprises a variant of SEQ ID NO: 3 wherein at least one or both of E27 and E97 of the CDR1 and CDR3 regions of SEQ ID NO: 3 is substituted with an amino acid residue selected from the group consisting of glycine, alanine, serine, asparagine, glutamine, threonine, cysteine, and tyrosine.

2. The antibody or fragment thereof of claim 1, wherein the antibody or fragment thereof has a viscosity of less than 4 cP at a concentration of 80 mg/mL.

3. The antibody or fragment thereof of claim 1, wherein E27 of SEQ ID NO: 3 is substituted with glutamine and E97 is substituted with an amino acid selected from the group consisting of glycine, serine, asparagine, glutamine, threonine, cysteine, and tyrosine.

4. The antibody or fragment thereof of claim 3, wherein E97 is substituted with an amino acid selected from the group consisting of serine and glutamine.

5. The antibody or fragment thereof of claim 1, wherein E97 of SEQ ID NO: 3 is substituted with glutamine and E27 is substituted with an amino acid selected from the group consisting of glycine, serine, asparagine, glutamine, threonine, cysteine, and tyrosine.

6. The antibody or fragment thereof of claim 5, wherein E27 is substituted with an amino acid selected from the group consisting of serine and glutamine.

7. The antibody or fragment thereof of claim 1, wherein E27 of SEQ ID NO: 3 remains unmutated and E97 is substituted with an amino acid selected from the group consisting of glycine, alanine, serine, asparagine, glutamine, threonine, cysteine, and tyrosine.

8. The antibody or fragment thereof of claim 7, wherein E97 is substituted with an amino acid selected from the group consisting of serine and glutamine.

9. The antibody or fragment thereof of claim 1, wherein E27 and E97 of SEQ ID NO: 3 are both substituted with glutamine.

10. The antibody or fragment thereof of claim 1, wherein E97 of SEQ ID NO: 3 remains unmutated and E27 is substituted with an amino acid selected from the group consisting of glycine, alanine, serine, asparagine, glutamine, threonine, cysteine, and tyrosine.

11. The antibody or fragment thereof of claim 10, wherein E27 is substituted with an amino acid selected from the group consisting of serine and glutamine.

* * * * *

SEQUENCE LISTING

<160> NUMBER OF SEQ ID NOS: 19

<210> SEQ ID NO 1
<211> LENGTH: 234
<212> TYPE: PRT
<213> ORGANISM: Homo sapiens

<400> SEQUENCE: 1

```
Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230
```

<210> SEQ ID NO 2
<211> LENGTH: 448
<212> TYPE: PRT
<213> ORGANISM: Artificial Sequence
<220> FEATURE:
<223> OTHER INFORMATION: heavy chain of a humanised TREM-1 antibody derived from mouse

<400> SEQUENCE: 2

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
```

```
              65                  70                  75                  80
Ala Tyr Leu Gln Met Asn Ser Leu Lys Thr Glu Asp Thr Ala Val Tyr
                    85                  90                  95

Tyr Cys Thr Arg Asp Met Gly Ile Arg Arg Gln Phe Ala Tyr Trp Gly
                   100                 105                 110

Gln Gly Thr Leu Val Thr Val Ser Ala Ser Thr Lys Gly Pro Ser
                   115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                   165                 170                 175

Val Leu Gln Ser Ser Gly Leu Tyr Ser Leu Ser Ser Val Val Thr Val
                   180                 185                 190

Pro Ser Ser Ser Leu Gly Thr Lys Thr Tyr Thr Cys Asn Val Asp His
                   195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                   245                 250                 255

Thr Pro Glu Val Thr Cys Val Val Val Asp Val Ser Gln Glu Asp Pro
                   260                 265                 270

Glu Val Gln Phe Asn Trp Tyr Val Asp Gly Val Glu Val His Asn Ala
                   275                 280                 285

Lys Thr Lys Pro Arg Glu Glu Gln Phe Asn Ser Thr Tyr Arg Val Val
                   290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                   325                 330                 335

Ile Ser Lys Ala Lys Gly Gln Pro Arg Glu Pro Gln Val Tyr Thr Leu
                   340                 345                 350

Pro Pro Ser Gln Glu Glu Met Thr Lys Asn Gln Val Ser Leu Thr Cys
                   355                 360                 365

Leu Val Lys Gly Phe Tyr Pro Ser Asp Ile Ala Val Glu Trp Glu Ser
                   370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                   405                 410                 415

Arg Trp Gln Glu Gly Asn Val Phe Ser Cys Ser Val Met His Glu Ala
                   420                 425                 430

Leu His Asn His Tyr Thr Gln Lys Ser Leu Ser Leu Ser Leu Gly Lys
                   435                 440                 445

<210> SEQ ID NO 3
<211> LENGTH: 218
<212> TYPE: PRT
<213> ORGANISM: Artificial Sequence
<220> FEATURE:
<223> OTHER INFORMATION: light chain of a humanised TREM-1 antibody
      derived from mouse
```

```
<220> FEATURE:
<221> NAME/KEY: CHAIN
<222> LOCATION: (1)..(218)

<400> SEQUENCE: 3

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 218
<212> TYPE: PRT
<213> ORGANISM: Artificial Sequence
<220> FEATURE:
<223> OTHER INFORMATION: light chain of a humanised TREM-1 antibody
      derived from mouse

<400> SEQUENCE: 4

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Ser Asp Pro Tyr Thr Phe Gly Gln Gly Thr Lys Leu Glu Ile Lys Arg
            100                 105                 110
```

```
Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 5
<211> LENGTH: 218
<212> TYPE: PRT
<213> ORGANISM: Artificial Sequence
<220> FEATURE:
<223> OTHER INFORMATION: light chain of a humanised TREM-1 antibody derived from mouse

<400> SEQUENCE: 5

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 6
<211> LENGTH: 218
<212> TYPE: PRT

```
<213> ORGANISM: Artificial Sequence
<220> FEATURE:
<223> OTHER INFORMATION: light chain of a humanised TREM-1 antibody
      derived from mouse

<400> SEQUENCE: 6

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Ser Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 7
<211> LENGTH: 218
<212> TYPE: PRT
<213> ORGANISM: Artificial Sequence
<220> FEATURE:
<223> OTHER INFORMATION: light chain of a humanised TREM-1 antibody
      derived from mouse

<400> SEQUENCE: 7

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
```

```
            100                 105                 110
Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 8
<211> LENGTH: 218
<212> TYPE: PRT
<213> ORGANISM: Artificial Sequence
<220> FEATURE:
<223> OTHER INFORMATION: light chain of a humanised TREM-1 antibody
      derived from mouse

<400> SEQUENCE: 8

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 9
<211> LENGTH: 218
```

```
<212> TYPE: PRT
<213> ORGANISM: Artificial Sequence
<220> FEATURE:
<223> OTHER INFORMATION: light chain of a humanised TREM-1 antibody
      derived from mouse

<400> SEQUENCE: 9

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Ala
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 10
<211> LENGTH: 218
<212> TYPE: PRT
<213> ORGANISM: Artificial Sequence
<220> FEATURE:
<223> OTHER INFORMATION: light chain of a humanised TREM-1 antibody
      derived from mouse

<400> SEQUENCE: 10

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Ser
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95
```

```
Glu Asp Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
            210                 215

<210> SEQ ID NO 11
<211> LENGTH: 448
<212> TYPE: PRT
<213> ORGANISM: Artificial Sequence
<220> FEATURE:
<223> OTHER INFORMATION: heavy chain of a humanised TREM-1 antibody
      derived from mouse

<400> SEQUENCE: 11

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Tyr Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 12
<211> LENGTH: 448
<212> TYPE: PRT
<213> ORGANISM: Artificial Sequence
<220> FEATURE:
<223> OTHER INFORMATION: heavy chain of a humanised TREM-1 antibody
      derived from mouse

<400> SEQUENCE: 12

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
            35                  40                  45

Gly Arg Ile Arg Thr Lys Ser Ser Ser Tyr Ala Thr Tyr Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
```

-continued

```
145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 13
<211> LENGTH: 448
<212> TYPE: PRT
<213> ORGANISM: Artificial Sequence
<220> FEATURE:
<223> OTHER INFORMATION: heavy chain of a humanised TREM-1 antibody
      derived from mouse

<400> SEQUENCE: 13

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
                20                  25                  30

Ala Met His Trp Val Arg Gln Ala Ser Gly Lys Gly Leu Glu Trp Val
                35                  40                  45

Gly Arg Ile Arg Thr Lys Ser Ser Ser Tyr Tyr Thr Tyr Tyr Ala Ala
        50                  55                  60
```

-continued

```
Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 14
<211> LENGTH: 218
<212> TYPE: PRT
<213> ORGANISM: Artificial Sequence
<220> FEATURE:
<223> OTHER INFORMATION: light chain of a humanised TREM-1 antibody derived from mouse

<400> SEQUENCE: 14

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Ala
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 15
<211> LENGTH: 448
<212> TYPE: PRT
<213> ORGANISM: Artificial Sequence
<220> FEATURE:
<223> OTHER INFORMATION: heavy chain of a humanised TREM-1 antibody
      derived from mouse

<400> SEQUENCE: 15

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Asn Tyr Tyr Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser

```
            115                 120                 125
Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 16
<211> LENGTH: 448
<212> TYPE: PRT
<213> ORGANISM: Artificial Sequence
<220> FEATURE:
<223> OTHER INFORMATION: heavy chain of a humanised TREM-1 antibody
      derived from mouse

<400> SEQUENCE: 16

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30
```

```
Ala Met His Trp Val Arg Gln Ala Ser Gly Lys Gly Leu Glu Trp Val
        35                  40                  45
Gly Arg Ile Arg Thr Lys Ser Ser Asn Tyr Tyr Thr Tyr Tyr Ala Ala
 50                  55                  60
Ser Val Lys Gly Arg Phe Thr Ile Ser Arg Asp Asp Ser Lys Asn Thr
 65                  70                  75                  80
Ala Tyr Leu Gln Met Asn Ser Leu Lys Thr Glu Asp Thr Ala Val Tyr
                 85                  90                  95
Tyr Cys Thr Arg Asp Met Gly Ile Arg Arg Gln Phe Ala Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Lys Thr Tyr Thr Cys Asn Val Asp His
            195                 200                 205
Lys Pro Ser Asn Thr Lys Val Asp Lys Arg Val Glu Ser Lys Tyr Gly
        210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
                260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445
```

<210> SEQ ID NO 17
<211> LENGTH: 233
<212> TYPE: PRT
<213> ORGANISM: Macaca fascicularis

<400> SEQUENCE: 17

Met Arg Lys Thr Arg Leu Trp Gly Leu Leu Trp Met Leu Phe Val Ser
1               5                   10                  15

Glu Leu Arg Ala Thr Thr Glu Leu Thr Glu Glu Lys Tyr Glu Tyr Lys
            20                  25                  30

Glu Gly Gln Thr Leu Glu Val Lys Cys Asp Tyr Ala Leu Glu Lys Tyr
        35                  40                  45

Ala Asn Ser Arg Lys Ala Trp Gln Lys Met Glu Gly Lys Met Pro Lys
    50                  55                  60

Ile Leu Ala Lys Thr Glu Arg Pro Ser Glu Asn Ser His Pro Val Gln
65                  70                  75                  80

Val Gly Arg Ile Thr Leu Glu Asp Tyr Pro Asp His Gly Leu Leu Gln
                85                  90                  95

Val Gln Met Thr Asn Leu Gln Val Glu Asp Ser Gly Leu Tyr Gln Cys
            100                 105                 110

Val Ile Tyr Gln His Pro Lys Glu Ser His Val Leu Phe Asn Pro Ile
        115                 120                 125

Cys Leu Val Val Thr Lys Gly Ser Ser Gly Thr Pro Gly Ser Ser Glu
    130                 135                 140

Asn Ser Thr Gln Asn Val Tyr Arg Thr Pro Ser Thr Thr Ala Lys Ala
145                 150                 155                 160

Leu Gly Pro Arg Tyr Thr Ser Pro Arg Thr Val Thr Gln Ala Pro Pro
                165                 170                 175

Glu Ser Thr Val Val Ser Thr Pro Gly Ser Glu Ile Asn Leu Thr
            180                 185                 190

Asn Val Thr Asp Ile Ile Arg Val Pro Val Phe Asn Ile Val Ile Ile
        195                 200                 205

Val Ala Gly Gly Phe Leu Ser Lys Ser Leu Val Phe Ser Val Leu Phe
    210                 215                 220

Ala Val Thr Leu Arg Ser Phe Gly Pro
225                 230

<210> SEQ ID NO 18
<211> LENGTH: 219
<212> TYPE: PRT
<213> ORGANISM: Artificial Sequence
<220> FEATURE:
<223> OTHER INFORMATION: heavy chain of the Fab region of mAb 0170
      derived from mouse

<400> SEQUENCE: 18

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr

```
                        85                  90                  95
Tyr Cys Thr Arg Asp Met Gly Ile Arg Arg Gln Phe Ala Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val
    210                 215

<210> SEQ ID NO 19
<211> LENGTH: 218
<212> TYPE: PRT
<213> ORGANISM: Artificial Sequence
<220> FEATURE:
<223> OTHER INFORMATION: light chain of the Fab region of mAb 0170
      derived from mouse

<400> SEQUENCE: 19

Asp Ile Val Leu Thr Gln Ser Pro Asp Ser Leu Ala Val Ser Leu Gly
1               5                   10                  15
Glu Arg Ala Thr Ile Asn Cys Arg Ala Ser Glu Ser Val Asp Thr Phe
            20                  25                  30
Asp Tyr Ser Phe Leu His Trp Tyr Gln Gln Lys Pro Gly Gln Pro Pro
        35                  40                  45
Lys Leu Leu Ile Tyr Arg Ala Ser Asn Leu Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Ser Asn
                85                  90                  95
Glu Asp Pro Tyr Thr Phe Gly Gln Gly Thr Lys Leu Glu Ile Lys Arg
                100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```